United States Patent
Berthel et al.

(10) Patent No.: US 9,540,345 B2
(45) Date of Patent: Jan. 10, 2017

(54) ANTIVIRAL COMPOUNDS

(71) Applicant: Hoffmann-La Roche Inc., Nutley, NJ (US)

(72) Inventors: Steven Joseph Berthel, Mendham Township, NJ (US); Zhi Chen, Livingston, NJ (US); Feng Chi, Basking Ridge, NJ (US); Elbert Chin, San Mateo, CA (US); David Shawn Erickson, Leonia, NJ (US); Stephen Deems Gabriel, Morristown, NJ (US); Buelent Kocer, Maulburg (DE); Eric Mertz, Fair Lawn, NJ (US); Jean-Marc Plancher, Hagenthal-le-Bas (FR); Robert J. Weikert, Basel (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 13 days.

(21) Appl. No.: 14/766,905

(22) PCT Filed: Mar. 3, 2014

(86) PCT No.: PCT/EP2014/054015
§ 371 (c)(1),
(2) Date: Aug. 10, 2015

(87) PCT Pub. No.: WO2014/135471
PCT Pub. Date: Sep. 12, 2014

(65) Prior Publication Data
US 2015/0368228 A1 Dec. 24, 2015

Related U.S. Application Data

(60) Provisional application No. 61/772,943, filed on Mar. 5, 2013.

(51) Int. Cl.
C07D 401/12 (2006.01)
C07D 403/12 (2006.01)
C07D 487/10 (2006.01)
C07D 471/04 (2006.01)
C07D 409/12 (2006.01)
C07D 249/14 (2006.01)
A61K 31/4196 (2006.01)
A61K 31/437 (2006.01)
A61K 31/496 (2006.01)
A61K 31/501 (2006.01)
A61K 31/4439 (2006.01)
A61K 31/506 (2006.01)
A61K 38/21 (2006.01)
A61K 45/06 (2006.01)

(52) U.S. Cl.
CPC ......... *C07D 401/12* (2013.01); *A61K 31/4196* (2013.01); *A61K 31/437* (2013.01); *A61K 31/4439* (2013.01); *A61K 31/496* (2013.01); *A61K 31/501* (2013.01); *A61K 31/506* (2013.01); *A61K 38/21* (2013.01); *A61K 45/06* (2013.01); *C07D 249/14* (2013.01); *C07D 403/12* (2013.01); *C07D 409/12* (2013.01); *C07D 471/04* (2013.01); *C07D 487/10* (2013.01)

(58) Field of Classification Search
None
See application file for complete search history.

(56) References Cited

U.S. PATENT DOCUMENTS

2011/0190269 A1* 8/2011 Baumann ............. C07D 471/04
514/217.07

FOREIGN PATENT DOCUMENTS

| WO | 00/25780 | | 5/2000 | |
|---|---|---|---|---|
| WO | WO 02/057240 | * | 7/2002 | ........... C07D 249/14 |
| WO | 2004/046120 | | 6/2004 | |
| WO | 2006/047256 | | 5/2006 | |
| WO | 2011/092272 | | 8/2011 | |

OTHER PUBLICATIONS

"Guidance for Industry: Q3C—Tables and List" (Nov. 2003).*
The Japanese Office Action, issued on Sep. 2, 2016, in the related Japanese patent application No. 2015-560639.

* cited by examiner

*Primary Examiner* — Alicia L Otton

(57) ABSTRACT

The present invention discloses compounds of Formula (I): wherein the variables in Formula (I) are defined as described herein. Also disclosed are pharmaceutical compositions containing such compounds and methods for using the compounds of Formula (I) in the prevention or treatment of HCV infection.

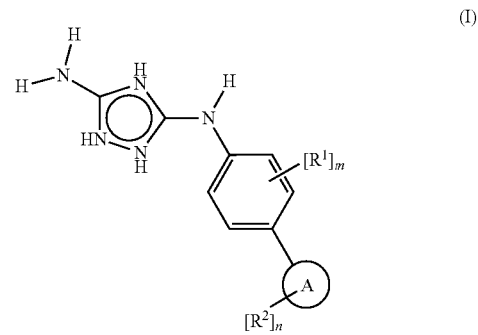

2 Claims, No Drawings

ANTIVIRAL COMPOUNDS

This application is a National Stage Application of PCT/EP2014/054015 filed Mar. 3, 2014, which claims priority from U.S. Provisional Patent Application No. 61/772,943, filed on Mar. 5, 2013. The priority of both said PCT and U.S. Provisional Patent Application are claimed. Each of the prior mentioned applications is hereby incorporated by reference herein in its entirety.

The present invention provides compounds of Formula I useful as inhibitors of hepatitis C virus (HCV), as inhibitors of HCV infection, and for the prevention and treatment of hepatitis C infection.

Hepatitis C virus (HCV) infection is a major health problem that affects 170 million people worldwide and 3-4 million people in the United States (Armstrong, G. L., et al., Ann. Intern. Med. 2006, 144:705-714; Lauer, G. M., et al., N. Eng. J. Med. 2001, 345:41-52). HCV infection leads to chronic liver disease, such as cirrhosis and hepatocellular carcinoma in a substantial number of infected individuals. Chronic HCV infection associated liver cirrhosis and hepatocellular carcinoma are also the leading cause of liver transplantation in the United States. Current treatments for HCV infection include immunotherapy with pegylated interferon-α in combination with the nucleoside-analog ribavirin. Pegylated interferon-α in combination with ribavirin and one of the two recently approved HCV NS3 protease inhibitors Incivek or Victrelis is the current standard of care for the treatment of genotype 1HCV infected patients, the most difficult to treat patient population. However, current HCV treatments are compromised by suboptimal sustained virological response rates and associated with severe side effects, as well as resistance to the protease inhibitors. Therefore there is a clear need for improved antiviral drugs with better efficacy, safety, and resistance profiles.

The infection of human hepatocytes by HCV, also known as HCV entry, is mediated by the functional interactions of virally-encoded envelope glycoproteins E1 and E2 and host cell co-receptors, followed by a receptor-mediated endocytosis processes. This HCV entry step is a putative target for therapeutic intervention. Several virally-encoded enzymes are also putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

Systems have been developed to study the biology of HCV entry into host cells. Pseudotyping systems where the E1 and E2 glycoproteins are used to functionally replace the glycoproteins of retroviruses have been developed (Bartosch, B., Dubuisson, J. and Cosset, F.-L. J. Exp. Med. 2003, 197:633-642; Hsu, M. et al. Proc. Natl. Acad. Sci. USA. 2003, 100:7271-7276). These systems yield HCV pseudoparticles that bind to and enter host cells in a manner which is believed to be analogous to the natural virus, thus making them a convenient tool to study the viral entry steps as well as to identify inhibitors blocking this process.

There is a clear and long-felt need to develop effective therapeutics for treatment of HCV infection. Specifically, there is a need to develop compounds that selectively inhibit HCV viral entry and replication and that are useful for treating HCV-infected patients and protecting liver transplant patients from HCV re-infection. This application discloses novel compounds that are effective in prevention of HCV infection. Additionally, the disclosed compounds provide advantages for pharmaceutical uses, for example, with respect to their mechanism of action, binding, prevention of infection, inhibition efficacy, and target selectivity.

SUMMARY OF THE INVENTION

The application provides compound of formula I

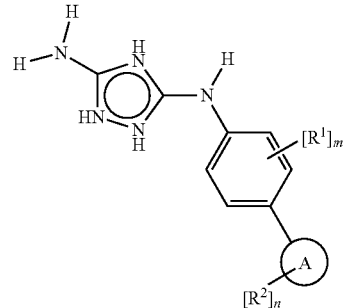

A is unsaturated or partially unsaturated monocyclic or bicyclic heteroaryl or monocyclic or spirocyclic heterocycloalkyl;

each $R^1$ is independently halo, halo lower alkyl, or lower alkyl sulfonyl;

m is 0, 1, or 2;

each $R^2$ is is independently halo, lower alkoxy, oxo, amino, lower alkyl, $C(=O)OR^{2'}$, $S(=O)_2R^{2'}$, $S(=O)_2NHR^{2'}$, hydroxyl lower alkyl, $C(=O)NHR^{2'}$, or $C(=O)R^{2'}$;

n is 0, 1, or 2; and $R^{2'}$ is lower alkyl, halo lower alkyl, or adamantly;

or a pharmaceutically acceptable salt thereof.

The application provides a method for preventing a Hepatitis C Virus (HCV) infection comprising administering to a patient in need thereof a therapeutically effective amount of a compound of Formula I.

The application provides a method for treating a Hepatitis C Virus (HCV) infection comprising administering to a patient in need thereof a therapeutically effective amount of a compound of Formula I.

The application provides a composition comprising a compound of Formula I and a pharmaceutically acceptable excipient.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "- - - - -" drawn through a bond each refer to the point of attachment of a functional group or other chemical moiety to the rest of the molecule of which it is a part. Thus, for example:

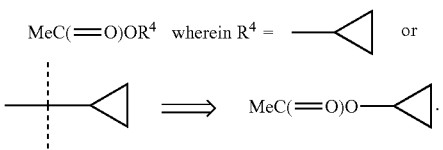

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

If a substituent is designated to be "absent", the substituent is not present.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's The Pharmacological Basis of Therapeutics, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "carbonyl" or "acyl" as used herein denotes a group of formula —C(=O)R wherein R is hydrogen or lower alkyl as defined herein.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The terms "haloalkoxy" or "halo lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The term "sulfinyl" as used herein denotes a —SO— group.

The term "sulfonyl" as used herein denotes a —SO$_2$— group.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The term "lower alkyl sulfonylamido" as used herein refers to a group of formula —S(=O)$_2$NR$_2$ wherein each R is independently hydrogen or $C_{1-3}$ alkyl, and lower alkyl is as defined herein.

The term "trifluoromethyl sulfonyl" as used herein refers to a group of formula —S(=O)$_2$CF$_3$.

The term "trifluoromethyl sulfinyl" as used herein refers to a group of formula —S(=O)CF$_3$.

The term "trifluoromethyl sulfanyl" as used herein refers to a group of formula —SCF$_3$.

The term "nitro" as used herein refers to a group of formula —N$^+$(=O)O$^-$.

The term "carboxyl" as used herein refers to a group of formula —C(=O)R$_2$ wherein each R is independently hydrogen or $C_{1-3}$ alkyl, and lower alkyl is as defined herein.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "amino" as used herein denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine dimethylamine, diethylamine, dipropylamine and diisopropylamine.

The term "amido" as used herein denotes a group of the formula —C(=O)NR'R" or —NR'C(=O)R" wherein R' and R" are independently hydrogen, alkyl, alkoxy, cycloalkyl, heterocycloalkyl, aryl or heteroaryl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

Inhibitors of HCV Entry

The application provides a compound of formula I

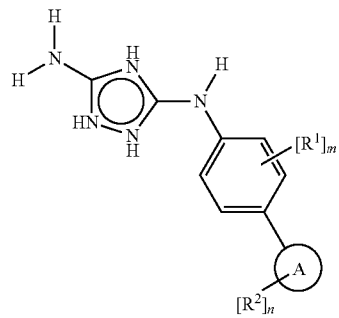

I

A is unsaturated or partially unsaturated monocyclic or bicyclic heteroaryl or monocyclic or spirocyclic heterocycloalkyl;

each $R^1$ is independently halo, halo lower alkyl, or lower alkyl sulfonyl;

m is 0, 1, or 2;

each $R^2$ is is independently halo, lower alkoxy, oxo, amino, lower alkyl, C(=O)OR$^{2'}$, S(=O)$_2$R$^{2'}$, S(=O)$_2$NHR$^{2'}$, hydroxyl lower alkyl, C(=O)NHR$^{2'}$, or C(=O)R$^{2'}$;

n is 0, 1, or 2; and $R^{2'}$ is lower alkyl, halo lower alkyl, or adamantly;

or a pharmaceutically acceptable salt thereof.

The application provides a compound of formula I, wherein m is 1.

The application provides a compound of formula I, wherein m is 2.

The application provides a compound of formula I, wherein one $R^1$ is halo and the other is halo lower alkyl.

The application provides a compound of formula I, wherein m is 2 and one $R^1$ is halo and the other is halo lower alkyl.

The application provides a compound of formula I, wherein both $R^1$ are halo.

The application provides a compound of formula I, wherein m is 2 and both $R^1$ are halo.

The application provides any of the above compounds of formula I, wherein n is 0.

The application alternatively provides any of the above compounds of formula I, wherein n is 1.

The application alternatively provides any of the above compounds of formula I, wherein n is 2.

The application provides any of the above compounds of formula I, wherein A is pyridinyl, pyrimidinyl, pyridazinyl, triazolyl, tetrazolyl, piperazinyl, 2,6-diaza-spiro[3.3]heptanyl, azetidinyl, thiophenyl, or pyrazolyl.

The application provides any of the above compounds of formula I, wherein $R^2$ is halo, lower alkoxy, oxo, amino, lower alkyl, C(=O)OR$^{2'}$, S(=O)$_2$R$^{2'}$, S(=O)$_2$NHR$^{2'}$, hydroxyl lower alkyl, C(=O)NHR$^{2'}$, or C(=O)R$^{2'}$.

The application provides any of the above compounds of formula I, wherein $R^{2'}$ is lower alkyl or halo lower alkyl.

The application provides a compound selected from the group consisting of:

$N^3$-[3,5-Dichloro-4-(6-methoxy-pyridin-3-yl)-phenyl]-1H-[1,2,4]triazole-3,5-diamine;

$N^3$-[3,5-Dichloro-4-(5-methanesulfonyl-pyridin-3-yl)-phenyl]-1H-[1,2,4]triazole-3,5-diamine;

5-[4-(5-Amino-1H-[1,2,4]triazol-3-ylamino)-2,6-dichloro-phenyl]-1H-pyridin-2-one;

$N^3$-[4-(6-Amino-pyridin-3-yl)-3,5-dichloro-phenyl]-1H-[1,2,4]triazole-3,5-diamine;

$N^3$-[4-(2-Amino-pyrimidin-5-yl)-3,5-dichloro-phenyl]-1H-[1,2,4]triazole-3,5-diamine;

N3-[3,5-Dichloro-4-(2-methoxy-pyridin-4-yl)-phenyl]-1H-[1,2,4]triazole-3,5-diamine;

4-[4-(5-Amino-1H-[1,2,4]triazol-3-ylamino)-2,6-dichloro-phenyl]-1H-pyridin-2-one;

N-{5-[4-(5-Amino-1H-[1,2,4]triazol-3-ylamino)-2,6-dichloro-phenyl]-pyridin-2-yl}-methanesulfonamide;

$N^5$-[3-Fluoro-4-(6-fluoro-pyridin-3-yl)-5-trifluoromethyl-phenyl]-1H-[1,2,4]triazole-3,5-diamine;

$N^5$-(3-Fluoro-4-pyridin-3-yl-5-trifluoromethyl-phenyl)-1H-[1,2,4]triazole-3,5-diamine;

$N^3$-[3,5-Dichloro-4-(6-methanesulfonyl-pyridin-3-yl)-phenyl]-1H-[1,2,4]triazole-3,5-diamine;

6-[4-(5-Amino-1H-[1,2,4]triazol-3-ylamino)-2,6-dichloro-phenyl]-2,6-diaza-spiro[3.3]heptane-2-carboxylic acid tert-butyl ester;

$N^3$-(3-Chloro-4-pyridazin-3-yl-phenyl)-1H-[1,2,4]triazole-3,5-diamine;

$N^3$-[3-Chloro-4-(1-methyl-1H-tetrazol-5-yl)-phenyl]-1H-[1,2,4]triazole-3,5-diamine;

$N^3$-[3-Chloro-4-(2-methyl-2H-[1,2,4]triazol-3-yl)-phenyl]-1H-[1,2,4]triazole-3,5-diamine;

$N^3$-(3,5-Dichloro-4-pyrazol-1-yl-phenyl)-1H-[1,2,4]triazole-3,5-diamine;

4-[4-(5-Amino-1H-[1,2,4]triazol-3-ylamino)-2,6-dichloro-phenyl]-3,6-dihydro-2H-pyridine-1-carboxylic acid tert-butyl ester;

$N^3$-[3,5-Dichloro-4-(1,2,3,6-tetrahydro-pyridin-4-yl)-phenyl]-1H-[1,2,4]triazole-3,5-diamine;

4-[4-(5-Amino-1H-[1,2,4]triazol-3-ylamino)-2-chloro-6-trifluoromethyl-phenyl]-3,6-dihydro-2H-pyridine-1-carboxylic acid tert-butyl ester;

$N^3$-[3-Chloro-4-(1,2,3,6-tetrahydro-pyridin-4-yl)-5-trifluoromethyl-phenyl]-1H-[1,2,4]triazole-3,5-diamine;

$N^5$-(3,5-Dichloro-4-[1,2,4]triazolo[4,3-a]pyridin-3-yl-phenyl)-1H-[1,2,4]triazole-3,5-diamine;

N-{3-Chloro-4-[6-(propane-2-sulfonyl)-pyridin-3-yl]-5-trifluoromethyl-phenyl}-4H-[1,2,4]triazole-3,5-diamine;

5-[4-(5-Amino-1H-[1,2,4]triazol-3-ylamino)-2-chloro-6-trifluoromethyl-phenyl]-pyridine-2-sulfonic acid tert-butyl-amide;

5-[4-(5-Amino-1H-[1,2,4]triazol-3-ylamino)-2-chloro-6-trifluoromethyl-phenyl]-pyridine-2-sulfonic acid (2,2,2-trifluoro-1,1-dimethyl-ethyl)-amide;

5-[4-(5-Amino-1H-[1,2,4]triazol-3-ylamino)-2-chloro-6-trifluoromethyl-phenyl]-pyridine-2-sulfonic acid adamantan-1-ylamide;

$N^3$-[2-Chloro-4'-(4-methyl-piperazin-1-yl)-6-trifluoromethyl-biphenyl-4-yl]-1H-[1,2,4]triazole-3,5-diamine;

$N^3$-(3-Chloro-4-pyridazin-3-yl-phenyl)-1H-[1,2,4]triazole-3,5-diamine;

1-[4-(5-Amino-1H-[1,2,4]triazol-3-ylamino)-phenyl]-1H-pyridin-2-one;

1-[4-(5-Amino-1H-[1,2,4]triazol-3-ylamino)-2-chloro-phenyl]-1H-pyridin-2-one;

1-[4-(5-Amino-1H-[1,2,4]triazol-3-ylamino)-2,6-dichloro-phenyl]-1H-pyridin-2-one;

5-[4-(5-Amino-1H-[1,2,4]triazol-3-ylamino)-2-chloro-6-trifluoromethyl-phenyl]-pyridine-2-carboxylic acid methylamide;

$N^3$-(3,5-Dichloro-4-pyridazin-4-yl-phenyl)-1H-[1,2,4]triazole-3,5-diamine;

1-{3-[4-(5-Amino-1H-[1,2,4]triazol-3-ylamino)-2,6-dichloro-phenyl]-thiophen-2-yl}-ethanone;

N3-(3,5-Dichloro-4-pyridin-4-yl-phenyl)-1H-[1,2,4]triazole-3,5-diamine;

N3-[3,5-Dichloro-4-(5-chloro-thiophen-2-yl)-phenyl]-1H-[1,2,4]triazole-3,5-diamine;

N3-(3,5-Dichloro-4-pyridin-3-yl-phenyl)-1H-[1,2,4]triazole-3,5-diamine;

N3-[3,5-Dichloro-4-(1H-pyrazol-3-yl)-phenyl]-1H-[1,2,4]triazole-3,5-diamine;

N3-(3,5-Dichloro-4-pyrimidin-5-yl-phenyl)-1H-[1,2,4]triazole-3,5-diamine;

N3-[3,5-Dichloro-4-(2-methoxy-pyrimidin-5-yl)-phenyl]-1H-[1,2,4]triazole-3,5-diamine;

N3-[3,5-Dichloro-4-(6-trifluoromethyl-pyridin-3-yl)-phenyl]-1H-[1,2,4]triazole-3,5-diamine;

N3-[3,5-Dichloro-4-(1-methyl-3-trifluoromethyl-1H-pyrazol-4-yl)-phenyl]-1H-[1,2,4]triazole-3,5-diamine;

N3-[3,5-Dichloro-4-(5-chloro-pyridin-3-yl)-phenyl]-1H-[1,2,4]triazole-3,5-diamine; and
N3-[3,5-Dichloro-4-(6-methoxy-pyridin-2-yl)-phenyl]-1H-[1,2,4]triazole-3,5-diamine.

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering a combination of antiviral agents that inhibits replication of HCV.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

The application provides a composition comprising a compound of Formula I and a pharmaceutically acceptable excipient.

The application provides the use of the compound of Formula I in the preparation of a medicament for the prevention of HCV.

The application provides the use of the compound of Formula I in the preparation of a medicament for the treatment of HCV.

The application provides any compound, composition, method or use as described herein.

Compounds

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of compounds according to generic Formula I:

TABLE I

| # | Nomenclature | Structure |
|---|---|---|
| 1 | $N^3$-[3,5-Dichloro-4-(6-methoxy-pyridin-3-yl)-phenyl]-1H-[1,2,4]triazole-3,5-diamine | 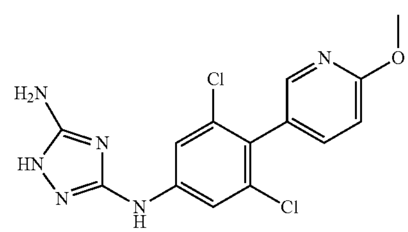 [SMILES: COc1ccc(-c2c(Cl)cc(Nc3n[nH]c(N)n3)cc2Cl)cn1] |
| 2 | $N^3$-[3,5-Dichloro-4-(5-methanesulfonyl-pyridin-3-yl)-phenyl]-1H-[1,2,4]triazole-3,5-diamine | 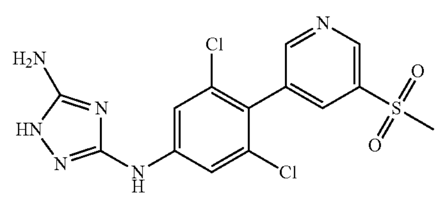 [SMILES: CS(=O)(=O)c1cncc(-c2c(Cl)cc(Nc3n[nH]c(N)n3)cc2Cl)c1] |
| 3 | 5-[4-(5-Amino-1H-[1,2,4]triazol-3-ylamino)-2,6-dichloro-phenyl]-1H-pyridin-2-one | 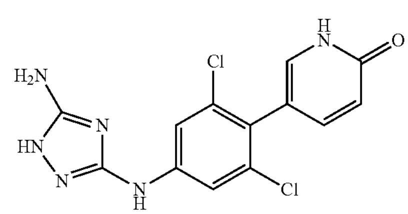 [SMILES: Nc1nc(Nc2cc(Cl)c(-c3ccc(=O)[nH]c3)c(Cl)c2)n[nH]1] |

TABLE I-continued

| # | Nomenclature | Structure |
|---|---|---|
| 4 | N³-[4-(6-Amino-pyridin-3-yl)-3,5-dichloro-phenyl]-1H-[1,2,4]triazole-3,5-diamine | 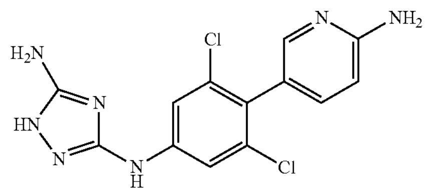 [SMILES: Nc1ccc(-c2c(Cl)cc(Nc3n[nH]c(N)n3)cc2Cl)cn1] |
| 5 | N³-[4-(2-Amino-pyrimidin-5-yl)-3,5-dichloro-phenyl]-1H-[1,2,4]triazole-3,5-diamine | 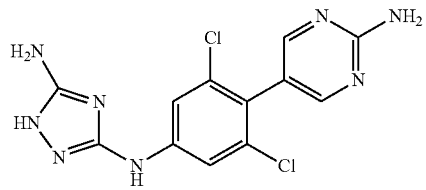 [SMILES: Nc1ncc(-c2c(Cl)cc(Nc3n[nH]c(N)n3)cc2Cl)cn1] |
| 6 | N3-[3,5-Dichloro-4-(2-methoxy-pyridin-4-yl)-phenyl]-1H-[1,2,4]triazole-3,5-diamine | 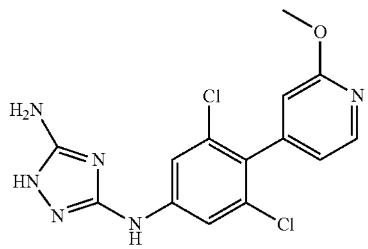 [SMILES: COc1cc(-c2c(Cl)cc(Nc3n[nH]c(N)n3)cc2Cl)ccn1] |
| 7 | 4-[4-(5-Amino-1H-[1,2,4]triazol-3-ylamino)-2,6-dichloro-phenyl]-1H-pyridin-2-one | 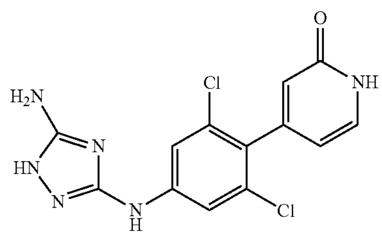 [SMILES: Nc1nc(Nc2cc(Cl)c(-c3cc[nH]c(=O)c3)c(Cl)c2)n[nH]1] |
| 8 | N-{5-[4-(5-Amino-1H-[1,2,4]triazol-3-ylamino)-2,6-dichloro-phenyl]-pyridin-2-yl}-methanesulfonamide | 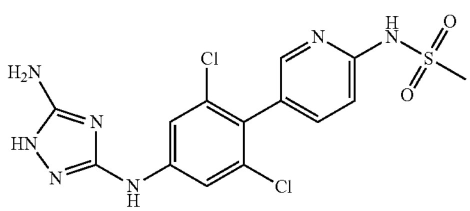 [SMILES: CS(=O)(=O)Nc1ccc(-c2c(Cl)cc(Nc3n[nH]c(N)n3)cc2Cl)cn1] |
| 9 | N⁵-[3-Fluoro-4-(6-fluoro-pyridin-3-yl)-5-trifluoromethyl-phenyl]-1H-[1,2,4]triazole-3,5-diamine | 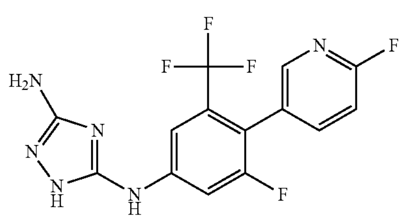 [SMILES: Nc1n[nH]c(Nc2cc(F)c(-c3ccc(F)nc3)c(C(F)(F)F)c2)n1] |
| 10 | N⁵-(3-Fluoro-4-pyridin-3-yl-5-trifluoromethyl-phenyl)-1H-[1,2,4]triazole-3,5-daimine | 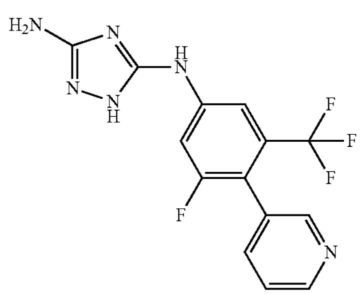 [SMILES: Nc1n[nH]c(Nc2cc(F)c(-c3cccnc3)c(C(F)(F)F)c2)n1] |

TABLE I-continued

| # | Nomenclature |
|---|---|
| 11 | $N^3$-[3,5-Dichloro-4-(6-methanesulfonyl-pyridin-3-yl)-phenyl]-1H-[1,2,4]triazole-3,5-diamine |
| 12 | 6-[4-(5-Amino-1H-[1,2,4]triazol-3-ylamino)-2,6-dichloro-phenyl]-2,6-diaza-spiro[3.3]heptane-2-carboxylic acid tert-butyl ester |
| 13 | $N^3$-(3-Chloro-4-pyridazin-3-yl-phenyl)-1H-[1,2,4]triazole-3,5-diamine |
| 14 | $N^3$-[3-Chloro-4-(1-methyl-1H-tetrazol-5-yl)-phenyl]-1H-[1,2,4]triazole-3,5-diamine |
| 15 | $N^3$-[3-Chloro-4-(2-methyl-2H-[1,2,4]triazol-3-yl)-phenyl]-1H-[1,2,4]triazole-3,5-diamine |
| 16 | $N^3$-(3,5-Dichloro-4-pyrazol-1-yl-phenyl)-1H-[1,2,4]triazole-3,5-diamine |

TABLE I-continued

| # | Nomenclature | Structure |
|---|---|---|
| 17 | 4-[4-(5-Amino-1H-[1,2,4]triazol-3-ylamino)-2,6-dichloro-phenyl]-3,6-dihydro-2H-pyridine-1-carboxylic acid tert-butyl ester | 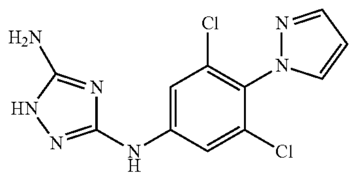 [SMILES: Nc1nc(Nc2cc(Cl)c(-n3cccn3)c(Cl)c2)n[nH]1] |
| 18 | N³-[3,5-Dichloro-4-(1,2,3,6-tetrahydro-pyridin-4-yl)-phenyl]-1H-[1,2,4]triazole-3,5-diamine | 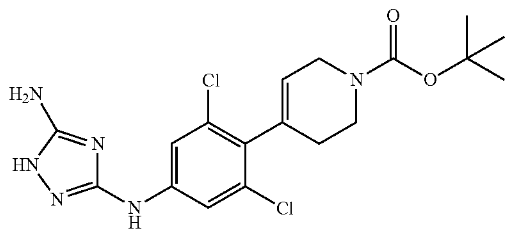 [SMILES: CC(C)(C)OC(=O)N1CC=C(c2c(Cl)cc(Nc3n[nH]c(N)n3)cc2Cl)CC1] |
| 19 | 4-[4-(5-Amino-1H-[1,2,4]triazol-3-ylamino)-2-chloro-6-trifluoromethyl-phenyl]-3,6-dihydro-2H-pyridine-1-carboxylic acid tert-butyl ester | 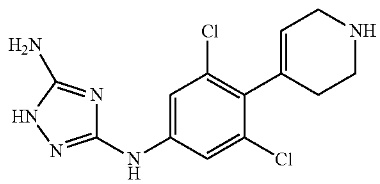 [SMILES: Nc1nc(Nc2cc(Cl)c(C3=CCNCC3)c(Cl)c2)n[nH]1] |
| 20 | N³-[3-Chloro-4-(1,2,3,6-tetrahydro-pyridin-4-yl)-5-trifluoromethyl-phenyl]-1H-[1,2,4]triazole-3,5-diamine | 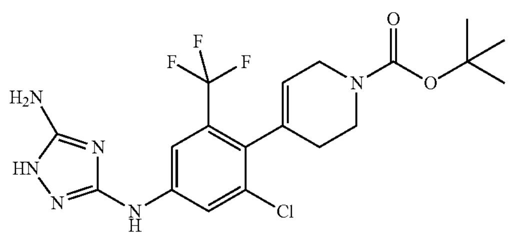 [SMILES: CC(C)(C)OC(=O)N1CC=C(c2c(Cl)cc(Nc3n[nH]c(N)n3)cc2C(F)(F)F)CC1] |
| 21 | N⁵-(3,5-Dichloro-4-[1,2,4]triazolo[4,3-a]pyridin-3-yl-phenyl)-1H-[1,2,4]triazole-3,5-diamine | 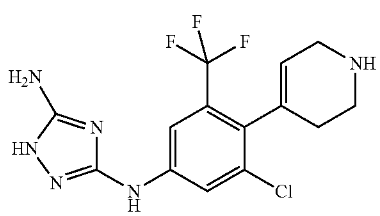 [SMILES: Nc1nc(Nc2cc(Cl)c(C3=CCNCC3)c(C(F)(F)F)c2)n[nH]1] |
| 22 | N-{3-Chloro-4-[6-(propane-2-sulfonyl)-pyridin-3-yl]-5-trifluoromethyl-phenyl}-4H-[1,2,4]triazole-3,5-diamine | 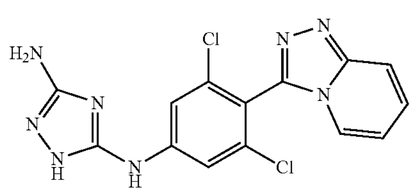 [SMILES: Nc1n[nH]c(Nc2cc(Cl)c(-c3nnc4ccccn34)c(Cl)c2)n1] |
| 23 | 5-[4-(5-Amino-1H-[1,2,4]triazol-3-ylamino)-2-chloro-6-trifluoromethyl-phenyl]-pyridine-2-sulfonic acid tert-butylamide | 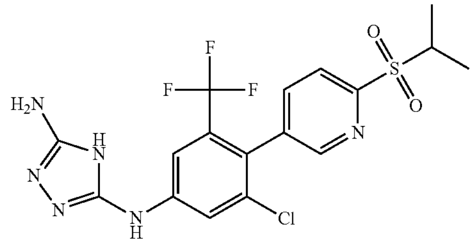 [SMILES: CC(C)S(=O)(=O)c1ccc(-c2c(Cl)cc(Nc3nnc(N)[nH]3)cc2C(F)(F)F)cn1] |

TABLE I-continued

| # | Nomenclature | Structure |
|---|---|---|
| 24 | 5-[4-(5-Amino-1H-[1,2,4]triazol-3-ylamino)-2-chloro-6-trifluoromethyl-phenyl]-pyridine-2-sulfonic acid (2,2,2-trifluoro-1,1-dimethyl-ethyl)-amide | 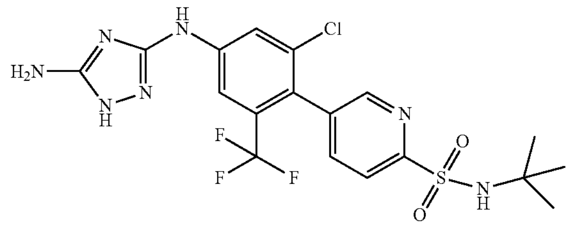 [SMILES: CC(C)(C)NS(=O)(=O)c1ccc(-c2c(Cl)cc(Nc3n[nH]c(N)n3)cc2C(F)(F)F)cn1] |
| 25 | 5-[4-(5-Amino-1H-[1,2,4]triazol-3-ylamino)-2-chloro-6-trifluoromethyl-phenyl]-pyridine-2-sulfonic acid adamantan-1-ylamide | 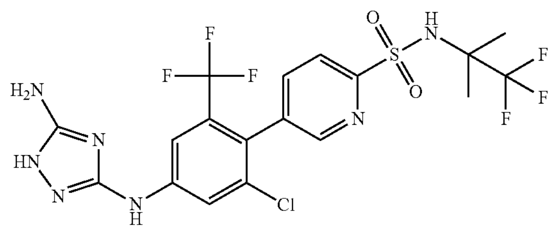 [SMILES: CC(C)(NS(=O)(=O)c1ccc(-c2c(Cl)cc(Nc3n[nH]c(N)n3)cc2C(F)(F)F)cn1)C(F)(F)F] |
| 26 | $N^3$-[2-Chloro-4'-(4-methyl-piperazin-1-yl)-6-trifluoromethyl-biphenyl-4-yl]-1H-[1,2,4]triazole-3,5-diamine | 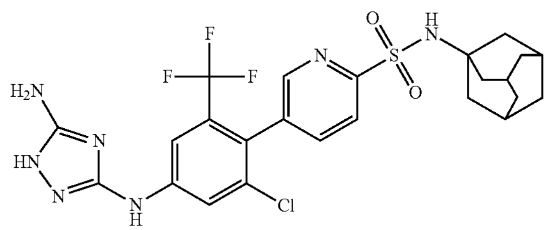 [SMILES: Nc1nc(Nc2cc(Cl)c(-c3ccc(S(=O)(=O)NC45CC6CC(CC(C6)C4)C5)nc3)c(C(F)(F)F)c2)n[nH]1] |
| 27 | $N^3$-(3-Chloro-4-pyridazin-3-yl-phenyl)-1H-[1,2,4]triazole-3,5-diamine | 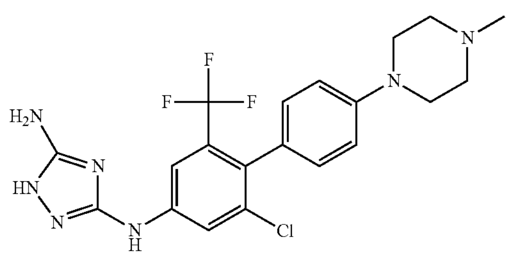 [SMILES: CN1CCN(c2ccc(-c3c(Cl)cc(Nc4n[nH]c(N)n4)cc3C(F)(F)F)cc2)CC1] |
| 28 | 1-[4-(5-Amino-1H-[1,2,4]triazol-3-ylamino)-phenyl]-1H-pyridin-2-one | 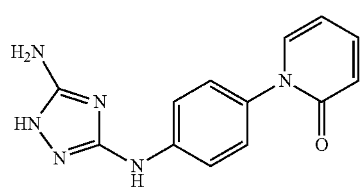 [SMILES: Nc1nc(Nc2ccc(-n3ccccc3=O)cc2)n[nH]1] |
| 29 | 1-[4-(5-Amino-1H-[1,2,4]triazol-3-ylamino)-2-chloro-phenyl]-1H-pyridin-2-one | 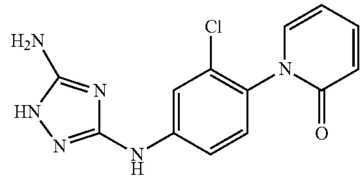 [SMILES: Nc1nc(Nc2ccc(-n3ccccc3=O)c(Cl)c2)n[nH]1] |
| 30 | 1-[4-(5-Amino-1H-[1,2,4]triazol-3-ylamino)-2,6-dichloro-phenyl]-1H-pyridin-2-one | 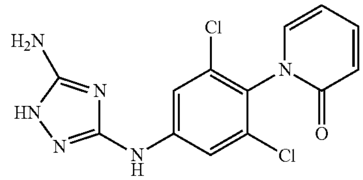 [SMILES: Nc1nc(Nc2cc(Cl)c(-n3ccccc3=O)c(Cl)c2)n[nH]1] |

TABLE I-continued

| # | Nomenclature |
|---|---|
| 31 | N*3*-[3,5-Dichloro-4-(1,4,5,6-tetra hydro-pyrimidin-2-yl)-phenyl]-1H-[1,2,4]triazole-3,5-diamine |
| 32 | 5-[4-(5-Amino-1H-[1,2,4]triazol-3-ylamino)-2-chloro-6-trifluoromethyl-phenyl]-pyridine-2-carboxylic acid methylamide |
| 33 | N³-(3,5-Dichloro-4-pyridazin-4-yl-phenyl)-1H-[1,2,4]triazol-3,5-diamine |
| 34 | 1-{3-[4-(5-Amino-1H-[1,2,4]triazol-3-ylamino)-2,6-dichloro-phenyl]-thiophen-2-yl}-ethanone |
| 35 | N3-(3,5-Dichloro-4-pyridin-4-yl-phenyl)-1H-[1,2,4]triazole-3,5-diamine |
| 36 | N3-[3,5-Dichloro-4-(5-chloro-thiophen-2-yl)-phenyl]-1H-[1,2,4]triazole-3,5-diamine |

TABLE I-continued

| # | Nomenclature | Structure |
|---|---|---|
| 37 | N3-(3,5-Dichloro-4-pyridin-3-yl-phenyl)-1H-[1,2,4]triazole-3,5-diamine | 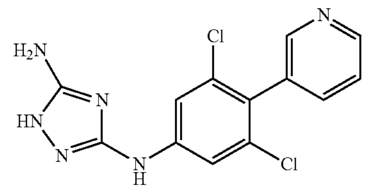 [SMILES: Nc1nc(Nc2cc(Cl)c(-c3cccnc3)c(Cl)c2)n[nH]1] |
| 38 | N3-[3,5-Dichloro-4-(1H-pyrazol-3-yl)-phenyl]-1H-[1,2,4]triazole-3,5-diamine | 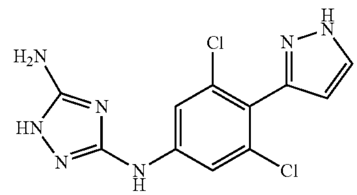 [SMILES: Nc1nc(Nc2cc(Cl)c(-c3cc[nH]n3)c(Cl)c2)n[nH]1] |
| 39 | N3-(3,5-Dichloro-4-pyrimidin-5-yl-phenyl)-1H-[1,2,4]triazole-3,5-diamine | 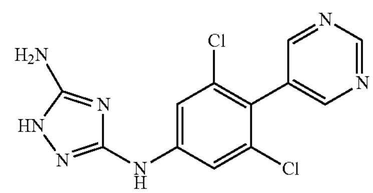 [SMILES: Nc1nc(Nc2cc(Cl)c(-c3cncnc3)c(Cl)c2)n[nH]1] |
| 40 | N3-[3,5-Dichloro-4-(2-methoxy-pyrimidin-5-yl)-phenyl]-1H-[1,2,4]triazole-3,5-diamine | 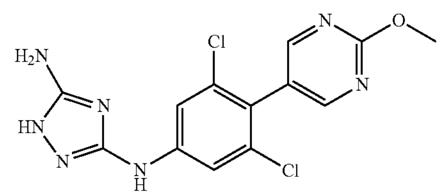 [SMILES: COc1ncc(-c2c(Cl)cc(Nc3n[nH]c(N)n3)cc2Cl)cn1] |
| 41 | N3-[3,5-Dichloro-4-(6-trifluoromethyl-pyridin-3-yl)-phenyl]-1H-[1,2,4]triazole-3,5-diamine | 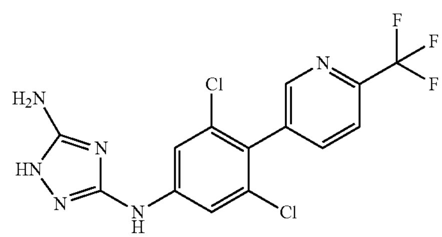 [SMILES: Nc1nc(Nc2cc(Cl)c(-c3ccc(C(F)(F)F)nc3)c(Cl)c2)n[nH]1] |
| 42 | N3-[3,5-Dichloro-4-(1-methyl-3-trifluoromethyl-1H-pyrazol-4-yl)-phenyl]-1H-[1,2,4]triazole-3,5-diamine | 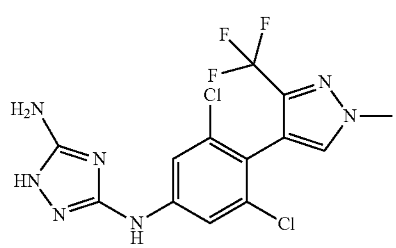 [SMILES: Cn1cc(-c2c(Cl)cc(Nc3n[nH]c(N)n3)cc2Cl)c(C(F)(F)F)n1] |
| 43 | N3-[3,5-Dichloro-4-(5-chloro-pyridin-3-yl)-phenyl]-1H-[1,2,4]triazole-3,5-diamine | 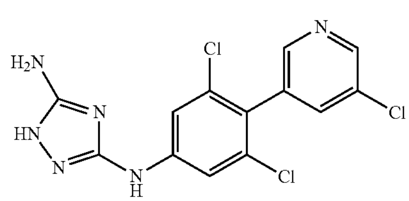 [SMILES: Nc1nc(Nc2cc(Cl)c(-c3cncc(Cl)c3)c(Cl)c2)n[nH]1] |

TABLE I-continued

| # | Nomenclature | Structure |
|---|---|---|
| 44 | N3-[3,5-Dichloro-4-(6-methoxy-pyridin-2-yl)-phenyl]-1H-[1,2,4]triazole-3,5-diamine | 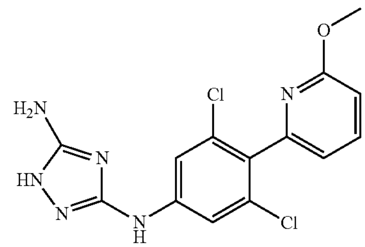 [SMILES: COc1cccc(-c2c(Cl)cc(Nc3n[nH]c(N)n3)cc2Cl)n1] |

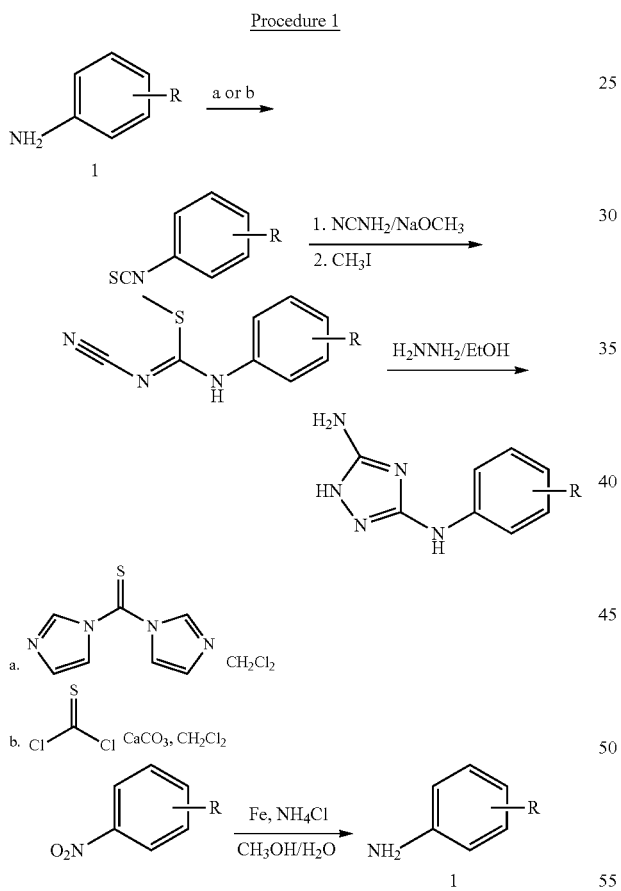
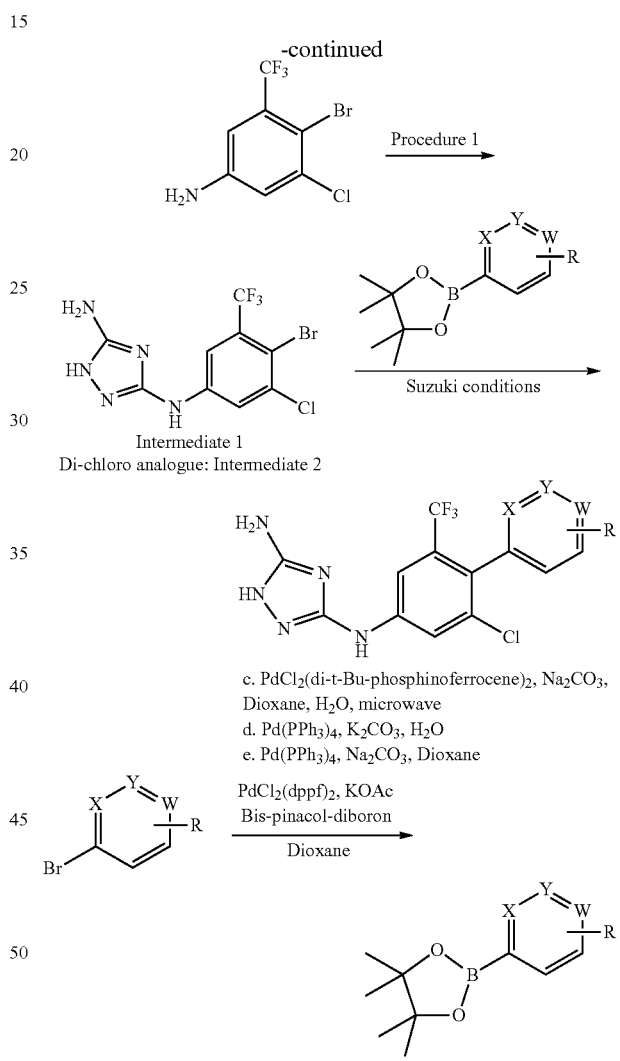

Synthesis

General Schemes

The following schemes depict general methods for obtaining compounds of Formula I.

c. $PdCl_2$(di-t-Bu-phosphinoferrocene)$_2$, $Na_2CO_3$, Dioxane, $H_2O$, microwave
d. Pd(PPh$_3$)$_4$, $K_2CO_3$, $H_2O$
e. Pd(PPh$_3$)$_4$, $Na_2CO_3$, Dioxane Dosage and Administration The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Method of Treatment

Indications

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

Combination Therapy

The compounds of the invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention include, without limitation, all classes of HCV antivirals.

For combination therapies, mechanistic classes of agents that can be useful when combined with the compounds of the invention include, for example, nucleoside and non-nucleoside inhibitors of the HCV polymerase, protease inhibitors, helicase inhibitors, NS4B inhibitors, NS5A inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-9005 18), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-8 13, PHX-1766, PHX2054, IDX-136, IDX-3 16, ABT-450 EP-0 13420 (and congeners) and VBY-376; the Nucleosidic HCV polymerase (replicase) inhibitors useful in the invention include, but are not limited to, R7128, PSI-785 1, IDX-184, IDX-102, R1479, UNX-08 189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nucleosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, compounds of the invention can be used in combination with cyclophyllin and immunophyllin antagonists (e.g., without limitation, DEBIO compounds, NM-811 as well as cyclosporine and its derivatives), kinase inhibitors, inhibitors of heat shock proteins (e.g., HSP90 and HSP70), other immunomodulatory agents that can include, without limitation, interferons (-alpha, -beta, -omega, -gamma, -lambda or synthetic) such as Intron A, Roferon-A, Canferon-A300, Advaferon, Infergen, Humoferon, Sumiferon MP, Alfaferone, IFN-β, Feron and the like; polyethylene glycol derivatized (pegylated) interferon compounds, such as PEG interferon-α-2a (Pegasys), PEG interferon-α-2b (PEGIntron), pegylated IFN-α-con1 and the like; long acting formulations and derivatizations of interferon compounds such as the albumin-fused interferon, Albuferon, Locteron, and the like; interferons with various types of controlled delivery systems (e.g., ITCA-638, omega-interferon delivered by the DUROS subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL, REMICADE, and HUMIRA.

In addition, compounds of the invention can be used in combination with antiprotozoans and other antivirals thought to be effective in the treatment of HCV infection such as, without limitation, the prodrug nitazoxanide. Nitazoxanide can be used as an agent in combination with the compounds disclosed in this invention as well as in combination with other agents useful in treating HCV infection such as peginterferon α-2a and ribavirin.

Compounds of the invention can also be used with alternative forms of interferons and pegylated interferons, ribavirin or its analogs (e.g., tarabavarin, levoviron), microRNA, small interfering RNA compounds (e.g., SIRPLEX-140-N and the like), nucleotide or nucleoside analogs, immunoglobulins, hepatoprotectants, anti-inflammatory agents and other inhibitors of NS5A. Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. Nos. 5,807,876; 6,498,178; 6,344,465; and 6,054,472; PCT Patent Application Publication Nos. WO97/40028; WO98/4038 1; WO00/56331, WO02/04425; WO03/007945; WO03/010141; WO03/000254; WO01/32153; WO00/06529; WO00/18231; WO00/10573; WO00/13708; WO01/85172; WO03/037893; WO03/037894; WO03/

037895; WO02/100851; WO02/100846; WO99/01582; WO00/09543; WO02/18369; WO98/17679, WO00/056331; WO98/22496; WO99/07734; WO05/073216, WO05/073195 and WO08/021927.

Additionally, combinations of, for example, ribavirin and interferon, may be administered as multiple combination therapy with at least one of the compounds of the invention. The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

EXAMPLES

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether ($Et_2O$), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) ($Pd(dppf)Cl_2$), palladium(II) acetate ($Pd(OAc)_2$), tris(dibenzylideneacetone)dipalladium(0) ($Pd_2(dba)_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or Et$_3$N), 2,2,6,6-tetramethylpiperidine 1-oxyl (TEMPO), triflate or $CF_3SO_2$— (TO, trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, Nomenclature in Organic Chemistry, IUPAC 1979 Pergamon Press, Oxford.).

General Conditions

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "Protective Groups in Organic Synthesis" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Preparative Examples

Intermediate 1

Procedure 1

N*3*-(4-Bromo-3-chloro-5-trifluoromethyl-phenyl)-1H-[1,2,4]triazole-3,5-diamine (Intermediate 1)

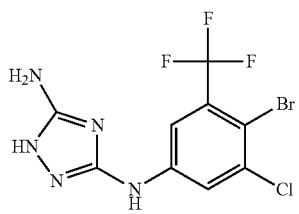 [SMILES: Nc1nc(Nc2cc(Cl)c(Br)c(C(F)(F)F)c2)n[nH]1]

2-bromo-1-chloro-5-isothiocyanato-3-(trifluoromethyl)benzene

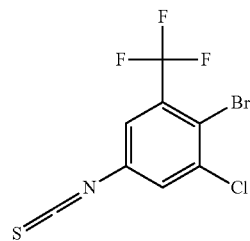 [SMILES: FC(F)(F)c1cc(N=CC=S)cc(Cl)c1Br]

To a suspension of 4-bromo-3-chloro-5-(trifluoromethyl) aniline (15 g, 54.7 mmol, Eq: 1.00) in dichloromethane (13.2 g, 10.0 ml, 155 mmol, Eq: 25.3) at 0, was added 1,1'-thiocarbonyldiimidazole (11.7 g, 65.6 mmol, Eq: 1.2) The reaction was gradually warmed to room temperature and stirred overnight. The reaction was concentrated and chromatographed (220 g Redisep, 5 to 15% dichloromethane/hexane) to give 13.84 g (80%) pale yellow oil.

(Z)-methyl N-4-bromo-3-chloro-5-(trifluoromethyl) phenyl-N'-cyanocarbamimidothioate

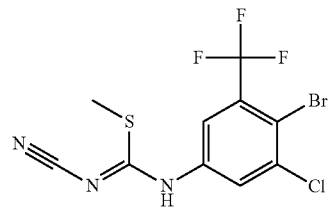 [SMILES: CS/C(=N\C#N)Nc1cc(Cl)c(Br)c(C(F)(F)F)c1]

To a solution of 2-bromo-1-chloro-5-isothiocyanato-3-(trifluoromethyl)benzene (13.84 g, 43.7 mmol, Eq: 1.00) in dimethoxyethane (100 mL) was added sodium hydrogen cyanamide (3.36 g, 52.5 mmol, Eq: 1.2) and methanol (10 mL). After 30 minutes, methyl iodide (15.9 g, 7 ml, 112 mmol, Eq: 2.56) was added to the magenta-colored soln and the reaction was stirred overnight at room temperature. The reaction mixture was concentrated to dryness and dissolved in ~50 mL acetonitrile. Added 100 mL water to give a white precipitate. Filtered white solid, rinsed with water and air-dried o/n to give 16.0 g (99%) of white solid.

N*3*-(4-Bromo-3-chloro-5-trifluoromethyl-phenyl)-1H-[1,2,4]triazole-3,5-diamine (Intermediate 1)

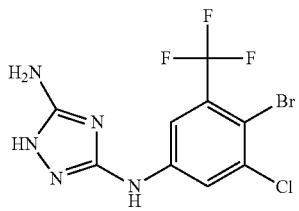

In a 500 mL round-bottomed flask, (Z)-methyl N-4-bromo-3-chloro-5-(trifluoromethyl)phenyl-N'-cyanocarbamimidothioate (1.45 g, 3.89 mmol, Eq: 1.00) was combined with ethanol (15 ml) to give a white suspension. Hydrazine (1.25 g, 1.22 ml, 38.9 mmol, Eq: 10) was added and the reaction mixture was heated to 70° C. and stirred for 3 h. The reaction was cooled and water (~40 mL) was added to the reaction with shaking. The resulting suspension was filtered, washed with water and vacuum oven dried at 45 C over weekend. Obtained a white solid as desired product (1.12 g, 81% yield). Another sample was collected from mother liquor as an pink solid (148 mg, ~90 pure, 9.6% yield)

MS m/z 356 [M+H]

Intermediate 2

Procedure 1

N*3*-(4-Bromo-3,5-dichloro-phenyl)-1H-[1,2,4]triazole-3,5-diamine (Intermediate 2)

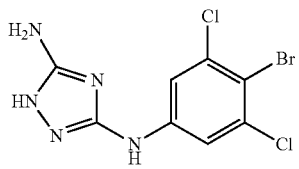

(Z)-methyl N-4-bromo-3,5-dichlorophenyl-N'-cyanocarbamimidothioate

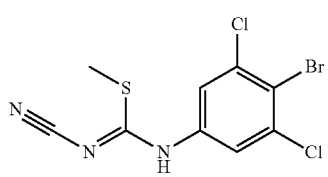 [SMILES: CS/C(=N\C#N)Nc1cc(Cl)c(Br)c(Cl)c1]

A solution of sodium methoxide (2.6 ml, 1.3 mmol, Eq: 1.23) was added to cyanamide (50 mg, 1.19 mmol, Eq: 1.12) and stirred at room temperature for 15 minutes. 2-bromo-1,3-dichloro-5-isothiocyanatobenzene (300 mg, 1.06 mmol, Eq: 1.00) was added to the reaction mixture and stirred for 1 hr. Iodomethane (331 mg, 146 µl, 2.33 mmol, Eq: 2.2) was added and the pale yellow solution was stirred overnight at room temperature. The resulting suspension was filtered and air dried to give 154 mg (43%) of desired product as a light brown solid.

N*3*-(4-Bromo-3,5-dichloro-phenyl)-1H-[1,2,4]triazole-3,5-diamine (Intermediate 2)

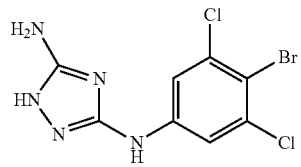 [SMILES: Nc1nc(Nc2cc(Cl)c(Br)c(Cl)c2)n[nH]1]

A solution of (Z)-methyl N-4-bromo-3,5-dichlorophenyl-N'-cyanocarbamimidothioate (154 mg, 454 µmol, Eq: 1.00) and hydrazine (153 mg, 150 µl, 4.78 mmol, Eq: 10.5) in ethanol (5 mL) was heated at 65° C. After 3 hr, LCMS ok, no sm. Cooled to rt and stirred solution over weekend. The reaction mixture was concentrated and chromatographed (11 g Supelco, 0 to 10% MeOH/CH2Cl2) to give 80 mg (55%) of desired product as an off-white solid.

$^1$H NMR (300 MHz, DMSO) □: 11.35 (s, 1H), 9.33 (s, 1H), 7.75 (s, 2H), 6.05 (s, 2H) ppm Intermediate 3

Procedure 1

N$^5$-(4-bromo-3-fluoro-5-trifluoromethylphenyl)-1H-[1,2,4]-triazole-3,5-diamine (Intermediate 3)

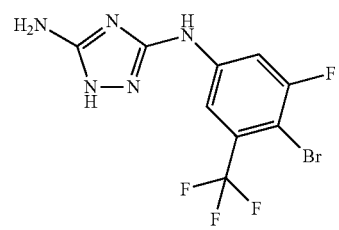 [SMILES: Nc1nc(Nc2cc(F)c(Br)c(C(F)(F)F)c2)n[nH]1]

2-bromo-1-fluoro-5-isothiocyanato-3-trifluoromethylbenzene

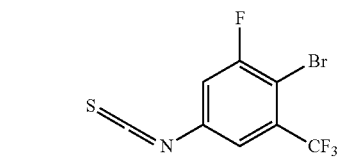

4-bromo-3-fluoro-5-trifluoromethylaniline (4.22 g, 16.4 mmol, Eq: 1.00) and calcium carbonate (3.44 g, 1.17 ml, 34.3 mmol, Eq: 2.1) were suspended in 50% aqueous dichlormethane (20 ml) mixture. The thick suspension was stirred vigorously at 0° C. Thiophosgene (2.07 g, 1.38 ml, 18.0 mmol, Eq: 1.1) was added slowly dropwise to the mixture. After the addition the mixture was stirred at 0° C. for 1.5 hr then stirred overnight at room temperature. The solids were filtered and the filtrate was extracted with dichloromethane. The combined organic phases were washed with water, brine, dried over sodium sulfate and concentrated in vacuo to afford 4.71 g (96%) of the desired material as a light brown solid.

$^1$H NMR (300 MHz, DMSO-d$_6$) □ ppm 7.84 (s, 1H) 7.96 (dd, J=9.06, 2.27 Hz, 1H)

(4-Bromo-3-fluoro-5-trifluoromethyl-phenylamino)-(methyl-□$^4$sulfanylidene)-methyl-cyanamide

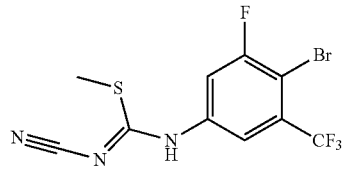 [SMILES: CS/C(=N\C#N)Nc1cc(F)c(Br)c(C(F)(F)F)c1]

2-bromo-1-fluoro-5-isothiocyanato-3-trifluoromethyl-benzene (4.71 g, 15.7 mmol, Eq: 1.00) was dissolved in anhydrous methanol (30 ml). Sodium hydrogencyanamide (1.00 g, 15.7 mmol, Eq: 1) was added and the reaction was stirred for 1 hr at ambient temperature. Methyl iodide (4.46 g, 1.96 ml, 31.4 mmol, Eq: 2) was added dropwise and the reaction was stirred overnight at ambient temperature. The light brown suspension was filtered to afford 1.91 g (34%) of the desired product as a pink solid.

MS+m/z: 357.7. (M+1)
$^1$H NMR (300 MHz, DMSO-d$_6$) □ ppm 2.78 (s, 3H) 7.87 (s, 1H) 7.97 (dd, J=1.00 Hz, 1H) 10.38 (br. s, 1H)

Prepared of N$^5$-(4-bromo-3-fluoro-5-trifluoromethylphenyl)-1H-[1,2,4]-triazole-3,5-diamine (Intermediate 3)

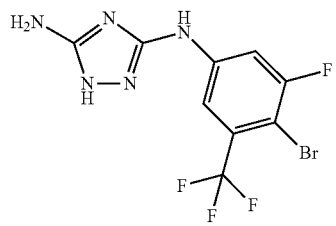 [SMILES: Nc1nc(Nc2cc(F)c(Br)c(C(F)(F)F)c2)n[nH]1]

Hydrazine (1.71 g, 53.4 mmol, Eq: 10) was added to a stirred suspension of (4-Bromo-3-fluoro-5-trifluoromethyl-phenylamino)-(methyl-□$^4$sulfanylidene)-methyl-cyanamide (1.9 g, 5.34 mmol, Eq: 1.00) in ethanol (30 ml). The mixture was heated to 70° C. for 1 hr. The reaction mixture was concentrated to a reduced volume (~5 ml) and water (~10 ml) was added dropwise while stirring. The suspension was stirred for 30 min. The precipitate was filtered and washed with water (~50 ml), then dried under high vacuum at 70° C. for two hours to filtered to afford 1.73 g (95%) of the desired product as a light pink solid.

MS+m/z: 339.9. (M+1)

$^1$H NMR (400 MHz, DMSO-d$_6$) □ ppm 6.03 (s, 2H) 7.81 (s, 1H) 7.86 (d, J=12.13 Hz, 1H) 9.52 (s, 1H) 11.40 (s, 1H)

N*3*-[3,5-Dichloro-4-(6-methoxy-pyridin-3-yl)-phenyl]-1H-[1,2,4]triazole-3,5-diamine (Compound 1)

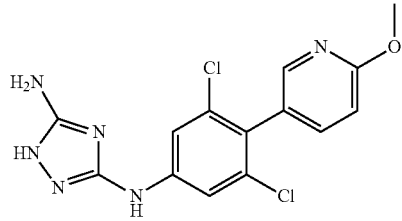

3,5-dichloro-4-(6-methoxypyridin-3-yl)aniline

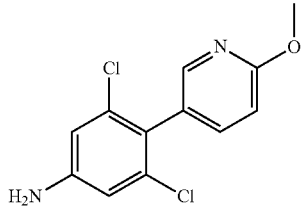 [SMILES: COc1ccc(-c2c(Cl)cc(N)cc2Cl)cn1]

A microwave vial containing 4-bromo-3,5-dichloroaniline (250 mg, 1.04 mmol, Eq: 1.00), 6-methoxypyridin-3-ylboronic acid (206 mg, 1.35 mmol, Eq: 1.3), sodium carbonate (275 mg, 2.59 mmol, Eq: 2.5) and bis(triphenylphosphine)palladium (II) chloride (42.0 mg, 59.8 μmol, Eq: 0.0577) was degassed with Argon for 15 min. Dimethoxyethane (4 mL) and water (1 mL) was added and the reaction was heated for 30 min with the microwave at 115 deg. The reaction mixture was concentrated, diluted with ethyl acetate, and washed with brine. Dried org extract with sodium sulfate and chromatographed (40 g Redisep, 100% hexane to 10% ethyl acetate/hexane) to give 206 mg (74%) of desired product as a colorless oil.

5-(2,6-dichloro-4-isothiocyanatophenyl)-2-methoxypyridine

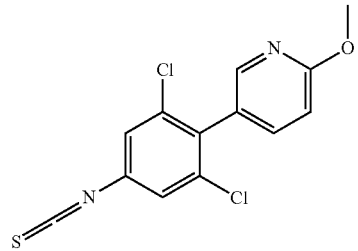 [SMILES: COc1ccc(-c2c(Cl)cc(N=CC=S)cc2Cl)cn1]

To a suspension of calcium carbonate (192 mg, 1.92 mmol, Eq: 2.51) and thiophosgene (105 mg, 70 µl, 913 µmol, Eq: 1.19) in dichloromethane (10.0 ml)/water (10.0 ml) at 0 deg, was added 3,5-dichloro-4-(6-methoxypyridin-3-yl)aniline (206 mg, 765 µmol, Eq: 1.00) The reaction was gradually warmed to room temperature and stirred overnight. Added 24 mL 1N HCl slowly. Separated organic layer and dried over sodium sulfate to give 186 mg (78%) of desired product as a pale yellow oil.

N-((3,5-dichloro-4-(6-methoxypyridin-3-yl)phenylamino)(methylthio)methyl)cyanamide

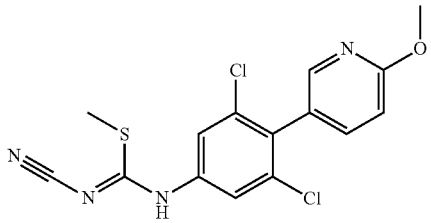 [SMILES: COc1ccc(-c2c(Cl)cc(N/C(=N/C#N)SC)cc2Cl)cn1]

To a solution of 5-(2,6-dichloro-4-isothiocyanatophenyl)-2-methoxypyridine (186 mg, 598 µmol, Eq: 1.00) in MeOH (5 mL) was added to sodium hydrogen cyanamide (48 mg, 750 µmol, Eq: 1.25). After 30 minutes, methyl iodide (170 mg, 75 µl, 1.2 mmol, Eq: 2.01) was added and the reaction was stirred overnight at room temperature. The reaction mixture was concentrated and chromatographed (24 g Redisep, 10 to 40% ethyl acetate/hexane) to give 131 mg (60%) of desired product as a white solid.

N*3*-[3,5-Dichloro-4-(6-methoxy-pyridin-3-yl)-phenyl]-1H-[1,2,4]triazole-3,5-diamine (Compound 1)

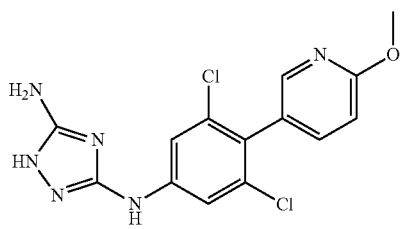 [SMILES: COc1ccc(-c2c(Cl)cc(Nc3n[nH]c(N)n3)cc2Cl)cn1]

To a solution of N-((3,5-dichloro-4-(6-methoxypyridin-3-yl)phenylamino)(methylthio)methyl)cyanamide (131 mg, 355 µmol, Eq: 1.00) in ethanol (5 mL) was added hydrazine (123 mg, 120 µl, 3.82 mmol, Eq: 10.8). The reaction mixture was heated at 60 deg o/n. The resulting suspension was filtered to give 80 mg of desired product as a white solid. The filtrate precipitated over time and was filtered to give an additional 49 mg of white solid, for a total of 129 mg (100%).

MS m/z 351 [M+H]

N*3*-[3,5-Dichloro-4-(5-methanesulfonyl-pyridin-3-yl)-phenyl]-1H-[1,2,4]triazole-3,5-diamine (Compound 2)

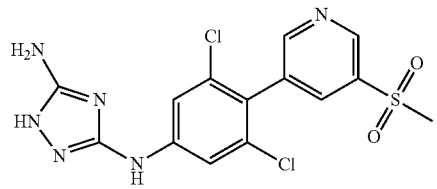 [SMILES: CS(=O)(=O)c1cncc(-c2c(Cl)cc(Nc3n[nH]c(N)n3)cc2Cl)c1]

A microwave vial containing N3-(4-bromo-3,5-dichlorophenyl)-1H-1,2,4-triazole-3,5-diamine Intermediate 2 (100 mg, 310 µmol, Eq: 1.00), 5-(methylsulfonyl)pyridin-3-ylboronic acid (98 mg, 488 µmol, Eq: 1.57), sodium carbonate (85 mg, 802 µmol, Eq: 2.59) and Pd(Ph₃P)₄ (38 mg, 32.9 µmol, Eq: 0.106) was degassed for 15 minutes with Argon. Dioxane (2 mL) and water (0.5 mL) was added, and the suspension was degassed for 5 minutes with sonication, and the reaction was heated at 125° for 1 hr with microwave. The reaction mixture was diluted with ethyl acetate, washed with brine, dried over sodium sulfate, and chromatographed (24 g Supelco, 0 to 10% MeOH/DCM) to give 20 mg of desired product as a yellow solid.

MS m/z 399 [M+H]

5-[4-(5-Amino-1H-[1,2,4]triazol-3-ylamino)-2,6-dichloro-phenyl]-1H-pyridin-2-one (Compound 3)

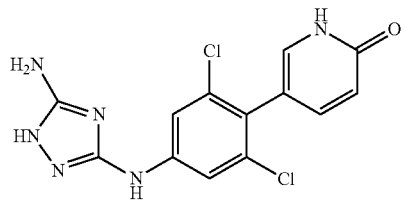 [SMILES: Nc1nc(Nc2cc(Cl)c(-c3ccc(=O)[nH]c3)c(Cl)c2)n[nH]1]

A solution of N3-(3,5-dichloro-4-(6-methoxypyridin-3-yl)phenyl)-1H-1,2,4-triazole-3,5-diamine Compound 1 (95 mg, 271 µmol, Eq: 1.00) and HBr (231 mg, 155 µl, 1.37 mmol, Eq: 5.06) in AcOH (5 mL) was heated at 100 deg for 2 days in a sealed tube. The reaction mixture was carefully poured into ice NaHCO₃, extracted with ethyl acetate, and dried with sodium sulfate to give 42 mg (46%) of desired product as an off-white solid.

MS m/z 337 [M+H]

N*3*-[4-(6-Amino-pyridin-3-yl)-3,5-dichloro-phenyl]-1H-[1,2,4]triazole-3,5-diamine (Compound 4)

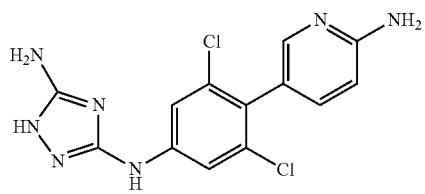 [SMILES: Nc1ccc(-c2c(Cl)cc(Nc3n[nH]c(N)n3)cc2Cl)cn1]

A microwave vial containing N3-(4-bromo-3,5-dichlorophenyl)-1H-1,2,4-triazole-3,5-diamine Intermediate 2 (100 mg, 310 μmol, Eq: 1.00), 5-(4,4,5,5-tetramethyl-1,3,2-dioxaborolan-2-yl)pyridin-2-amine (104 mg, 473 μmol, Eq: 1.53), sodium carbonate (92 mg, 868 μmol, Eq: 2.8) and Pd(Ph$_3$P)$_4$ (58 mg, 50.2 μmol, Eq: 0.162) was degassed for 15 minutes with Argon. Dioxane (2 mL) and water (0.5 mL) was added, and the suspension was degassed for 5 minutes with sonication, and the reaction was heated at 125° for 1 hr with microwave. The reaction was concentrated, diluted with ethyl acetate, washed with brine, dried with sodium sulfate, and purified by preparative plate chromatography (10% MeOH/DCM) to give 26 mg (25%) of desired product as a light yellow solid.

MS m/z 336 [M+H]

N*3*-[4-(2-Amino-pyrimidin-5-yl)-3,5-dichlorophenyl]-1H-[1,2,4]triazole-3,5-diamine (Compound 5)

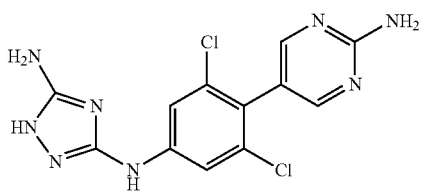 [SMILES: Nc1ncc(-c2c(Cl)cc(Nc3n[nH]c(N)n3)cc2Cl)cn1]

A microwave vial containing N3-(4-bromo-3,5-dichlorophenyl)-1H-1,2,4-triazole-3,5-diamine Intermediate 2 (100 mg, 310 μmol, Eq: 1.00), 5-(4,4,5,5-tetramethyl-1,3,2-dioxaborolan-2-yl)pyrimidin-2-amine (108 mg, 489 μmol, Eq: 1.58), sodium carbonate (88 mg, 830 μmol, Eq: 2.68) and Pd(Ph$_3$P)$_4$ (49 mg, 42.4 μmol, Eq: 0.137) was degassed for 15 minutes with Argon. Dioxane (2 mL) and water (0.5 mL) was added, and the suspension was degassed for 5 minutes with sonication, and the reaction was heated at 125° for 1.5 hr with microwave. The reaction mixture was concentrated, diluted with ethyl acetate, washed with brine, dried with sodium sulfate, and chromatographed (11 g Supelco, 0 to 10% MeOH/DCM) to give 9.5 mg (9%) of desired product as a light yellow solid.

MS m/z 337 [M+H]

N3-(3,5-dichloro-4-(2-methoxypyridin-4-yl)phenyl)-1H-1,2,4-triazole-3,5-diamine (Compound 6)

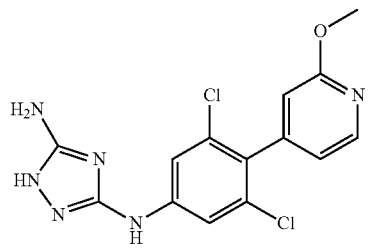 [SMILES: COc1cc(-c2c(Cl)cc(Nc3n[nH]c(N)n3)cc2Cl)ccn1]

To a solution of N-((3,5-dichloro-4-(2-methoxypyridin-4-yl)phenylamino)(methylthio)methyl)cyanamide (192 mg, 520 μmol, Eq: 1.00) in ethanol (7 mL) was added hydrazine (184 mg, 180 μl, 5.74 mmol, Eq: 11.0). The reaction mixture was heated at 60 deg o/n. The reaction was concentrated and chromatographed (23 g Supelco, 0 to 10% MeOH/DCM) to give 126 mg (69%) of desired product as a white solid.

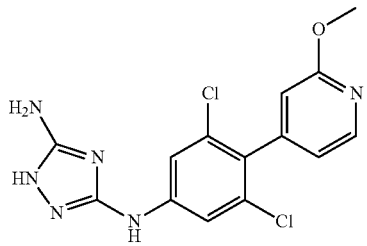 [SMILES: COc1cc(-c2c(Cl)cc(Nc3n[nH]c(N)n3)cc2Cl)ccn1]

3,5-dichloro-4-(2-methoxypyridin-4-yl)aniline

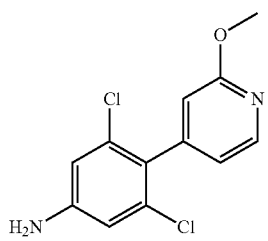 [SMILES: COc1cc(-c2c(Cl)cc(N)cc2Cl)ccn1]

A microwave vial containing 4-bromo-3,5-dichloroaniline (350 mg, 1.45 mmol, Eq: 1.00), 2-methoxypyridin-4-ylboronic acid (289 mg, 1.89 mmol, Eq: 1.3), sodium carbonate (394 mg, 3.72 mmol, Eq: 2.56) and bis(triphenylphosphine)palladium (II) chloride (65 mg, 92.6 μmol, Eq: 0.0637) was degassed with Argon for 15 min. DME (8 mL) and water (2 mL) was added and the reaction was heated for 30 min with the microwave at 115 deg. The reaction mixture was concentrated, diluted with ethyl acetate, washed with brine, dried with sodium sulfate and chromatographed (40 g Redisep, 100% to 10% ethyl acetate/hexane) to give 254 mg (65%) of desired product as a colorless oil.

4-(2,6-dichloro-4-isothiocyanatophenyl)-2-methoxypyridine

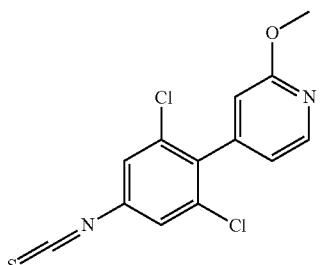

To a suspension of calcium carbonate (264 mg, 2.64 mmol, Eq: 2.79) and thiophosgene (135 mg, 90 μl, 1.17 mmol, Eq: 1.24) in dichloromethane (10.0 mL)/water (10.0 mL) at 0 deg, was added 3,5-dichloro-4-(2-methoxypyridin-4-yl)aniline (254 mg, 944 μmol, Eq: 1.00) The reaction was gradually warmed to room temperature and stirred overnight. Added 2.5 mL 1N HCl slowly. Separated organic layer and dried over sodium sulfate to give 240 mg (82%) of desired product as a light yellow oil.

N-((3,5-dichloro-4-(2-methoxypyridin-4-yl)phenylamino)(methylthio)methyl)cyanamide

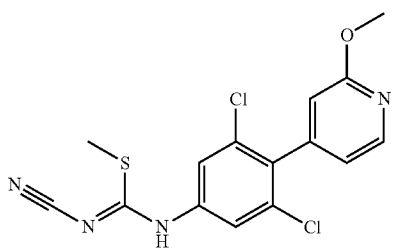 [SMILES: COc1cc(-c2c(Cl)cc(N/C(=N/C#N)SC)cc2Cl)ccn1]

To a solution of 4-(2,6-dichloro-4-isothiocyanatophenyl)-2-methoxypyridine (240 mg, 771 μmol, Eq: 1.00) in MeOH (6 mL) was added to sodium hydrogen cyanamide (61.9 mg, 967 μmol, Eq: 1.25). After 30 minutes, methyl iodide (227 mg, 100 μl, 1.6 mmol, Eq: 2.07) was added and the reaction was stirred overnight at room temperature. The resulting suspension was filtered to give 94 mg of desired product as a white solid. The filtrate was concentrated and chromatographed (24 g Redisep, 10 to 40% ethyl acetate/hexane) to give an additional 98 mg of desired product as an off-white solid, for a total of 192 mg (68%) of product.

N3-(3,5-dichloro-4-(2-methoxypyridin-4-yl)phenyl)-1H-1,2,4-triazole-3,5-diamine (Compound 6)

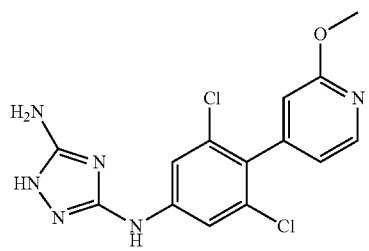 [SMILES: COc1cc(-c2c(Cl)cc(Nc3n[nH]c(N)n3)cc2Cl)ccn1]

To a solution of N-((3,5-dichloro-4-(2-methoxypyridin-4-yl)phenylamino)(methylthio)methyl)cyanamide (192 mg, 520 μmol, Eq: 1.00) in ethanol (7 mL) was added hydrazine (184 mg, 180 μl, 5.74 mmol, Eq: 11.0). The reaction mixture was heated at 60 deg o/n. The reaction was concentrated and chromatographed (23 g Supelco, 0 to 10% MeOH/DCM) to give 126 mg (69%) of desired product as a white solid.
MS m/z 352 [M+H]

4-[4-(5-Amino-1H-[1,2,4]triazol-3-ylamino)-2,6-dichloro-phenyl]-1H-pyridin-2-one (Compound 7)

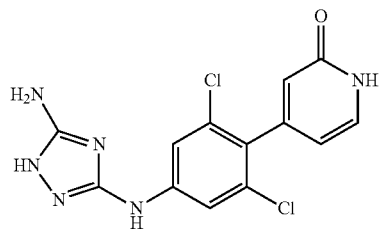 [SMILES: Nc1nc(Nc2cc(Cl)c(-c3cc[nH]c(=O)c3)c(Cl)c2)n[nH]1]

5/9 10 am A solution of N3-(3,5-dichloro-4-(2-methoxypyridin-4-yl)phenyl)-1H-1,2,4-triazole-3,5-diamine Compound 6 (126 mg, 359 μmol, Eq: 1.00) and HBr (298 mg, 200 μl, 1.77 mmol, Eq: 4.93) in AcOH (5 mL) was heated at 100 deg for 2 d in a sealed tube. The reaction mixture was carefully poured into ice NaHCO₃, extracted with ethyl acetate, dried with sodium sulfate to give 64 mg (53%) of desired product as an off-white solid.
MS m/z 337 [M+H]

N-{5-[4-(5-Amino-1H-[1,2,4]triazol-3-ylamino)-2,6-dichloro-phenyl]-pyridin-2-yl}-methanesulfonamide (Compound 8)

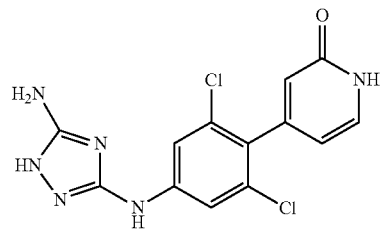 [SMILES: Nc1nc(Nc2cc(Cl)c(-c3cc[nH]c(=O)c3)c(Cl)c2)n[nH]1]

N-(5-(4,4,5,5-tetramethyl-1,3,2-dioxaborolan-2-yl)pyridin-2-yl)methanesulfonamide

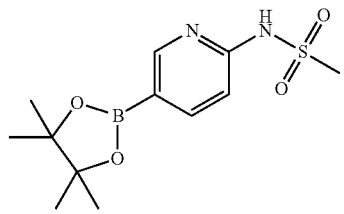

To a solution of 5-(4,4,5,5-tetramethyl-1,3,2-dioxaborolan-2-yl)pyridin-2-amine (500 mg, 2.27 mmol, Eq: 1.00) and pyridine (538 mg, 550 μl, 6.8 mmol, Eq: 2.99) in DCM (10 mL) at 0 deg, was added Ms-Cl (323 mg, 220 μl, 2.82 mmol, Eq: 1.24). The reaction mixture was gradually warmed to room temperature and stirred overnight. The reaction mixture was diluted with DCM, washed with 1N HCl, and dried over sodium sulfate to give 118 mg (17%) of white solid, containing desired product and impurities.

N-{5-[4-(5-Amino-1H-[1,2,4]triazol-3-ylamino)-2,6-dichloro-phenyl]-pyridin-2-yl}-methanesulfonamide

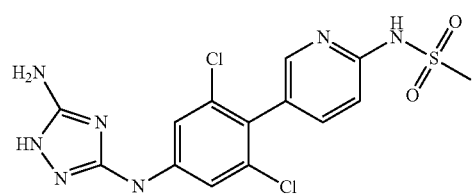

A microwave vial containing N3-(4-bromo-3,5-dichlorophenyl)-1H-1,2,4-triazole-3,5-diamine Compound 7 (100 mg, 310 µmol, Eq: 1.00), N-(5-(4,4,5,5-tetramethyl-1,3,2-dioxaborolan-2-yl)pyridin-2-yl)methanesulfonamide (118 mg, 396 µmol, Eq: 1.28), sodium carbonate (82.0 mg, 774 µmol, Eq: 2.5) and Pd(Ph$_3$P)$_4$ (42 mg, 36.3 µmol, Eq: 0.117) was degassed for 15 minutes with Argon. Dioxane (2 mL) and water (0.5 mL) was added, and the suspension was degassed for 5 minutes with sonication, and the reaction was heated at 125° for 1.5 hr with microwave.

The reaction mixture was concentrated, diluted with ethyl acetate, washed with brine, dried with sodium sulfate, and chromatographed (24 g Redisep, 0 to 10% MeOH/DCM) to give a brown solid containing product and impurities. The solid was triturated with MeOH/DCM to give 30 mg (24%) of desired product as a light brown solid.

MS m/z 414 [M+H]

N$^5$-(3-Fluoro-4-(6-fluoropyridin-3-yl)-5-trifluoromethylphenyl)-1H-[1,2,4]-triazole-3,5-diamine (Compound 9)

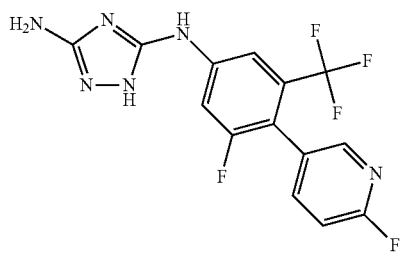 [SMILES: Nc1n[nH]c(Nc2cc(F)c(-c3ccc(F)nc3)c(C(F)(F)F)c2)n1]

To a 15 mL microwave vial was added N$^5$-(4-bromo-3-fluoro-5-trifluoromethylphenyl)-1H-[1,2,4]-triazole-3,5-diamine Intermediate 3 (50 mg, 147 µmol, Eq: 1.00), 6-fluoropyridin-3-ylboronic acid (31.1 mg, 221 µmol, Eq: 1.5) and sodium hydroxide (735 µl, 735 µmol, Eq: 5) in DME (1.5 ml). Pd(Ph$_3$P)$_4$ (8.49 mg, 7.35 µmol, Eq: 0.05) was added, the mixture was purged with argon, the vial was capped and heated in the microwave at 120° C. for 30 minutes. The reaction mixture was diluted with dichloromethane, filtered through celite and concentrated in vacuo. The residue was taken up in MeOH, filtered through a 4 micron filter and the crude material was purified by preparative HPLC (20% ACN: 0.3% TFA in water to 100% ACN) to afford 11 mg (20%) of the desired product as a white solid.

MS+m/z: 357.0. (M+1)

N$^5$-(3-Fluoro-4-(pyridin-3-yl)-5-trifluoromethylphenyl)-1H-[1,2,4]-triazole-3,5-diamine (Compound 10)

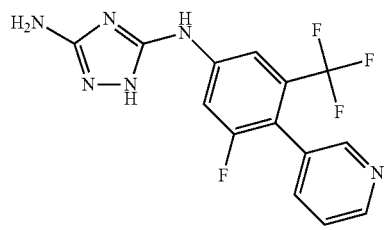 [SMILES: Nc1n[nH]c(Nc2cc(F)c(-c3cccnc3)c(C(F)(F)F)c2)n1]

Prepared by a similar procedure to Compound 8, except substituted pyridine-3-boronic acid for 6-fluoropyridin-3-ylboronic acid to afford 5 mg (7%) of the desired material as a white solid.

MS+m/z: 339.0. (M+1)

N$^5$-(3,5-Dichloro-4-(6-methanesulfonyl-pyridin-3-yl)-phenyl)-1H-[1,2,4]-triazole-3,5-diamine (Compound 11)

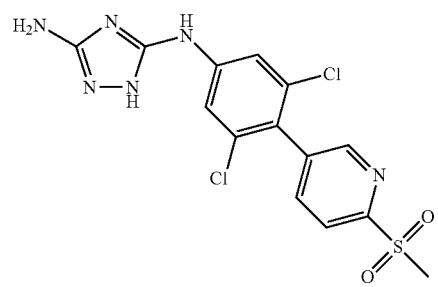 [SMILES: CS(=O)(=O)c1ccc(-c2c(Cl)cc(Nc3nc(N)n[nH]3)cc2Cl)cn1]

To a 15 mL microwave vial was added N3-(4-bromo-3,5-dichlorophenyl)-1H-1,2,4-triazole-3,5-diamine Intermediate 2 (201 mg, 622 µmol, Eq: 1.00), 6-(methylsulfonyl)pyridin-3-ylboronic acid (125 mg, 622 µmol, Eq: 1.00) and Cs$_2$CO$_3$ (608 mg, 1.87 mmol, Eq: 3) in n-butanol (3.00 ml) and water (600 µl). PdCl$_2$(DPPF) (50.8 mg, 62.2 µmol, Eq: 0.1) was added, the mixture was purged with argon, the vial was capped and heated in the microwave at 135° C. for 30 minutes. The mixture was diluted with dichloromethane, added Na$_2$SO$_4$ and filtered through celite. The filtrate was taken up in methanol, filtered and concentrated. The crude material was purified by preparative HPLC (0.1% TFA in water/0.1% TFA in AcCN). 95% to 10% over 25 minutes to afford 13 mg (5%) of the desired material as a white solid.

MS+m/z: 398.9/400.8. (M+1)

6-[4-(5-Amino-2H-[1,2,4]triazol-3-ylamino)-2,6-dichlorophenyl]-2,6-diaza-spiro[3.3]heptane-2-carboxylic acid tert-butyl ester (Compound 12)

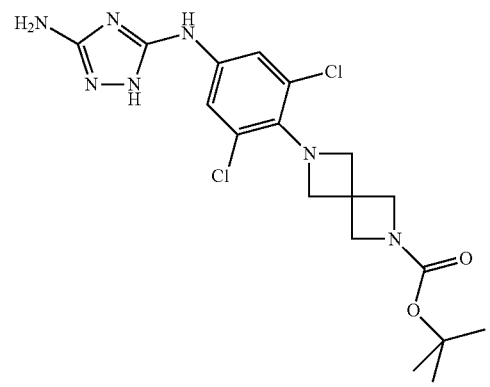 [SMILES: CC(C)(C)OC(=O)N1CC2(C1)CN(c1c(Cl)cc(Nc3nc(N)n[nH]3)cc1Cl)C2]

6-(2,6-Dichloro-4-nitrophenyl]-2,6-diaza-spiro[3.3]heptane-2-carboxylic acid tert-butyl ester

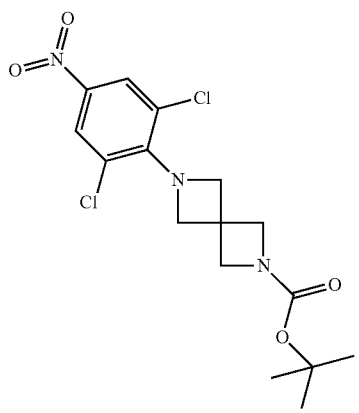 [SMILES: CC(C)(C)OC(=O)N1CC2(C1)CN(c1c(Cl)cc([N+](=O)[O-])cc1Cl)C2]

In a 50 ml round-bottomed flask, 1,3-dichloro-2-fluoro-5-nitrobenzene (467 mg, 2.22 mmol, Eq: 1.00), tert-butyl 2,6-diazaspiro[3.3]heptane-2-carboxylate (529 mg, 2.67 mmol, Eq: 1.2) and $Cs_2CO_3$ (1.81 g, 5.56 mmol, Eq: 2.5) were combined with DMF (10 ml) to give a yellow suspension. The mixture was heated to 90° C. and stirred under argon for 18 hours. TLC indicated total conversion. Cooled and the reaction mixture was diluted with $H_2O$ and EtOAc. The aqueous layer was washed with EtOAc (2×40 ml). The organic layers were combined, washed with $H_2O$ (2×25 mL), brine (1×25 mL), dried over $Na_2SO_4$ and concentrated in vacuo to afford the desired product in quantitative yield as a bright yellow powder.

MS −m/z: 386.9/389.0. (M−1)

6-(4-Amino-2,6-dichlorophenyl]-2,6-diaza-spiro[3.3]heptane-2-carboxylic acid tert-butyl ester

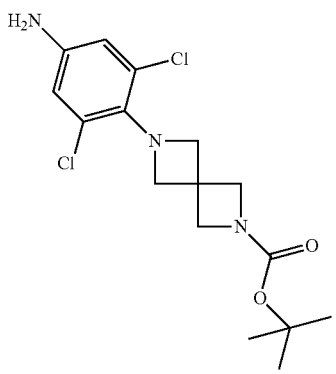 [SMILES: CC(C)(C)OC(=O)N1CC2(C1)CN(c1c(Cl)cc(N)cc1Cl)C2]

In a 50 mL round-bottomed flask, tert-butyl 6-(2,6-dichloro-4-nitrophenyl)-2,6-diazaspiro[3.3]heptane-2-carboxylate (700 mg, 1.8 mmol, Eq: 1.00) and ammonium formate (955 mg, 15.1 mmol, Eq: 8.4) were combined with methanol (100 ml) and water (15 ml) to give a yellow suspension. Zinc (495 mg, 7.57 mmol, Eq: 4.2) was added and the suspension was stirred at 25° C. for 18 hours. Additional ammonium formate (1.02 g, 16.2 mmol, Eq: 9) and zinc (472 mg, 7.21 mmol, Eq: 4) were added with methanol (50 ml) and water (10 ml) and the yellow suspension was stirred at 25° C. for 5 hours. The reaction mixture was filtered and the filter cake was washed with methanol. The filtrate was concentrated in vacuo. The crude material was triturated with hot EtOAc, filtered and stripped. The dark yellow filtrate was stripped in vacuo and the crude material was purified by flash chromatography (silica gel, 80 g, 0% to 30% EtOAc in heptane). The dark yellow oil was dried under vacuum at 25 C overnight to afford 399 mg (62%) the desired product as a yellow crystalline solid.

MS+m/z: 358/360. (M+1)

6-(2,6-Dichloro-4-isothiocyanato-phenyl]-2,6-diaza-spiro[3.3]heptane-2-carboxylic acid tert-butyl ester

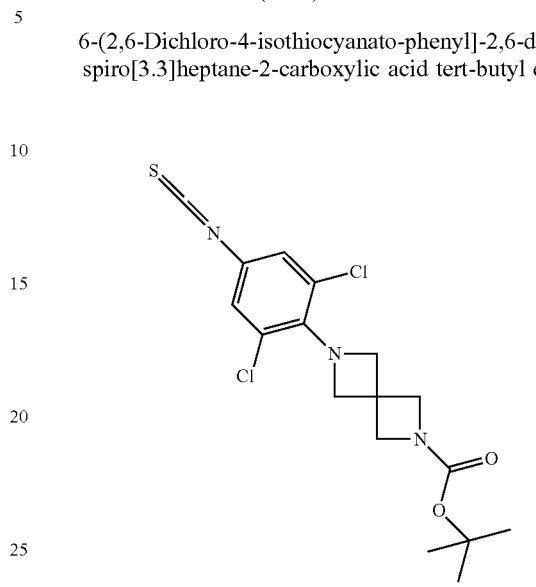

Tert-butyl 6-(4-amino-2,6-dichlorophenyl)-2,6-diazaspiro[3.3]heptane-2-carboxylate (137 mg, 382 µmol, Eq: 1.00) and calcium carbonate (80.4 mg, 803 µmol, Eq: 2.1) were suspended in a 50% aqueous dichloromethane (3 ml). Thiophosgene (48.4 mg, 32.2 µL, 421 µmol, Eq: 1.1) was added dropwise to the mixture at 25° C. After the addition the mixture was stirred at 25° C. for 22 hours. The reaction was filtered and the filter cake was washed with dichloromethane. The filtrate was separated and the aqueous layer extracted with dichloromethane. The organic layers were dried over $Na_2SO_4$ and concentrated in vacuo to give a yellow crystalline solid. The crude material was used without any further purification.

tert-butyl 6-(2,6-dichloro-4-(cyanamido(methylthio)methyleneamino)phenyl)-2,6-diazaspiro[3.3]heptane-2-carboxylate

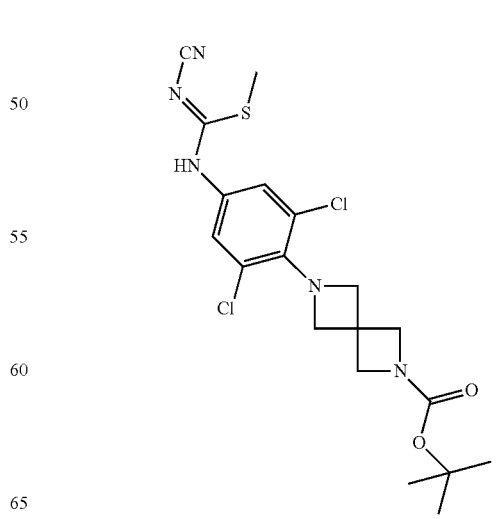

In a 250 mL round-bottomed flask, tert-butyl 6-(2,6-dichloro-4-isothiocyanatophenyl)-2,6-diazaspiro[3.3]heptane-2-carboxylate (153 mg, 382 μmol, Eq: 1.00) was combined with methanol (2 ml) to give an yellow suspension. Sodium cyanamide (26.9 mg, 420 μmol, Eq: 1.1) was added and the reaction was stirred at 25° C. for 1.5 hour under argon. Methyl iodide (65.1 mg, 28.7 μl, 459 μmol, Eq: 1.2) was added and the reaction mixture was stirred at 25° C. for 17 hours under argon. The reaction mixture was concentrated in vacuo and used without any further purification.

MS+m/z: 457/459. (M+1)

6-[4-(5-Amino-2H-[1,2,4]triazol-3-ylamino)-2,6-dichlorophenyl]-2,6-diaza-spiro[3.3]heptane-2-carboxylic acid tert-butyl ester (Compound 12)

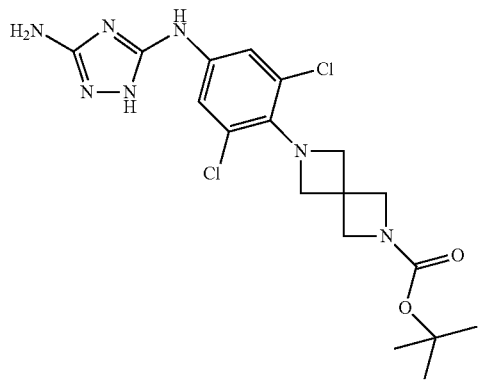 [SMILES: CC(C)(C)OC(=O)N1CC2(C1)CN(c1c(Cl)cc(Nc3nc(N)n[nH]3)cc1Cl)C2]

In a 50 mL round-bottomed flask, tert-butyl 6-(2,6-dichloro-4-(cyanamido(methylthio)methyleneamino) phenyl)-2,6-diazaspiro[3.3]heptane-2-carboxylate (174 mg, 381 μmol, Eq: 1.00) was combined with ethanol (3 ml) to give a yellow solution. Hydrazine monohydrate (191 mg, 185 μl, 3.81 mmol, Eq: 10) was added and the reaction mixture was heated to 70° C. and stirred for 1.5 hour. The crude reaction mixture was concentrated in vacuo and the residue was diluted with water and stirred overnight. The solid was filtered triturated with MeOH. The suspension was filtered and the filtrate was concentrated. The crude material was purified by preparative HPLC (0.1% TFA in water/0.1% TFA in AcCN). 95% to 10% over 25 mins. The clean fractions were pooled, basified with 3 drops of 1M NaOH and stripped in vacuo to give a white powder. The powder was filtered and washed with water to remove salts. The clean product was dried under vacuum at 45° C. overnight to afford 13.5 mg (8%) of the desired product as a white solid.

MS+m/z: 440.0/441.9. (M+1)

{3-Aminomethyl-1-[4-(5-amino-2H-[1,2,4]triazol-3-ylamino)-2,6-dichlorophenyl]-azetidin-3-yl}-methanol (Compound 13)

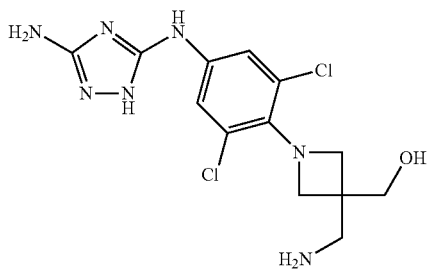 [SMILES: NCC1(CO)CN(c2c(Cl)cc(Nc3nc(N)n[nH]3)cc2Cl)C1]

In a 100 mL round-bottomed flask, tert-butyl 6-(4-(5-amino-1H-1,2,4-triazol-3-ylamino)-2,6-dichlorophenyl)-2,6-diazaspiro[3.3]heptane-2-carboxylate Compound 11 (21 mg, 47.7 μmol, Eq: 1.00) was combined with dichloromethane (2 ml) methanol (0.5 ml) and TFA (1.5 ml) to give a pink solution. The reaction was stirred at 25° C. for 3 days. The reaction was concentrated in vacuo and the residue was purified by preparative HPLC (0.1% TFA in water/0.1% TFA in AcCN). 95% to 10% over 16 mins. The colorless glass was dried under vacuum at 45° C. to afford 2.3 mg (14%) of the desired product as a white solid.

MS −m/z: 356/358 (M−1)

N3-(3-chloro-4-(pyridazin-3-yl)phenyl)-1H-1,2,4-triazole-3,5-diamine (Compound 14)

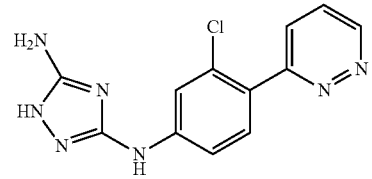 [SMILES: Nc1nc(Nc2ccc(-c3cccnn3)c(Cl)c2)n[nH]1]

3-Chloro-4-pyridazin-3-yl-phenylamine

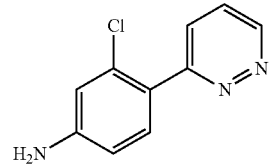 [SMILES: Nc1ccc(-c2cccnn2)c(Cl)c1]

In a 250 mL round-bottomed flask, 3-chloro-4-(4,4,5,5-tetramethyl-1,3,2-dioxaborolan-2-yl)aniline (950 mg, 3.75 mmol, Eq: 1.00), 3-chloropyridazine (437 mg, 3.82 mmol, Eq: 1.02) and tetrakis(triphenylphosphine)palladium(0) (437 mg, 378 μmol, Eq: 0.101) were combined with toluene (38.0 mL) to give a brown solution. A 2.0 M aqueous solution of sodium carbonate (7.6 ml, 15.2 mmol, Eq: 4.06) and ethanol (7.6 mL) were added. The reaction mixture was stirred at 115° C. for 5 hours.

The reaction mixture was cooled to room temperature, and it was stirred at room temperature overnight. The reaction mixture was partitioned between ethyl acetate (10 mL) and water (10 mL). The organic phase was dried (Na$_2$SO$_4$), filtered, then concentrated over silica gel. The silica-supported crude product was loaded onto a 115 gram silica gel column (Analogix). Flash chromatography (70% ethyl acetate in hexanes) gave 3-chloro-4-pyridazin-3-yl-phenylamine (700 mg, 90%) containing triphenylphosphine oxide as a minor impurity.

3-(2-Chloro-4-isothiocyanato-phenyl)-pyridazine

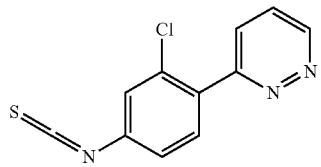 [SMILES: S=CC=Nc1ccc(-c2cccnn2)c(Cl)c1]

In a 1 L round-bottomed flask, 3-chloro-4-(pyridazin-3-yl)aniline (0.7 g, 3.4 mmol, Eq: 1.00) and 1,1'-thiocarbonyldiimidazole (700 mg, 3.93 mmol, Eq: 1.15) were combined with methylene chloride (20 mL) to give a brown solution. This mixture was stirred at room temperature over 22 hours. The reaction mixture was concentrated over silical gel. The silica-supported crude product was loaded onto a 115 g Analogix column. Flash chromatography (50% ethyl acetate-hexanes) provided 3-(2-chloro-4-isothiocyanato-phenyl)-pyridazine (400 mg, 47%) as a white crystalline solid.

(Z)-Methyl N-3-chloro-4-(pyridazin-3-yl)phenyl-N'-cyanocarbamimidothioate

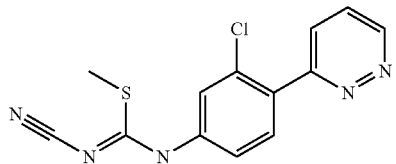

In a 50 mL pear-shaped flask, cyanamide (204 mg, 4.84 mmol, Eq: 3.0) and a 0.5 M solution of sodium methoxide in methanol (4.84 mL, 2.42 mmol, Eq: 1.5) were combined with methanol (6.5 mL) to give a colorless solution. This mixture was stirred at room temperature for 15 minutes. After this time, the mixture was added dropwise to a suspension of 3-(2-chloro-4-isothiocyanatophenyl)pyridazine (400 mg, 1.61 mmol, Eq: 1.00) and 6.5 mL methanol. Upon addition of the cyanamide-sodium methoxide mixture, the suspension quickly became a slightly yellow solution. This mixture was stirred at room temperature for 1 hour. After this time, iodomethane (344 mg, 151 µl, 2.42 mmol, Eq: 1.5) was added. The reaction mixture was stirred at room temperature overnight. In the morning, a yellow precipitate was present. The reaction mixture was filtered, and the collected solids were washed with a minimal amount of methanol. After further drying on the buchner funnel, this product was collected. A second crop was obtained when the mother liquor yielded a yellow precipitate. The two products were combined to give (Z)-methyl N-3-chloro-4-(pyridazin-3-yl)phenyl-N'-cyanocarbamimidothioate (229 mg, 46%) as a yellow powder.

N3-(3-chloro-4-(pyridazin-3-yl)phenyl)-1H-1,2,4-triazole-3,5-diamine (Compound 14)

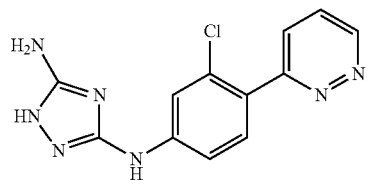 [SMILES: Nc1nc(Nc2ccc(-c3cccnn3)c(Cl)c2)n[nH]1]

In a 50 mL round-bottomed flask, (Z)-methyl N-3-chloro-4-(pyridazin-3-yl)phenyl-N'-cyanocarbamimidothioate (229 mg, 754 µmol, Eq: 1.00) and hydrazine (245 mg, 240 µl, 7.64 mmol, Eq: 10.1) were combined with ethanol (7.5 ml) to give a yellow suspension. After stirring for about ten minutes, nearly all of the starting material dissolved to give a yellow solution. The reaction mixture was heated at 85° C. After only 15 minutes heating, the reaction mixture was again a yellow suspension. The reaction was heated at 85° C. for a total of 5 hours. The reaction mixture was cooled to room temperature, and the precipitate was collected using vacuum filtration to provide N3-(3-chloro-4-(pyridazin-3-yl)phenyl)-1H-1,2,4-triazole-3,5-diamine (153 mg, 71%) as a yellow powder. MS cald. for $C_{12}H_{10}ClN_7$ [(M+H)]: 288, obsd. 288.0.

N3-(3-Chloro-4-(1-methyl-1H-tetrazol-5-yl)phenyl)-1H-1,2,4-triazole-3,5-diamine (Compound 15)

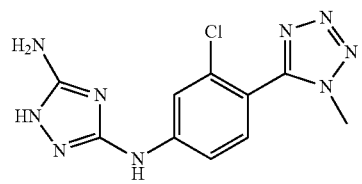 [SMILES: Cn1nnnc1-c1ccc(Nc2n[nH]c(N)n2)cc1Cl]

2-Chloro-N-methyl-4-nitro-benzamide

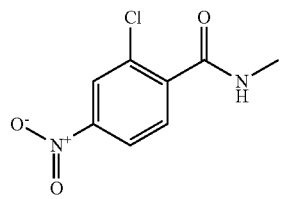

In a 500 mL round-bottomed flask, 2-chloro-4-nitrobenzoic acid (5.0 g, 24.8 mmol, Eq: 1.00) and thionyl chloride (40.8 g, 25 ml, 343 mmol, Eq: 13.8) were combined to give a white suspension. This mixture was refluxed neat for 4 hours. After this time, the reaction mixture was concentrated on the rotary evaporator. The crude product was combined with 45 mL methylene chloride and cooled to 0° C. using an ice-water bath. Methylamine hydrochloride (2.01 g, 29.8 mmol) was added followed by N,N-diisopropylethylamine (8.66 mL, 49.6 mmol). The reaction mixture was stirred and warmed to room temperature as the ice bath gradually melted. The reaction mixture was stirred over night for 16 hours. After this time, the reaction mixture was washed with water then brine. The organic phase was dried over MgSO₄, filtered, and concentrated to afford 2-chloro-N-methyl-4-nitro-benzamide (258 mg, 63%) as a yellow solid. The crude product was used in the next step without further purification.

5-(2-Chloro-4-nitro-phenyl)-1-methyl-1H-tetrazole

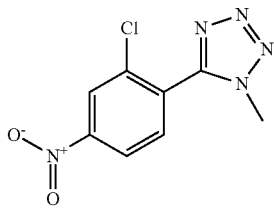 [SMILES: Cn1nnnc1-c1ccc([N+](=O)[O-])cc1Cl]

In a 500 mL round-bottomed flask, 2-chloro-N-methyl-4-nitro-benzamide (6.31 g, 29.4 mmol) and thionyl chloride (5.25 g, 3.22 ml, 44.1 mmol, Eq: 1.5) were combined with toluene (200 mL). The resultant mixture was refluxed overnight. In the morning, the mixture was cooled to room temperature, and the mixture was stirred at room temperature over the weekend. The reaction mixture was concentrated on the rotary evaporator. The crude residue was then combined with 20 mL additional toluene, and concentrated again. A mixture of the crude product from above and 40 mL acetonitrile was added to a 0° C. mixture of azidotrimethylsilane (5.44 ml, 41.2 mmol, Eq: 1.4) in acetonitrile (80 mL). The reaction mixture was stirred at 0° C. for 2 hours, and then warmed to room temperature. The reaction mixture was stirred at room temperature overnight. The reaction mixture was concentrated, and the residue was partitioned between methylene chloride and water. The organic phase was washed with brine, dried over MgSO₄, filtered, and concentrated over silica gel. The silica gel supported crude product was loaded onto a 220 gram analogix column. Flash chromatography (45% ethyl acetate-hexanes) provided 5-(2-chloro-4-nitro-phenyl)-1-methyl-1H-tetrazole (4.14 g, 59%) as a yellow, crystalline solid.

3-Chloro-4-(1-methyl-1H-tetrazol-5-yl)-phenylamine

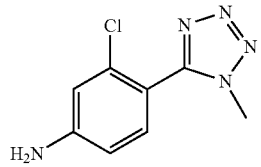

In a 100 mL round-bottomed flask, 5-(2-chloro-4-nitrophenyl)-1-methyl-1H-tetrazole (0.6 g, 2.5 mmol, Eq: 1.00), iron (700 mg, 12.5 mmol, Eq: 5.01) and ammonium chloride (1.34 g, 25.0 mmol, Eq: 10.00) were combined with methanol (6.7 ml) to give a grey suspension. Water (3.3 mL) was added. The reaction mixture was heated at 75° C. for 1 hour. The reaction mixture was cooled to room temperature, and then concentrated. The crude product was partitioned between saturated aqueous sodium bicarbonate and ethyl acetate. The organic phase was dried over Na₂SO₄, filtered, and concentrated to afford 3-chloro-4-(1-methyl-1H-tetrazol-5-yl)-phenylamine (490 mg, 93%) as a colorless oil. The crude product was taken onto the next step without additional purification.

5-(2-chloro-4-isothiocyanatophenyl)-1-methyl-1H-tetrazole

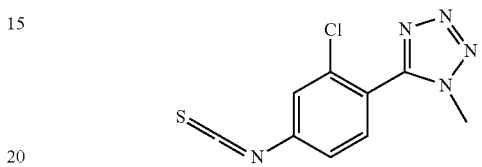

In a 500 mL round-bottomed flask, 3-chloro-4-(1-methyl-1H-tetrazol-5-yl)aniline (490 mg, 2.34 mmol, Eq: 1.00) and 1,1'-thiocarbonyldiimidazole (480 mg, 2.69 mmol, Eq: 1.15) were combined with methylene chloride (20 ml) to give a light brown suspension. The reaction mixture was stirred at room temperature over the weekend under a balloon of argon. The reaction mixture was concentrated over silica gel, and the silica gel supported crude product was loaded onto a 115 gram Analogix column. Flash chromatography (40% ethyl acetate-hexanes) afforded 5-(2-chloro-4-isothiocyanatophenyl)-1-methyl-1H-tetrazole (334 mg, 57%) as a colorless film.

(Z)-methyl N-3-chloro-4-(1-methyl-1H-tetrazol-5-yl)phenyl-N'-cyanocarbamimidothioate

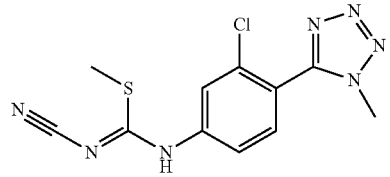 [SMILES: CS/C(=N\C#N)Nc1ccc(-c2nnnn2C)c(Cl)c1]

In a 250 mL pear-shaped flask, a 0.5 M solution of sodium methoxide in methanol (4.0 mL, 2.00 mmol, Eq: 1.51) and cyanamide (167 mg, 3.98 mmol, Eq: 3.0) were combined with methanol (13 mL) to give a colorless solution. This mixture was stirred at room temperature for 15 minutes. This mixture was then added dropwise to a mixture of 5-(2-chloro-4-isothiocyanatophenyl)-1-methyl-1H-tetrazole (334 mg, 1.33 mmol, Eq: 1.00) and 13 mL methanol. The resulting mixture was stirred at room temperature for one hour. After this time, methyl iodide (284 mg, 125 μl, 2.00 mmol, Eq: 1.51) was added. The reaction mixture was stirred at room temperature overnight. In the morning, a white precipitate had formed. This product was collected using vacuum filtration, furnishing (Z)-methyl N-3-chloro-4-(1-methyl-1H-tetrazol-5-yl)phenyl-N'-cyanocarbamimidothioate (258 mg, 63%) as a white powder.

N3-(3-Chloro-4-(1-methyl-1H-tetrazol-5-yl)phenyl)-1H-1,2,4-triazole-3,5-diamine (Compound 15)

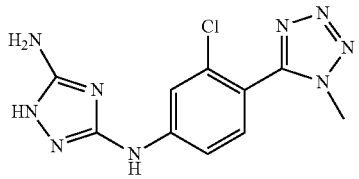 [SMILES: Cn1nnnc1-c1ccc(Nc2n[nH]c(N)n2)cc1Cl]

In a 100 mL round-bottomed flask, (Z)-methyl N-3-chloro-4-(1-methyl-1H-tetrazol-5-yl)phenyl-N'-cyanocarbamimidothioate (258 mg, 838 µmol, Eq: 1.00) and hydrazine (265 µL, 8.43 mmol, Eq: 10.1) were combined with ethanol (8.5 mL). The reaction mixture was refluxed for three hours. After this time, the reaction mixture was cooled to room temperature, then stirred at room temperature overnight. In the morning, a white precipitate came out of solution, giving a thick white suspension. The precipitate was collected via vacuum filtration, giving N3-(3-chloro-4-(1-methyl-1H-tetrazol-5-yl)phenyl)-1H-1,2,4-triazole-3,5-diamine. MS calcd. for $C_{10}H_{10}ClN_9$ [(M+H)]: 292, obsd. 292.0.

N3-(3-chloro-4-(1-methyl-1H-1,2,4-triazol-5-yl)phenyl)-1H-1,2,4-triazole-3,5 diamine (Compound 16)

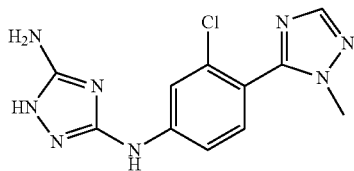 [SMILES: Cn1ncnc1-c1ccc(Nc2n[nH]c(N)n2)cc1Cl]

2-Chloro-N-[1-dimethylamino-meth-(Z)-ylidene]-4-nitro-benzamide

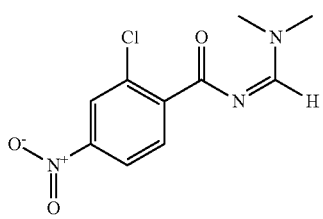 [SMILES: CN(C)/C=N\C(=O)c1ccc([N+](=O)[O-])cc1Cl]

In a 500 mL round-bottom flask, 2-chloro-4-nitrobenzamide (3.5 g, 17.4 mmol, Eq: 1.00) and N,N-dimethylformamide dimethyl acetal (23 mL, 173 mmol, Eq: 9.92) were combined to give an off-white suspension. This mixture was heated at 130° C. overnight. In the morning, the solvent was evaporated off, giving 2-chloro-N-[1-dimethylamino-meth-(Z)-ylidene]-4-nitro-benzamide as a yellow solid. This crude product was used in subsequent steps without further purification.

5-(2-chloro-4-nitrophenyl)-1-methyl-1H-1,2,4-triazole

In a 500 mL round-bottomed flask, (Z)-2-chloro-N-((dimethylamino)methylene)-4-nitrobenzamide (2.0 g, 7.82 mmol, Eq: 1.00) and methylhydrazine (5.35 mL, 102 mmol, Eq: 13) were combined with glacial acetic acid (90 mL) to give an off-white suspension. The reaction mixture was heated at 90° C. for 1.5 hours. After this time, the reaction mixture was cooled to about 50° C., and subsequently concentrated on the rotary evaporator. The crude product was partitioned between ethyl acetate and saturated aqueous NaHCO$_3$. The organic phase was dried over MgSO$_4$, filtered, and concentrated. The crude product was purified using flash chromatography (120 gram Analogix column, 15-35% ethyl acetate-hexanes) to provide 5-(2-chloro-4-nitrophenyl)-1-methyl-1H-1,2,4-triazole (481 mg, 26%) as a yellow solid.

3-Chloro-4-(1-methyl-1H-1,2,4-triazol-5-yl)aniline

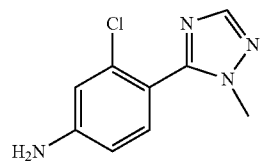

In a 250 mL round-bottomed flask, 5-(2-chloro-4-nitrophenyl)-1-methyl-1H-1,2,4-triazole (481 mg, 2.02 mmol, Eq: 1.00), iron (113 mg, 2.02 mmol, Eq: 1.00) and ammonium chloride (108 mg, 2.02 mmol, Eq: 1.00) were combined with methanol (5.4 mL) to give a brown suspension. Water (2.7 mL) was added. The reaction mixture was heated at 85° C. After only 15 minutes, the reaction mixture had already changed to a rust-colored suspension. The reaction mixture was stirred at 85° C. for three hours. After this time, TLC indicated that some starting material still remained. The reaction mixture was cooled to room temperature. Additional iron (108 mg iron, 1.93 mmol) and ammonium chloride (113 mg, 2.11 mmol) were added. The reaction mixture was heated for another 1 hour, and then cooled to room temperature. The reaction mixture was stirred at room temperature overnight. After this time, TLC indicated that the reaction was complete. The mixture was concentrated, and the residue was partitioned between ethyl acetate and saturated aqueous sodium bicarbonate. The organic phase was dried over Na$_2$SO$_4$, filtered, and concentrated to afford 3-chloro-4-(1-methyl-1H-1,2,4-triazol-5-yl)aniline as a yellow oil.

5-(2-Chloro-4-isothiocyanatophenyl)-1-methyl-1H-1,2,4-triazole

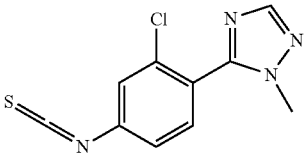 [SMILES: Cn1ncnc1-c1ccc(N=CC=S)cc1Cl]

In a 1 L round-bottom flask, 3-chloro-4-(1-methyl-1H-1,2,4-triazol-5-yl)aniline (421 mg, 2.02 mmol, Eq: 1.00) and 1,1'-thiocarbonyldiimidazole (414 mg, 2.32 mmol, Eq: 1.15) were combined with methylene chloride (20.2 mL) to give a brown suspension. This reaction mixture was stirred at room temperature over the weekend. The reaction mixture was concentrated over silica gel. The silica-gel supported crude product was loaded onto a 120 gram silica gel column. Flash chromatography (35% ethyl acetate-hexanes) gave 5-(2-chloro-4-isothiocyanatophenyl)-1-methyl-1H-1,2,4-triazole (280 mg, 55%).

(Z)-Methyl N-3-chloro-4-(1-methyl-1H-1,2,4-trizaol-5-yl)phenyl-N'-cyanocarbamimidothioate

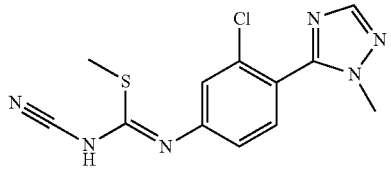 [SMILES: CS/C(=N\c1ccc(-c2ncnn2C)c(Cl)c1)NC#N]

In a 10 mL pear-shaped flask, a 0.5 M solution of sodium methoxide in methanol (840 µL, 420 µmol, Eq: 1.5) and cyanamide (35.0 mg, 833 µmol, Eq: 2.98) were combined to give a colorless solution. This mixture was stirred at room temperature for 15 minutes. After this time, the mixture was added to a solution of 11 mL methanol and 5-(2-chloro-4-isothiocyanatophenyl)-1-methyl-1H-1,2,4-triazole (70 mg, 279 µmol, Eq: 1.00). The reaction mixture was stirred at room temperature for 1 hour. Methyl iodide (104 µL, 1.68 mmol) was added, and the reaction mixture was stirred at room temperature overnight. In the morning, the reaction mixture was a clear, colorless solution. The solvent was evaporated without heating so that there was 1 mL of methanol remaining. This mixture was diluted with methylene chloride (10 mL). Upon addition of methylene chloride, the reaction mixture became cloudy. The diluted reaction mixture was concentrated over silica gel with minimal heating. The silica gel supported crude product was loaded onto a 25 gram silica gel column. Flash chromatography (80%-100% ethyl acetate-hexanes) provided (Z)-methyl N-3-chloro-4-(1-methyl-1H-1,2,4-trizaol-5-yl)phenyl-N'-cyano-carbamimidothioate (28 mg, 33%) as a white solid.

N3-(3-chloro-4-(1-methyl-1H-1,2,4-triazol-5-yl)phenyl)-1H-1,2,4-triazole-3,5-diamine (Compound 16)

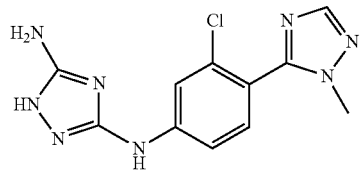 [SMILES: Cn1ncnc1-c1ccc(Nc2n[nH]c(N)n2)cc1Cl]

In a 10 mL round-bottom flask, (Z)-methyl N-3-chloro-4-(1-methyl-1H-1,2,4-trizaol-5-yl)phenyl-N'-cyano-carbamimidothioate (28 mg, 91.3 µmol, Eq: 1.00) and hydrazine (30.6 mg, 30 µL, 955 µmol, Eq: 10.5) were combined with ethanol (1 mL) to give a colorless solution. The reaction mixture was heated at 75° C. for hours. The reaction mixture was concentrated to afford N3-(3-chloro-4-(1-methyl-1H-1,2,4-triazol-5-yl)phenyl)-1H-1,2,4-triazole-3,5-diamine (23 mg, 87%) as a white powder. MS cald. for $C_{11}H_{11}ClN_8$ [(M+H)]: 291, obsd. 291.0.

N3-(3,5-dichloro-4-(1H-pyrazol-1-yl)phenyl)-1H-1,2,4-triazole-3,5-diamine (Compound 17)

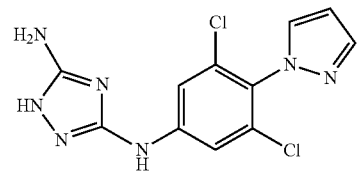 [SMILES: Nc1nc(Nc2cc(Cl)c(-n3cccn3)c(Cl)c2)n[nH]1]

1-(2,6-Dichloro-4-nitro-phenyl)-1H-pyrazole

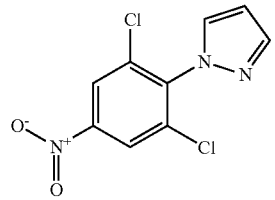 [SMILES: O=[N+]([O-])c1cc(Cl)c(-n2cccn2)c(Cl)c1]

In a 250 mL round-bottom flask, 1,3-dichloro-2-fluoro-5-nitrobenzene (1.5 g, 7.14 mmol, Eq: 1.00), 1H-pyrazole (486 mg, 7.14 mmol, Eq: 1.00) and potassium carbonate (1.5 g, 10.9 mmol, Eq: 1.52) were combined with DMF (30 mL) to give a yellow suspension. This mixture was heated at 115° C. for three hours. The reaction mixture was cooled to room temperature. The cooled mixture was poured into ~100 mL of ice water. A cream-colored solid precipitated out. The precipitate was collected via vacuum filtration and air dried to provide 1-(2,6-dichloro-4-nitro-phenyl)-1H-pyrazole (1.73 g, 94%) as an off-white solid.

3,5-Dichloro-4-pyrazol-1-yl-phenylamine

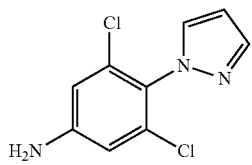 [SMILES: Nc1cc(Cl)c(-n2cccn2)c(Cl)c1]

In a 250 mL round-bottom flask, 1-(2,6-dichloro-4-nitrophenyl)-1H-pyrazole (1.73 g, 6.7 mmol, Eq: 1.00), iron (1.80 g, 32.2 mmol, Eq: 4.81) and ammonium chloride (3.6 g, 67.3 mmol, Eq: 10.0) were combined with methanol (18 mL) to give a grey suspension. Water (9 mL) was added. The reaction mixture was heated at 85° C. for 6 hours. The reaction mixture was cooled to room temperature, and then partitioned between ethyl acetate and saturated aqueous ammonium chloride. The organic phase was dried (Na$_2$SO$_4$), filtered, and finally concentrated to afford 3,5-dichloro-4-pyrazol-1-yl-phenylamine (1.29 g, 84%) as a beige solid.

1-(2,6-Dichloro-4-isothiocyanato-phenyl)-1H-pyrazole

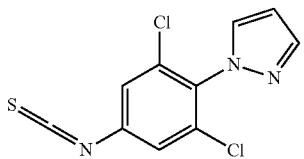 [SMILES: S=CC=Nc1cc(Cl)c(-n2cccn2)c(Cl)c1]

In a 1 L round-bottomed flask, 3,5-dichloro-4-(1H-pyrazol-1-yl)aniline (1.5 g, 6.58 mmol, Eq: 1.00) and 1,1'-Thiodicarbonylimidazole (1.30 g, 7.29 mmol, Eq: 1.11) were combined with methylene chloride (50 mL) to give a light yellow suspension. The reaction mixture was stirred at room temperature for 24 hours. The reaction mixture was concentrated over silica gel, and the silica gel supported crude product was loaded onto a 120 gram silica gel column. Flash chromatography (15% ethyl acetate-hexanes) afforded 1-(2,6-dichloro-4-isothiocyanato-phenyl)-1H-pyrazole (886 mg, 50%) as a light yellow oil.

(Z)-Methyl N-3-chloro-4-(1-methyl-1H-pyrazol-1-yl)-phenyl-N'-cyanocarbamimidothioate

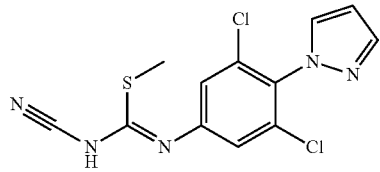 [SMILES: CS/C(=N\c1cc(Cl)c(-n2cccn2)c(Cl)c1)NC#N]

In a 100 mL round-bottomed flask, cyanamide (75 mg, 1.78 mmol, Eq: 3.01) and a 0.5 M solution of sodium methoxide in methanol (1.77 mL, 886 µmol, Eq: 1.5) were combined to give a colorless solution. This mixture was stirred at room temperature for 15 minutes. After this time, the cyanamide mixture was added rapidly dropwise to a solution of 1-(2,6-dichloro-4-isothiocyanatophenyl)-1H-pyrazole (160 mg, 592 µmol, Eq: 1.00) in methanol (10 mL). This mixture was stirred at room temperature for 1 hour. Finally, iodomethane (126 mg, 55.6 µL, 888 µmol, Eq: 1.5) was added. The reaction mixture was diluted with 10 mL of methylene chloride and concentrated over celite. The celite-supported crude product was loaded onto a 40 gram silica gel column. Flash chromatography (15%-75% ethyl acetate-hexanes) provided (Z)-methyl N-3-chloro-4-(1-methyl-1H-pyrazol-1-yl)-phenyl-N'-cyanocarbamimidothioate (62 mg, 32%) as a white solid.

N3-(3,5-dichloro-4-(1H-pyrazol-1-yl)phenyl)-1H-1,2,4-triazole-3,5-diamine (Compound 17)

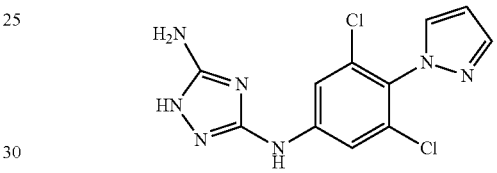

In a 25 mL round-bottomed flask, (Z)-methyl N-3-chloro-4-(1-methyl-1H-pyrazol-1-yl)-phenyl-N'-cyanocarbamimidothioate (62 mg, 190 µmol, Eq: 1.00) and hydrazine (61.2 mg, 60 µl, 1.91 mmol, Eq: 10.1) were combined with ethanol (1.5 ml) to give a colorless solution. This mixture was refluxed for 16 hours. The reaction mixture was concentrated, and redissolved in a 10% ethanol-methylene chloride solution. This mixture was filtered and the filtrate was concentrated. The product was further dried down in the vacuum oven at −75° C. to give N3-(3,5-dichloro-4-(1H-pyrazol-1-yl)phenyl)-1H-1,2,4-triazole-3,5-diamine (58 mg, 99%) as a light brown powder. MS cald. for C$_{11}$H$_9$Cl$_2$N$_7$ [(M+14)]: 311, obsd. 311.8.

tert-Butyl 4-(4-(5-amino-1H-1,2,4-triazol-3-ylamino)-2,6-dichlorophenyl)-5,6-dihydropyridine-1(2H)-carboxylate (Compound 18)

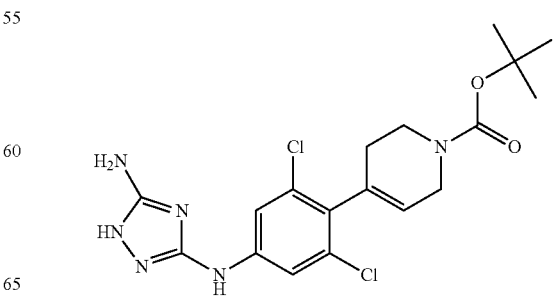

4-(4-Amino-2,6-dichloro-phenyl)-3,6-dihydro-2H-pyridine-1-carboxylic acid tert-butyl ester

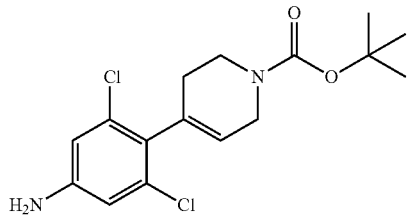 [SMILES: CC(C)(C)OC(=O)N1CC=C(c2c(Cl)cc(N)cc2Cl)CC1]

In a sealed tube, 1-(tert-butoxycarbonyl)-1,2,3,6-tetrahydropyridin-4-ylboronic acid (450 mg, 1.98 mmol, Eq: 0.955), [1,1'-bis(diphenylphosphino)ferrocene]dichloropalladium(II) (150 mg, 205 µmol, Eq: 0.0988) and 4-bromo-3,5-dichloroaniline (0.5 g, 2.08 mmol, Eq: 1.00) were combined with DMF (7 mL) to give a dark red suspension. Potassium carbonate (860 mg, 6.22 mmol, Eq: 3.00) was added. The reaction mixture was heated at 115° C. overnight. The reaction mixture was combined with water, then the dark suspension was extracted with ethyl acetate. The organic phase was dried (MgSO₄), filtered, and concentrated to a black oil. This product was dissolved in $CH_2Cl_2$ and the mixture was concentrated over silica gel. The silica gel supported crude product was loaded onto an 80 gram silica gel column. Flash chromatography (5%-20% ethyl acetate-hexanes) provided 4-(4-amino-2,6-dichloro-phenyl)-3,6-dihydro-2H-pyridine-1-carboxylic acid tert-butyl ester (0.267 g, 38%) as a light yellow oil.

4-(2,6-Dichloro-4-isothiocyanato-phenyl)-3,6-dihydro-2H-pyridine-1-carboxylic acid tert-butyl ester

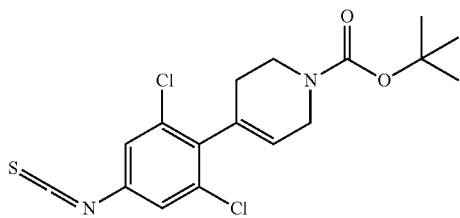 [SMILES: CC(C)(C)OC(=O)N1CC=C(c2c(Cl)cc(N=CC=S)cc2Cl)CC1]

In a 100 mL round-bottomed flask, tert-butyl 4-(4-amino-2,6-dichlorophenyl)-5,6-dihydropyridine-1(2H)-carboxylate (0.229 g, 667 µmol, Eq: 1.00) and 1,1'-thiocarbonyldiimidazole (140 mg, 786 µmol, Eq: 1.18) were combined with methylene chloride (4 mL) to give a brown suspension. The reaction mixture was stirred at room temperature over the weekend. The reaction was concentrated over silica gel. The silica gel supported crude product was loaded onto a 80 gram SiliCycle column. Flash chromatography afforded tert-butyl 4-(4-(5-amino-1H-1,2,4-triazol-3-ylamino)-2,6-dichlorophenyl)-5,6-dihydropyridine-1(2H)-carboxylate (216 mg, 84%) as a yellow oil.

(Z)-tert-Butyl 4-(2,6-dichloro-4-(cyanamido(methylthio)methylene-amino)phenyl)-5,6-dihydropyridine-1(2H)-carboxylate

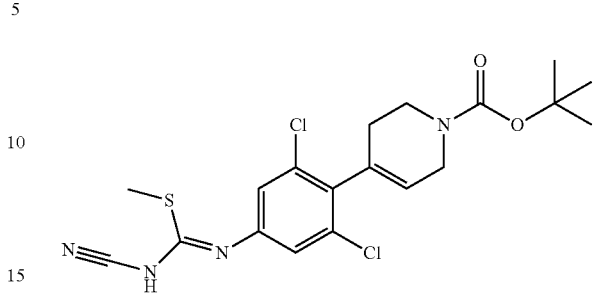

In a 100 mL round-bottomed flask, cyanamide (70 mg, 1.67 mmol, Eq: 2.98) and a 0.5 M solution of sodium methoxide in methanol (1.7 mL, 850 µmol, Eq: 1.52) were combined to give a colorless solution. This mixture was stirred at room temperature over 15 minutes. After this time, a solution of tert-butyl 4-(2,6-dichloro-4-isothiocyanatophenyl)-5,6-dihydropyridine-1(2H)-carboxylate (0.215 g, 558 µmol, Eq: 1.00) in methanol (5.6 mL) was added. The reaction mixture was stirred at room temperature for 1 hour. Finally, methyl iodide (118 mg, 52.0 µL, 832 µmol, Eq: 1.49) was added and the reaction mixture was stirred at room temperature overnight. The reaction mixture was concentrated directly over celite. The celite-supported crude product was loaded onto a 40 gram SiliCycle column. Flash chromatography (30%-65% ethyl acetate-hexanes) afforded (Z)-tert-butyl 4-(2,6-dichloro-4-(cyanamido(methylthio)methylene-amino)phenyl)-5,6-dihydropyridine-1(2H)-carboxylate (33 mg, 13%) as a colorless oil.

tert-Butyl 4-(4-(5-amino-1H-1,2,4-triazol-3-ylamino)-2,6-dichlorophenyl)-5,6-dihydropyridine-1(2H)-carboxylate (Compound 18)

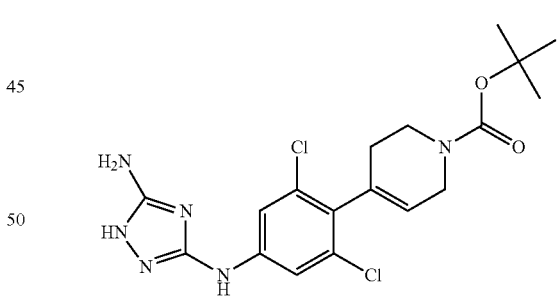

In a 50 mL pear-shaped flask, (Z)-tert-butyl 4-(2,6-dichloro-4-(cyanamido(methylthio)methylene-amino)phenyl)-5,6-dihydropyridine-1(2H)-carboxylate (33 mg, 74.8 µmol, Eq: 1.00) and hydrazine (24.5 mg, 24 µL, 765 µmol, Eq: 10.2) were combined with ethanol (1 mL) to give a colorless solution. The reaction mixture was heated at 75° C. for 2.5 hours. After this time, LCMS showed the reaction to be complete. The reaction mixture was concentrated to afford an oil. This product was re-dissolved in $CDCl_3$ and $CD_3OD$. Solvents were evaporated again to afford tert-butyl 4-(4-(5-amino-1H-1,2,4-triazol-3-ylamino)-2,6-dichlorophenyl)-5,6-dihydropyridine-1(2H)-carboxylate (22 mg, 69%) as an off-white oily solid. MS [(M+H)⁺] obsd. 425.0.

N3-(3,5-dichloro-4-(1,2,3,6-tetrahydropyridin-4-yl) phenyl)-1H-1,2,4-triazole-3,5-diamine (Compound 19)

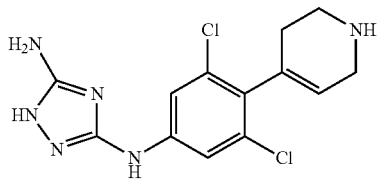 [SMILES: Nc1nc(Nc2cc(Cl)c(C3=CCNCC3)c(Cl)c2)n[nH]1]

In a 5 mL vial, tert-butyl 4-(4-(5-amino-1H-1,2,4-triazol-3-ylamino)-2,6-dichlorophenyl)-5,6-dihydropyridine-1 (2H)-carboxylate Compound 17 (16 mg, 37.6 µmol, Eq: 1.00) and 4.0 M HCl in dioxane (250 µL, 1.00 mmol, Eq: 26.6) were combined with methylene chloride (250 µL) to give a light brown suspension. The reaction mixture was stirred at room temperature over 3 hours. The mixture was then partioned between ethyl acetate and saturated aqueous NaHCO$_3$. The organic phase was dried (Na$_2$SO$_4$), filtered and concentrated to afford N3-(3,5-dichloro-4-(1,2,3,6-tetrahydropyridin-4-yl)phenyl)-1H-1,2,4-triazole-3,5-diamine as a colorless oil. MS [(M−H)⁻] obsd. 323.1.

tert-Butyl 4-(4-(5-amino-1H-1,2,4-triazol-3-ylamino)-2-chloro-6-(trifluoromethyl)phenyl)-5,6-dihydropyridine-1(2H)-carboxylate (Compound 20)

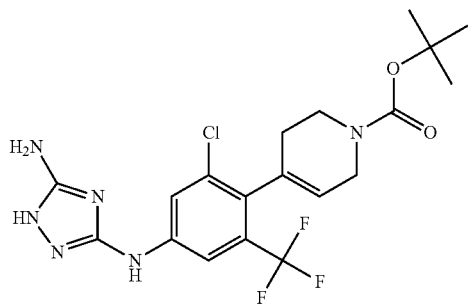 [SMILES: CC(C)(C)OC(=O)N1CC=C(c2c(Cl)cc(Nc3n[nH]c(N)n3)cc2C(F)(F)F)CC1]

tert-butyl 4-(4-amino-2-chloro-6-(trifluoromethyl) phenyl)-5,6-dihydropyridine-1(2H)-carboxylate

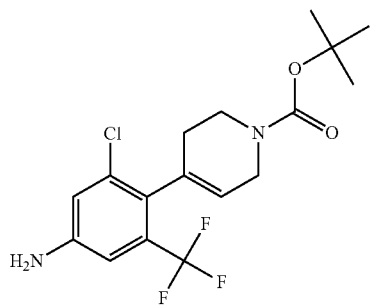 [SMILES: CC(C)(C)OC(=O)N1CC=C(c2c(Cl)cc(N)cc2C(F)(F)F)CC1]

In a 250 mL round-bottomed flask, 4-bromo-3-chloro-5-(trifluoromethyl)aniline (2.55 g, 9.29 mmol, Eq: 1.00), tert-butyl 4-(4,4,5,5-tetramethyl-1,3,2-dioxaborolan-2-yl)-5,6-dihydropyridine-1(2H)-carboxylate (2.76 g, 8.92 mmol, Eq: 0.96) and potassium carbonate (3.85 g, 27.9 mmol, Eq: 3.0) were combined with DMF (30 mL). 1,1'-Bis(diphenylphosphino)ferrocene-palladium(II) dichloromethane complex (1.14 g, 1.39 mmol, Eq: 0.15) was added. The reaction mixture was stirred overnight at 125° C. The reaction mixture was cooled to room temperature and poured into water. The resulting suspension was extracted with ethyl acetate. The organic phase was dried over MgSO$_4$, filtered, and concentrated over silica gel. The silica gel supported crude product was split into two lots. Each lot was purified separately on a 120 gram SiliCycle column using flash chromatography (15%-40% ethyl acetate-hexanes) to afford tert-butyl 4-(4-amino-2-chloro-6-(trifluoromethyl)phenyl)-5,6-dihydropyridine-1(2H)-carboxylate (2.23 g, 64%) as a light yellow oil.

tert-Butyl 4-(2-chloro-4-isothiocyanato-6-(trifluoromethyl)phenyl)-5,6-dihydropyridine-1(2H)-carboxylate

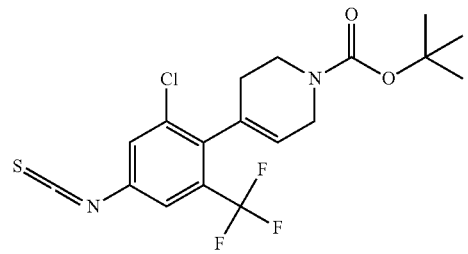 [SMILES: CC(C)(C)OC(=O)N1CC=C(c2c(Cl)cc(N=CC=S)cc2C(F)(F)F)CC1]

In a 1 L round-bottomed flask, tert-butyl 4-(4-amino-2-chloro-6-(trifluoromethyl)phenyl)-5,6-dihydropyridine-1 (2H)-carboxylate (2.23 g, 5.92 mmol, Eq: 1.00) and di(1H-imidazol-1-yl)methanethione (1.2 g, 6.73 mmol, Eq: 1.14) were combined with methylene chloride (60 mL) to give a light yellow solution. The reaction mixture was stirred overnight at room temperature. The reaction mixture was concentrated over silica gel. The silica gel supported crude product was loaded onto a 120 gram silica gel column. Flash chromatography (10%-20% ethyl acetate-hexanes) provided tert-butyl 4-(2-chloro-4-isothiocyanato-6-(trifluoromethyl) phenyl)-5,6-dihydropyridine-1(2H)-carboxylate (1.67 g, 67%) as a colorless oil.

(Z)-tert-Butyl 4-(2-chloro-4-(cyanamido(methylthio)-methyleneamino)-6-(trifluoromethyl)phenyl)-5, 6-dihydropyridine-1(2H)-carboxylate

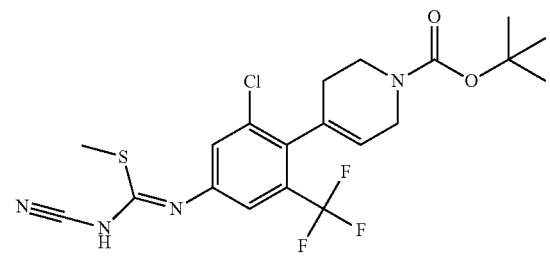 [SMILES: CS/C(=N\c1cc(Cl)c(C2=CCN(C(=O)OC(C)(C)C)CC2)c(C(F)(F)F)c1)NC#N]

In a 250 mL round-bottomed flask, a 0.5 M solution of sodium methoxide in methanol (7.16 mL, 3.58 mmol, Eq: 1.5) and cyanamide (301 mg, 7.16 mmol, Eq: 3.0) were combined to give a colorless solution. The mixture was stirred at room temperature for 20 minutes. A solution of tert-butyl 4-(2-chloro-4-isothiocyanato-6-(trifluoromethyl)phenyl)-5,6-dihydropyridine-1(2H)-carboxylate (1.0 g, 2.39 mmol) in 18 mL of methanol was added dropwise via a syringe. The reaction mixture was stirred at room temperature over 1.5 hours. After this time, methyl iodide (224 µL, 3.58 mmol, Eq: 1.5) was added. The reaction mixture was stirred at room temperature overnight. The reaction mixture was concentrated over celite.

The celite supported crude product was loaded onto a 80 gram silica gel column. Flash chromatography (15%-50% ethyl acetate-hexanes gave (Z)-tert-butyl 4-(2-chloro-4-(cyanamido-(methylthio)methyleneamino)-6-(trifluoromethyl)phenyl)-5,6-dihydropyridine-1(2H)-carboxylate (0.776 g, 68%) as a light yellow oil.

tert-Butyl 4-(4-(5-amino-1H-1,2,4-triazol-3-ylamino)-2,6-dichlorophenyl)-5,6-dihydropyridine-1(2H)-carboxylate (Compound 20)

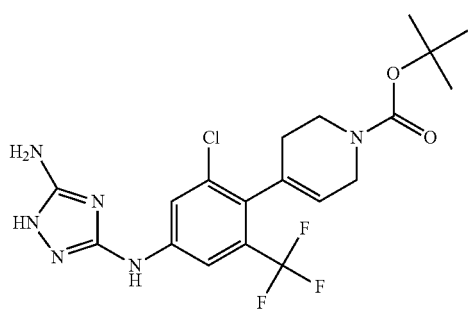 [SMILES: CC(C)(C)OC(=O)N1CC=C(c2c(Cl)cc(Nc3n[nH]c(N)n3)cc2C(F)(F)F)CC1]

In a 250 mL round-bottomed flask, (Z)-tert-butyl 4-(2-chloro-4-(cyanamido(methylthio)-methyleneamino)-6-(trifluoromethyl)phenyl)-5,6-dihydropyridine-1(2H)-carboxylate (0.776 g, 1.63 mmol, Eq: 1.00) and hydrazine (524 mg, 513 µL, 16.3 mmol, Eq: 10) were combined with ethanol (16 mL) to give a colorless solution. The reaction mixture was refluxed for 4 hours, then cooled to room temperature and stirred for another 3 hours. After this time, LC-MS analysis showed a small amount of starting material and a possible intermediate. Heating was continued for another 14 hours. After this time the reaction was cooled to room temperature and concentrate to a pink oil. This crude product was precipitated from 10 mL of 30% ethanol-methylene chloride. This first crop of precipitate was isolated by filtration. The mother liquor from above eventually solidified over the weekend. These solids were triturated with cold ethanol, and then the slurry was filtered. Collected solids were washed with cold ethanol and then dried using vacuum filtration to provide a second crop. The first and second crops were combined to afford tert-butyl 4-(4-(5-amino-1H-1,2,4-triazol-3-ylamino)-2-chloro-6-(trifluoromethyl)phenyl)-5,6-dihydropyridine-1(2H)-carboxylate (183 mg, 24%) as an off-white solid. MS cald. for $C_{19}H_{22}ClF_3N_6O_2$ [(M+H)$^+$]: 459, obsd. 459.0.

N3-[3-Chloro-4-(1,2,3,6-tetrahydro-pyridin-4-yl)-5-trifluoromethyl-phenyl]-1H-[1,2,4]triazole-3,5-diamine hydrochloride (Compound 21)

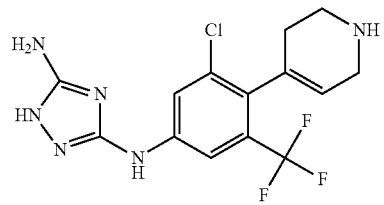 [SMILES: Nc1nc(Nc2cc(Cl)c(C3=CCNCC3)c(C(F)(F)F)c2)n[nH]1]

In a 20 mL pear-shaped flask, tert-butyl 4-(4-(5-amino-1H-1,2,4-triazol-3-ylamino)-2-chloro-6-(trifluoromethyl)phenyl)-5,6-dihydropyridine-1(2H)-carboxylate Compound 19 (20 mg, 43.6 µmol, Eq: 1.00) and a 4 M solution of hydrochloric acid in dioxane (500 µL, 2.00 mmol, Eq: 45.9) were combined with dioxane (500 µL) to give a colorless solution. After only a few minutes, oily solids precipitated at the bottom of the reaction flask. The reaction mixture was stirred at room temperature for 5 hours. After this time, the reaction mixture was allowed to settle without stirring. The liquids were decanted, giving only the oily solid in the flask. This product was dissolved in methanol and then transferred to a vial and concentrated to afford N3-[3-chloro-4-(1,2,3,6-tetrahydro-pyridin-4-yl)-5-trifluoromethyl-phenyl]-1H-[1,2,4]triazole-3,5-diamine hydrochloride. MS cald. for $C_{14}H_{14}ClF_3N_6$ [(M+H)$^+$]: 359, obsd. 359.0.

N*3*-(3,5-Dichloro-4-[1,2,4]triazolo[4,3-a]pyridin-3-yl-phenyl)-1H-[1,2,4]triazole-3,5-diamine (Compound 22)

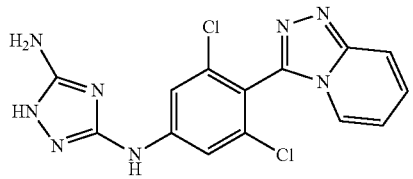 [SMILES: Nc1nc(Nc2cc(Cl)c(-c3nnc4ccccn34)c(Cl)c2)n[nH]1]

4-([1,2,4]triazolo[4,3-a]pyridin-3-yl)-3,5-dichloroaniline

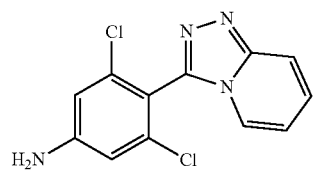 [SMILES: Nc1cc(Cl)c(-c2nnc3ccccn23)c(Cl)c1]

A solution of 2,6-dichloro-4-nitro-benzaldehyde (105 mg, 0.48 mmol) and 2-hydrazinylpyridine (57 mg, 0.52 mmol) in CH$_3$OH was heated to 50° C. for 3 hours after which all volatiles were removed under reduced pressure. The resulting solid was suspended in THF (5 mL) and chloramine-T (164 mg, 0.67 mmol) was added to yield a deep burgundy colored reaction mixture which was heated to 50° C. for one hour. All volatiles were again removed and the desired product, 3-(2,6-dichloro-4-nitrophenyl)-[1,2,4]triazolo[4,3-a]pyridine (120 mg, 81%) was isolated as an orange solid by silica gel chromatography (EtOAc).

A solution of 3-(2,6-dichloro-4-nitrophenyl)-[1,2,4]triazolo[4,3-a]pyridine(105 mg, 0.34 mmol) in a 1:1 mixture of THF:satd $NH_4Cl$ (4 mL) was treated with zinc dust (67 mg; 1.0 mmol) and the reaction mixture was stirred for 2 hours. Filtration followed by removal of volatiles under reduced pressure gave the crude reaction product. 4-([1,2,4]triazolo[4,3-a]pyridin-3-yl)-3,5-dichloroaniline (26 mg, 27%) was isolated as a yellow oil by silica gel chromatography (EtOAc).

N*3*-(3,5-Dichloro-4-[1,2,4]triazolo[4,3-a]pyridin-3-yl-phenyl)-1H-[1,2,4]triazole-3,5-diamine (Compound 22)

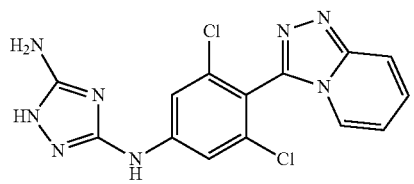 [SMILES: Nc1nc(Nc2cc(Cl)c(-c3nnc4ccccn34)c(Cl)c2)n[nH]1]

4-([1,2,4]triazolo[4,3-a]pyridin-3-yl)-3,5-dichloroaniline (58 mg, 0.28 mmol) and thiocarbonyldiimidazole (58 mg, 0.21 mmol) were stirred overnight in a solution of $CH_2Cl_2$ (2 mL) after which the product, 3-(2,6-dichloro-4-isothiocyanatophenyl)-[1,2,4]triazolo[4,3-a]pyridine, was isolated directly by column chromatography (66% EtOAc in hexane) as a white solid (37 mg, 55%).

Sodium hydrogencyanamide (8.4 mg, 0.13 mmol) was added to a solution of 3-(2,6-dichloro-4-isothiocyanatophenyl)-[1,2,4]triazolo[4,3-a]pyridine (35 mg, 0.11 mmol) in 1:1 $CH_3OH:CH_3CN$ (2 mL). The reaction mixture was stirred for 3 hours after which no starting material was detected by TLC. Iodomethane (13.6 μL; 0.22 mmol) was then added and the reaction mixture was stirred overnight. All volatiles were removed under reduced pressure to yield a waxy solid from which (Z)-methyl N-4-([1,2,4]triazolo[4,3-a]pyridin-3-yl)-3,5-dichlorophenyl-N'-cyanocarbamimidothioate (29 mg; 71%) was purified by silica gel chromatography (AcOEt)

(Z)-Methyl N-4-([1,2,4]triazolo[4,3-a]pyridin-3-yl)-3,5-dichlorophenyl-N'-cyanocarbamimidothioate (26 mg, 0.069 mmol) and hydrazine (10.8 L, 0.34 mmol) were heated in ethanol for 3 hours after which all volatiles were removed under reduced pressure. From the crude product, N*3*-(3,5-dichloro-4-[1,2,4]triazolo[4,3-a]pyridin-3-yl-phenyl)-1H-[1,2,4]triazole-3,5-diamine was isolated as a white solid by column chromatography (21 mg, 84%). MH+=361.0

N*3*-{3-Chloro-4-[6-(propane-2-sulfonyl)-pyridin-3-yl]-5-trifluoromethyl-phenyl}-1H-[1,2,4]triazole-3,5-diamine (Compound 23)

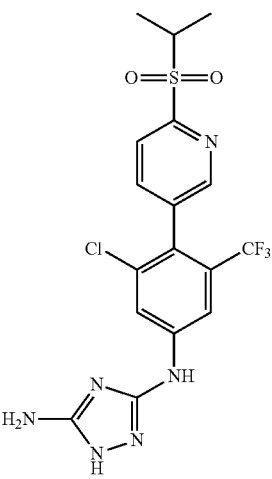 [SMILES: CC(C)S(=O)(=O)c1ccc(-c2c(Cl)cc(Nc3n[nH]c(N)n3)cc2C(F)(F)F)cn1]

5-Bromo-2-isopropylsulfanyl-pyridine

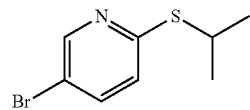

To a solution of 5-bromo-2-chloropyridine (1.03 g, 5.35 mmol, Eq: 1) in dimethylformamide (20 ml) was added sodium 2-propanethiolate (3 g, 30.6 mmol, Eq: 5.71) and the resulting mixture stirred at room temperature for 1H. The resulting mixture was poured into water (20 ml) and extracted with methylene chloride (3×50 ml). The combined organic phases were washed with brine (1×100 ml) and dried over magnesium sulfate. The mixture was filtered and evaporated to give crude 5-bromo-2-isopropylsulfanyl-pyridine as a yellow oil.

5-Bromo-2-(propane-2-sulfonyl)-pyridine

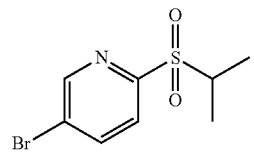

To a solution of crude 5-bromo-2-isopropylsulfanyl-pyridine (1.24 g, 5.34 mmol, Eq: 1) in dichloromethane (10 ml) was added 3-chloroperoxybenzoic acid (4.61 g, 13.4 mmol, Eq: 2.5) in 5 portions over 15 minutes. The resulting mixture was stirred at room temperature for 30 minutes before being quenched with a 1N sodium hydroxide solution (25 ml). The resulting mixture was extracted with dichloromethane (3×50 ml) and the combined organic phases washed with water (100 ml) and brine (100 ml) and dried over magnesium sulfate. The mixture was filtered and evaporated to give a white solid which was purified by flash chromatography (Analogix Intelliflash 310, Analogix SF15-12 g column, 0-20% ethyl acetate/hexane). Like fractions were combined and evaporated to give 5-bromo-2-(propane-2-sulfonyl)-pyridine as a white solid (995 mg, 71%).

2-(Propane-2-sulfonyl)-5-(4,4,5,5-tetramethyl-[1,3,2]dioxaborolan-2-yl)-pyridine

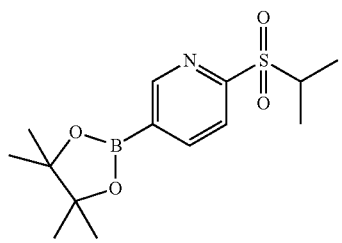 [SMILES: CC(C)S(=O)(=O)c1ccc(B2OC(C)(C)C(C)(C)O2)cn1]

To a solution of 5-bromo-2-(propane-2-sulfonyl)-pyridine (995 mg, 3.77 mmol, Eq: 1), 4,4,4',4',5,5,5',5'-octamethyl-2,2'-bi(1,3,2-dioxaborolane) (2.96 g, 11.6 mmol, Eq: 3.09), and potassium acetate (1.69 g, 17.3 mmol, Eq: 4.58) in dioxane (15 mL) was added 1,1'-bis(diphenylphosphino)ferrocene-palladium(II)dichloride dichloromethane complex (295 mg, 403 µmol, Eq: 0.107). The resulting mixture was heated to 85° C. overnight under an argon atmosphere. The resulting mixture was cooled to room temperature, diluted with ethyl acetate (50 ml) and evaporated. The residue was taken up in ethyl acetate (100 ml), washed with brine (100 ml) and dried over sodium sulfate. The mixture was filtered and to the filtrate was added silica gel (~3 g). The mixture was evaporated and purified by flash chromatography (Analogix Intelliflash, VersaPak Spherical Silica column 20-45 µM, 23 g, 10-50% ethyl acetate/hexane). Like fractions were combined and evaporated to give crude 2-(propane-2-sulfonyl)-5-(4,4,5,5-tetramethyl-[1,3,2]dioxaborolan-2-yl)-pyridine as a pale yellow solid (1.1221 g, 54% pure by HNMR, 52%).

N*3*-{3-Chloro-4-[6-(propane-2-sulfonyl)-pyridin-3-yl]-5-trifluoromethyl-phenyl}-1H-[1,2,4]triazole-3,5-diamine (Compound 23)

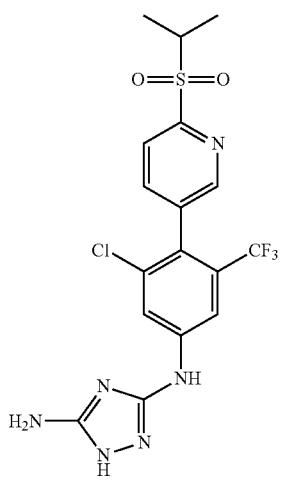 [SMILES: CC(C)S(=O)(=O)c1ccc(-c2c(Cl)cc(Nc3n[nH]c(N)n3)cc2C(F)(F)F)cn1]

A mixture of N3-(4-bromo-3-chloro-5-(trifluoromethyl)phenyl)-1H-1,2,4-triazole-3,5-diamine Intermediate 1 (407 mg, 1.14 mmol, Eq: 1.08), 2-(isopropylsulfonyl)-5-(4,4,5,5-tetramethyl-1,3,2-dioxaborolan-2-yl)pyridine (607 mg, 1.05 mmol, Eq: 1.00) a 3M potassium carbonate solution (702 µl, 2.11 mmol, Eq: 2), dimethoxyethane (2 ml) p-dioxane (2 ml) and tetrakis(triphenylphosphine)palladium(0) (277 mg, 240 µmol, Eq: 0.228) was placed in a microwave reaction tube and degassed with argon under sonication for 15 minutes. The tube was sealed and the resulting mixture was heated in a microwave reactor to 128° C. and held at that temperature for 3 h. The reaction mixture was cooled and diluted with ethyl acetate (2 mL) and water (1 mL) and the phases separated. The aqueous phase was extracted with ethyl acetate (3×1 mL) and the combined organic phases were washed with brine and dried over sodium sulfate. The resulting mixture was filtered and evaporated to give a brown residue which was chromatographed on silica (Analogix Intelliflash 310, RediSep silica 24 g, 4-10% methanol/dichloromethane gradient). Like fractions were combined and evaporated and the residue purified by SFC chromatography (THAR/SFC/Waters Multigram II system eluted with 25% methanol/carbon dioxide at 70 ml/mn on a CYANO column 3×25 cm with detection at 220 nM and 35 degrees and 100 bar backpressure) to give N*3*-{3-chloro-4-[6-(propane-2-sulfonyl)-pyridin-3-yl]-5-trifluoromethyl-phenyl}-1H-[1,2,4]triazole-3,5-diamine as a light yellow solid (125 mg, 26%). MS+m/z: 460.8 (M+H)+

5-[4-(5-Amino-1H-[1,2,4]triazol-3-ylamino)-2-chloro-6-trifluoromethyl-phenyl]-pyridine-2-sulfonic acid tert-butylamide (Compound 24)

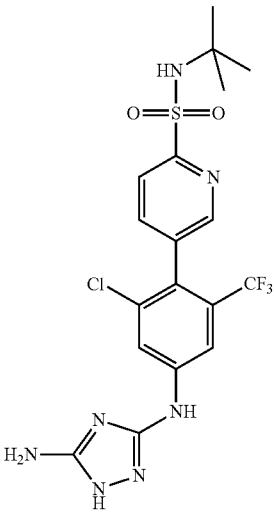 [SMILES: CC(C)(C)NS(=O)(=O)c1ccc(-c2c(Cl)cc(Nc3n[nH]c(N)n3)cc2C(F)(F)F)cn1]

2-(benzylthio)-5-bromopyridine

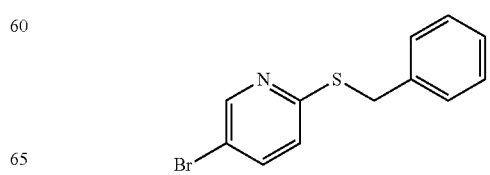

To a solution of benzyl mercaptan (5.29 g, 5.00 ml, 42.6 mmol, Eq: 1.1), in dry tetrahydrofuran (75 ml) was added sodium hydride (1.41 g, 55.7 mmol, Eq: 1.44) in 3 portions over 30 minutes. The resulting white slurry was allowed to stir at room temperature for 30 minutes before 2,5-dibromopyridine (9.17 g, 38.7 mmol, Eq: 1) was added in one portion. The resulting mixture was allowed to stir at room temperature for 3 hours. The resulting mixture was quenched with water (75 ml) and extracted with ether (3×100 mL). The ether layers were combined, washed with a saturated sodium bicarbonate solution (250 ml) and dried over magnesium sulfate. The mixture was filtered and evaporated to give 2-(benzylthio)-5-bromopyridine as a yellow oil (10.68 g).

5-Bromo-pyridine-2-sulfonic acid tert-butylamide

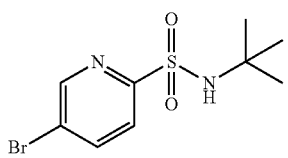

A mixture of crude 2-(benzylthio)-5-bromopyridine (2.94 g, 10.5 mmol, Eq: 1.00), water (30.0 ml), and carbon tetrachloride (125 ml) was cooled to 0° C. in an ice bath and vigorously stirred while chlorine gas was bubbled slowly through the mixture. After 3 minutes the reaction mixture was saturated with chlorine and turned bright yellow green. Bubbling was continued for 10 minutes followed by 5 additional minutes of stirring under a chlorine blanket before the mixture was sparged of chlorine by bubbling argon into the solution for 10 minutes. The mixture was diluted with dichloromethane (100 ml) and the phases separated. The organic phase was washed with water (100 ml), a saturated sodium bicarbonate solution (100 ml) and brine. The organic phase was treated with tert-butylamine (3.84 g, 5.56 ml, 52.5 mmol, Eq: 5), and stirred at room temperature overnight. The resulting mixture was washed with water (2×100 ml), a saturated sodium bicarbonate solution (2×100 ml) and brine (1×200 ml) and dried over magnesium sulfate. The mixture was filtered and evaporated and the residue purified by flash chromatography (Analogix Intelliflash 310, SF15-12 g column, 0-20% ethyl acetate/hexane gradient). Like fractions were combined and evaporated to give to 5-bromo-pyridine-2-sulfonic acid tert-butylamide as a pale yellow solid (565 mg, 18%).

5-(4,4,5,5-Tetramethyl-[1,3,2]dioxaorolan-2-yl)-pyridine-2-sulfonic acid tert-butylamide

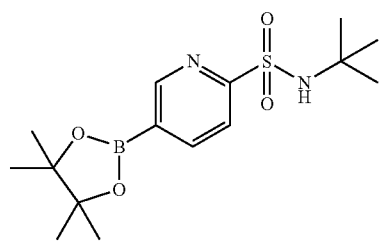 [SMILES: CC(C)(C)NS(=O)(=O)c1ccc(B2OC(C)(C)C(C)(C)O2)cn1]

To a solution of 5-bromo-pyridine-2-sulfonic acid tert-butylamide (565 mg, 1.93 mmol, Eq: 1.00), 4,4,4',4',5,5,5',5'-octamethyl-2,2'-bi(1,3,2-dioxaborolane) (1.51 g, 5.95 mmol, Eq: 3.09), and potassium acetate (866 mg, 8.83 mmol, Eq: 4.58) in dioxane (20 ml) was added 1,1'-bis(diphenylphosphino)ferrocene-palladium(II)dichloride dichloromethane complex (151 mg, 206 µmol, Eq: 0.107) and the resulting mixture heated to 85° C. overnight under an argon atmosphere. The resulting mixture was cooled to room temperature, diluted with ethyl acetate (25 ml) and evaporated. The residue was taken up in ethyl acetate (50 ml), washed with brine (50 ml) and dried over sodium sulfate. The mixture was filtered and to the filtrate was added silica gel (~1.5 g). The mixture was evaporated and purified by flash chromatography (Analogix Intelliflash, VersaPak Spherical Silica column 20-45 uM, 11 g column, 10-50% ethyl acetate/hexane). Like fractions were combined and evaporated to give crude 5-(4,4,5,5-tetramethyl-[1,3,2]dioxaorolan-2-yl)-pyridine-2-sulfonic acid tert-butylamide as an off-white solid (404 mg, 37% pure, 23%).

5-[4-(5-Amino-1H-[1,2,4]triazol-3-ylamino)-2-chloro-6-trifluoromethyl-phenyl]-pyridine-2-sulfonic acid tert-butylamide (Compound 24)

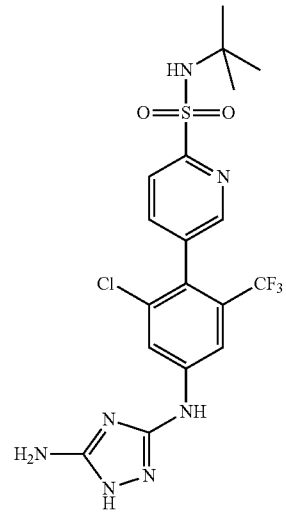 [SMILES: CC(C)(C)NS(=O)(=O)c1ccc(-c2c(Cl)cc(Nc3n[nH]c(N)n3)cc2C(F)(F)F)cn1]

A mixture of N3-(4-bromo-3-chloro-5-(trifluoromethyl) phenyl)-1H-1,2,4-triazole-3,5-diamine Intermediate 1 (253 mg, 709 µmol, Eq: 1), 5-(4,4,5,5-tetramethyl-[1,3,2]dioxaorolan-2-yl)-pyridine-2-sulfonic acid tert-butylamide (635 mg, 709 µmol, Eq: 1.00), a 3M potassium carbonate solution (473 µl, 1.42 mmol, Eq: 2), dimethoxyethane (1.5 ml) p-dioxane (1 ml) and tetrakis(triphenylphosphine)palladium (0) (152 mg, 131 µmol, Eq: 0.185) was placed in a microwave reaction tube and degassed with argon under sonication for 15 minutes. The tube was sealed and the resulting mixture was heated in a microwave reactor to 128° C. and held at that temperature for 3 h. The reaction mixture was cooled and diluted with ethyl acetate (3 mL) and water (8 mL) and the phases separated. The aqueous phase was extracted with ethyl acetate (3×15 mL) and the combined organic phases were washed with brine and dried over sodium sulfate. The resulting mixture was filtered and evaporated to give a brown residue which was chromatographed on silica (Analogix Intelliflash 310, RediSep silica 24 g, 4-10% methanol/dichloromethane gradient). Like fractions were combined and evaporated and the residue purified by SFC chromatography (THAR/SFC/Waters Multigram II system eluted with 25% methanol/carbon dioxide at 70 ml/mn on a CYANO column 3×25 cm with detection at 220 nM and 35 degrees and 100 bar backpressure) to give 5-(4-(5-amino-1H-1,2,4-triazol-3-ylamino)-2-chloro-6-(trifluoromethyl)phenyl)-N-tert-butylpyridine-2-sulfonamide as a light yellow solid (45 mg, 13%). MS+m/z: 489.9 (M+H)+

5-[4-(5-Amino-1H-[1,2,4]triazol-3-ylamino)-2-chloro-6-trifluoromethyl-phenyl]-pyridine-2-sulfonic acid (2,2,2-trifluoro-1,1-dimethyl-ethyl)-amide (Compound 25)

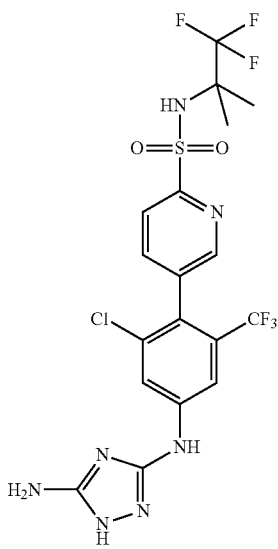 [SMILES: CC(C)(NS(=O)(=O)c1ccc(-c2c(Cl)cc(Nc3n[nH]c(N)n3)cc2C(F)(F)F)cn1)C(F)(F)F]

5-Bromo-pyridine-2-sulfonyl chloride

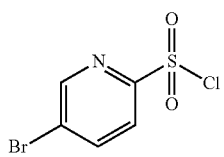 [SMILES: O=S(=O)(Cl)c1ccc(Br)cn1]

A mixture of crude 2-(benzylthio)-5-bromopyridine (prepared in Compound 2, 7.74 g, 27.6 mmol, Eq: 1.00), water (80.0 ml), and carbon tetrachloride (300 ml) was cooled to 0° C. in an ice bath and vigorously stirred while chlorine gas was bubbled slowly through the mixture. After 3 minutes the reaction mixture was saturated with chlorine and turned bright yellow green. Bubbling was continued for 10 minutes followed by 5 additional minutes of stirring under a chlorine blanket before the mixture was sparged of chlorine by bubbling argon into the solution for 10 minutes. The mixture was diluted with dichloromethane (100 ml) and the phases separated. The organic phase was washed with water (100 ml), a saturated sodium bicarbonate solution (100 ml) and brine and then dried over magnesium sulfate. The mixture was filtered and evaporated to give 5-bromopyridine-2-sulfonyl chloride as a semi-crystalline solid (4.34 g, 61%).

5-Bromo-pyridine-2-sulfonic acid (2,2,2-trifluoro-1,1-dimethyl-ethyl)-amide

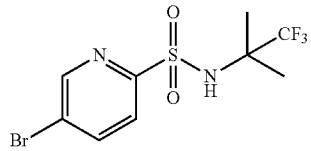 [SMILES: CC(C)(NS(=O)(=O)c1ccc(Br)cn1)C(F)(F)F]

To a solution of 5-bromopyridine-2-sulfonyl chloride (2.17 g, 6.34 mmol, Eq: 1) in dry pyridine (10 ml) was added 1,1,1-trifluoro-2-methylpropan-2-amine (806 mg, 6.34 mmol, Eq: 1) and the resulting mixture stirred at room temperature overnight. The mixture was evaporated and the residue absorbed onto silica and purified by flash chromatography (Analogix Intelliflash 310, Redisep Rf 40 g column, 0-30% ethyl acetate/hexane gradient). Like fractions were combined and evaporated to give 5-bromo-pyridine-2-sulfonic acid (2,2,2-trifluoro-1,1-dimethyl-ethyl)-amide as a light yellow solid (660 mg, 30%).

5-(4,4,5,5-Tetramethyl-[1,3,2]dioxaborolan-2-yl)-pyridine-2-sulfonic acid (2,2,2-trifluoro-1,1-dimethyl-ethyl)-amide

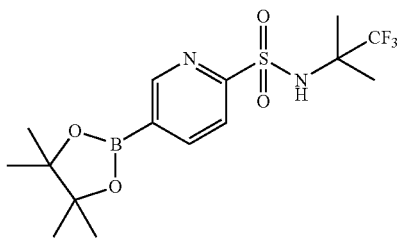 [SMILES: CC(C)(NS(=O)(=O)c1ccc(B2OC(C)(C)C(C)(C)O2)cn1)C(F)(F)F]

To a solution of 5-bromo-pyridine-2-sulfonic acid (2,2,2-trifluoro-1,1-dimethyl-ethyl)-amide (660 mg, 1.9 mmol, Eq: 1), 4,4,4',4',5,5,5',5'-octamethyl-2,2'-bi(1,3,2-dioxaborolane) (1.49 g, 5.87 mmol, Eq: 3.09), and potassium acetate (855 mg, 8.71 mmol, Eq: 4.58) in dioxane (20 ml) was added 1,1'-bis(diphenylphosphino)ferrocene-palladium(II)dichloride dichloromethane complex (149 mg, 203 μmol, Eq: 0.107) and the resulting mixture heated to 85° C. overnight under an argon atmosphere. The resulting mixture was cooled to room temperature, diluted with ethyl acetate (25 ml) and evaporated. The residue was taken up in ethyl acetate (50 ml), washed with brine (50 ml) and dried over sodium sulfate. The mixture was filtered and to the filtrate was added silica gel (~1.5 g). The mixture was evaporated and purified by flash chromatography (Analogix Intelliflash, RediSep Rf 24 g column, 10-50% ethyl acetate/hexane). Like fractions were combined and evaporated to give crude 5-(4,4,5,5-tetramethyl-[1,3,2]dioxaborolan-2-yl)-pyridine-2-sulfonic acid (2,2,2-trifluoro-1,1-dimethyl-ethyl)-amide as an off-white solid (637 mg, 70% pure by HNMR, 60%).

5-[4-(5-Amino-1H-[1,2,4]triazol-3-ylamino)-2-chloro-6-trifluoromethyl-phenyl]-pyridine-2-sulfonic acid (2,2,2-trifluoro-1,1-dimethyl-ethyl)-amide (Compound 25)

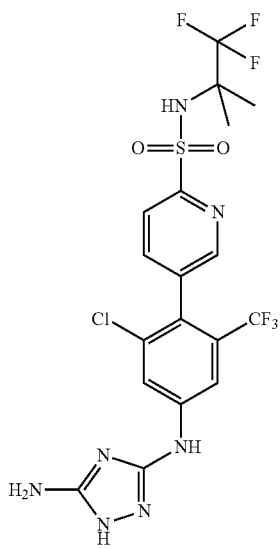 [SMILES: CC(C)(NS(=O)(=O)c1ccc(-c2c(Cl)cc(Nc3n[nH]c(N)n3)cc2C(F)(F)F)cn1)C(F)(F)F]

A mixture of N3-(4-bromo-3-chloro-5-(trifluoromethyl) phenyl)-1H-1,2,4-triazole-3,5-diamine Intermediate 1 (190 mg, 533 μmol, Eq: 1.00), 5-(4,4,5,5-tetramethyl-[1,3,2]dioxaborolan-2-yl)-pyridine-2-sulfonic acid (2,2,2-trifluoro-1,1-dimethyl-ethyl)-amide (300 mg, 533 μmol, Eq: 1.00) a 3M potassium carbonate solution (355 μl, 1.07 mmol, Eq: 2), dimethoxyethane (1 ml) p-dioxane (1 ml) and tetrakis(triphenylphosphine)palladium(0) (114 mg, 98.5 μmol, Eq: 0.185) was placed in a microwave reaction tube and degassed with argon under sonication for 15 minutes. The tube was sealed and the resulting mixture was heated in a microwave reactor to 128° C. and held at that temperature for 3 h. The reaction mixture was cooled and diluted with ethyl acetate (2 mL) and water (1 mL) and the phases separated. The aqueous phase was extracted with ethyl acetate (3×1 mL) and the combined organic phases were washed with brine and dried over sodium sulfate. The resulting mixture was filtered and evaporated to give a brown residue which was chromatographed on silica (Analogix Intelliflash 310, RediSep silica 24 g, 4-10% methanol/dichloromethane gradient). Like fractions were combined and evaporated and the residue purified by SFC chromatography (THAR/SFC/Waters Multigram II system eluted with 20% methanol/carbon dioxide at 70 ml/mn on a SILICA column 3×25 cm with detection at 220 nM and 35 degrees and 100 bar backpressure) to give 5-[4-(5-Amino-1H-[1,2,4]triazol-3-ylamino)-2-chloro-6-trifluoromethyl-phenyl]-pyridine-2-sulfonic acid (2,2,2-trifluoro-1,1-dimethyl-ethyl)-amide as an off white solid (22.4 mg, 8%). MS+m/z: 453.9 (M+H)$^+$ 4-[4-(5-Amino-1H-[1,2,4]triazol-3-ylamino)-2-chloro-6-trifluoromethyl-phenyl]-pyridine-2-sulfonic acid adamantan-1-ylamide (Compound 26)

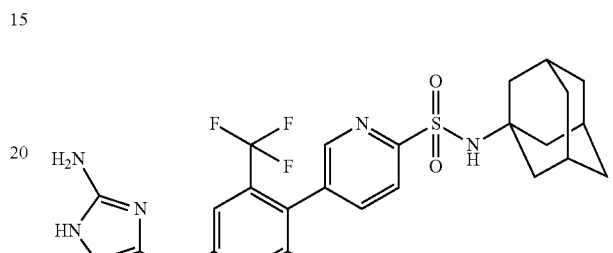

5-Bromo-pyridine-2-sulfonic acid adamantan-1-ylamide

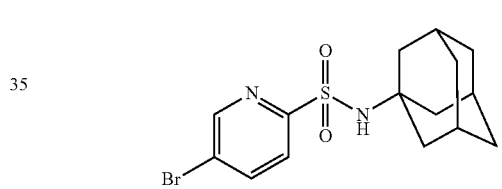

To a solution of 5-bromopyridine-2-sulfonyl chloride (prepared in example 3, 2.17 g, 6.34 mmol, Eq: 1) in pyridine (10 ml) was added 1-adamantamine (960 mg, 6.34 mmol, Eq: 1) and the resulting mixture stirred at room temperature overnight. The mixture was evaporated and the residue absorbed onto silica and purified by flash chromatography (Analogix Intelliflash 310, RedisepRf 40 g column, 0-30% ethyl acetate/hexane). Like fractions were combined and evaporated to give 5-bromo-pyridine-2-sulfonic acid adamantan-1-ylamide (900 mg, 38%).

5-(4,4,5,5-Tetramethyl-[1,3,2]dioxaborolan-2-yl)-pyridine-2-sulfonic acid adamantan-1-ylamide

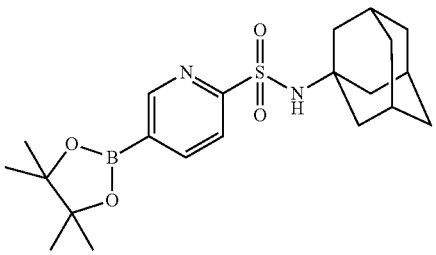 [SMILES: CC1(C)OB(c2ccc(S(=O)(=O)NC34CC5CC(CC(C5)C3)C4)nc2)OC1(C)C]

To a solution of 5-bromo-pyridine-2-sulfonic acid adamantan-1-ylamide (900 mg, 2.42 mmol, Eq: 1), bis(pinacolato)diboron (1.9 g, 7.49 mmol, Eq: 3.09), and potassium acetate (1.09 g, 11.1 mmol, Eq: 4.58) in dioxane was added 1,1'-bis(diphenylphosphino)ferrocene-palladium(II)dichloride dichloromethane complex (190 mg, 259 µmol, Eq: 0.107). The resulting mixture was heated to 85° C. overnight under an argon atmosphere. The resulting mixture was cooled to room temperature, diluted with ethyl acetate (25 ml) and evaporated. The residue was taken up in ethyl acetate (50 ml), washed with brine (50 ml) and dried over sodium sulfate. The mixture was filtered and to the filtrate was added silica gel (~1.5 g). The mixture was evaporated and purified by flash chromatography (Analogix Intelliflash, RediSep Rf 24 g column, 10-50% ethyl acetate/hexane). Like fractions were combined and evaporated to give crude 5-(4,4,5,5-tetramethyl-[1,3,2]dioxaborolan-2-yl)-pyridine-2-sulfonic acid adamantan-1-ylamide as a pale yellow solid (759 mg, 71% pure by HNMR, 53%).

4-[4-(5-Amino-1H-[1,2,4]triazol-3-ylamino)-2-chloro-6-trifluoromethyl-phenyl]-pyridine-2-sulfonic acid adamantan-1-ylamide (Compound 26)

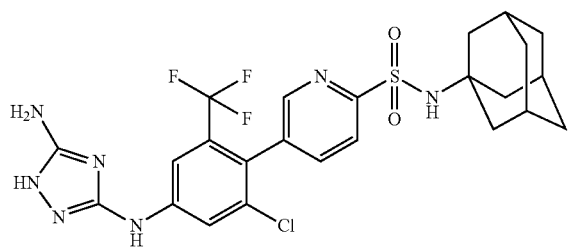 [SMILES: Nc1nc(Nc2cc(Cl)c(-c3ccc(S(=O)(=O)NC45CC6CC(CC(C6)C4)C5)nc3)c(C(F)(F)F)c2)n[nH]1]

A mixture of N3-(4-bromo-3-chloro-5-(trifluoromethyl)phenyl)-1H-1,2,4-triazole-3,5-diamine (256 mg, 717 µmol, Eq: 1), 5-(4,4,5,5-tetramethyl-[1,3,2]dioxaborolan-2-yl)-pyridine-2-sulfonic acid adamantan-1-ylamide (300 mg, 717 µmol, Eq: 1) a 3M potassium carbonate solution (478 µl, 1.43 mmol, Eq: 2), dimethoxyethane (1 ml) p-dioxane (1 ml) and tetrakis(triphenylphosphine)palladium(0) (114 mg, 98.5 µmol, Eq: 0.185) was placed in a microwave reaction tube and degassed with argon under sonication for 15 minutes. The tube was sealed and the resulting mixture was heated in a microwave reactor to 128° C. and held at that temperature for 3 h. The reaction mixture was cooled and diluted with ethyl acetate (2 mL) and water (1 mL) and the phases separated. The aqueous phase was extracted with ethyl acetate (3×1 mL) and the combined organic phases were washed with brine and dried over sodium sulfate. The resulting mixture was filtered and evaporated to give a brown residue which was chromatographed on silica (Analogix Intelliflash 310, RediSep silica 24 g, 4-10% methanol/dichloromethane gradient). Like fractions were combined and evaporated and the residue purified by SFC chromatography (THAR/SFC/Waters Multigram II system eluted with 20% methanol/carbon dioxide at 70 ml/mn on a SILICA column 3×25 cm with detection at 220 nM and 35 degrees and 100 bar backpressure) to give 4-[4-(5-amino-1H-[1,2,4]triazol-3-ylamino)-2-chloro-6-trifluoromethyl-phenyl]-pyridine-2-sulfonic acid adamantan-1-ylamide as a light yellow solid (44.4 mg, 11%). MS+m/z: 568 (M)+

N3-(2-chloro-4'-(4-methylpiperazin-1-yl)-6-(trifluoromethyl)biphenyl-4-yl)-1H-1,2,4-triazole-3,5-diamine (Compound 27)

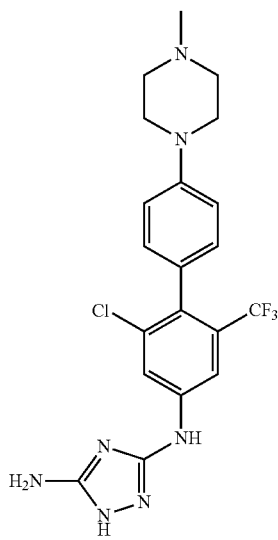 [SMILES: CN1CCN(c2ccc(-c3c(Cl)cc(Nc4n[nH]c(N)n4)cc3C(F)(F)F)cc2)CC1]

A mixture of N3-(4-bromo-3-chloro-5-(trifluoromethyl)phenyl)-1H-1,2,4-triazole-3,5-diamine Intermediate 1 (590 mg, 1.65 mmol, Eq: 1), 1-methyl-4-(4-(4,4,5,5-tetramethyl-1,3,2-dioxaborolan-2-yl)phenyl)piperazine (500 mg, 1.65 mmol, Eq: 1) a 3M potassium carbonate solution (1.1 ml, 3.31 mmol, Eq: 2), dimethoxyethane (1.67 ml) p-dioxane (1.67 ml) and tetrakis(triphenylphosphine)palladium(0) (354 mg, 306 µmol, Eq: 0.185) was placed in a microwave reaction tube and degassed with argon under sonication for 15 minutes. The tube was sealed and the resulting mixture was heated in a microwave reactor to 128° C. and held at that temperature for 3 h. The reaction mixture was cooled, the tube opened and 1-methyl-4-(4-(4,4,5,5-tetramethyl-1,3,2-dioxaborolan-2-yl)phenyl)piperazine (200 mg, 1.65 mmol, Eq: 1) was added. The tube was resealed and heated in a microwave reactor to 128° C. for 2 h. The reaction mixture was cooled and diluted with ethyl acetate and the organic phase washed with brine and dried over magnesium sulfate. The mixture was filtered and evaporated to give a brown residue which was chromatographed on silica (Analogix Intelliflash 310, RediSep silica 24 g, 4-10% methanol/dichloromethane gradient). Like fractions were combined and evaporated and the residue purified by HPLC (Gilson, Supelcosil ABZ+Plus column, 25 cm×21.2 mm 12 µM, 25-100% acetonitrile/water gradient 0.3% formic acid) Like fractions were combined and lyophilized to give N3-(2-chloro-4'-(4-methylpiperazin-1-yl)-6-(trifluoromethyl)biphenyl-4-yl)-1H-1,2,4-triazole-3,5-diamine as a white lyophilized solid (20.23 mg, 44.8 µmol, 2.71%). MS +m/z: 543.0 (M+H)+

1-[4-(5-Amino-1H-[1,2,4]triazol-3-ylamino)-phenyl]-1H-pyridin-2-one (Compound 28)

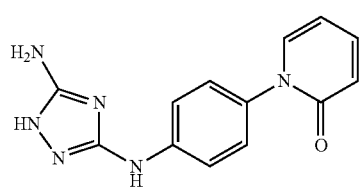

1-(4-Nitro-phenyl)-1H-pyridin-2-one

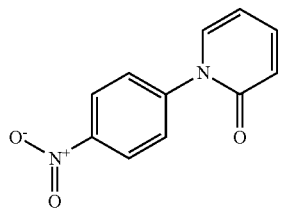 [SMILES: O=c1ccccn1-c1ccc([N+](=O)[O-])cc1]

In a 50 mL round-bottomed flask, potassium tert-butoxide (885 mg, 7.89 mmol, Eq: 1.50) and pyridin-2(1H)-one (500 mg, 5.26 mmol, Eq: 1.00) were combined with DMF (10.0 mL) to give a light brown solution at 0° C. under nitrogen. 1-fluoro-4-nitrobenzene (742 mg, 5.26 mmol, Eq: 1.00) was added. The reaction was stirred overnight at room temperature. The reaction mixture was diluted with CH$_2$Cl$_2$ (50 mL), washed with H$_2$O (25 mL) and brine (25 mL). The organic layer was dried over anhydrous MgSO$_4$, filtered and volatiles were removed under reduced pressure to yield an oil from which the compound was isolated by column chromatography (Hexanes/EtOAc=70/30) to give an off-white solid 1 g (88%). MH+217.1

1-(4-Amino-phenyl)-1H-pyridin-2-one

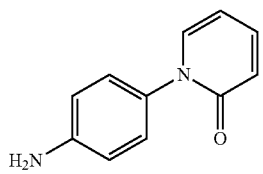 [SMILES: Nc1ccc(-n2ccccc2=O)cc1]

In a 100 mL round bottle, 1-(4-nitrophenyl)pyridin-2(1H)-one (1.0 g, 4.63 mmol, Eq: 1.00) and zinc (1.51 g, 23.1 mmol, Eq: 5.00) were combined with a solution of saturated NH$_4$Cl aqueous solution/THF (1:1) (50 ml), the mixture was stirred at for overnight. Filter out the solid, extracted with CH$_2$Cl$_2$ (50 mL×2), the organic layer was dried over anhydrous Na$_2$SO$_4$; the solution was concentrated under vacuum to afford the crude product 740 mg (86%). MH+188.3

1-(4-Isothiocyanato-phenyl)-1H-pyridin-2-one

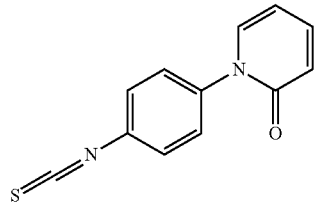 [SMILES: O=c1ccccn1-c1ccc(N=C=S)cc1]

In a 100 mL round-bottomed flask, di(1H-imidazol-1-yl)methanethione (718 mg, 4.03 mmol, Eq: 1.5) was combined with CH$_2$Cl$_2$ (30 mL) to give a colorless solution. 1-(4-Aminophenyl)pyridin-2(1H)-one (500 mg, 2.69 mmol, Eq: 1.00) in CH$_2$Cl$_2$ (20 mL) was added dropwise at 0° C. The reaction was allowed to warm to room temperature, and allowed to stir overnight. Concentrate the solution, the compound was isolated by column chromatography (Hexanes/EtOAc=80/20) to give the product 580 mg (95%). MH+228.9

Methylsulfanyl-[4-(2-oxo-2H-pyridin-1-yl)-phenylamino]-methyl-cyanamide

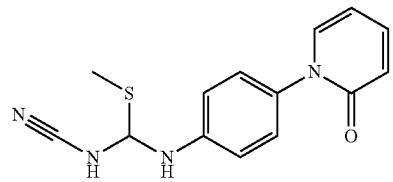 [SMILES: CSC(NC#N)Nc1ccc(-n2ccccc2=O)cc1]

In a 100 mL round-bottomed flask, 1-(4-isothiocyanato-phenyl)pyridin-2(1H)-one (580 mg, 2.54 mmol, Eq: 1.00) in MeOH (20 mL), sodium hydrogencyanamide (184 mg, 2.87 mmol, Eq: 1.13) was added. The suspension turned to clear after a few minutes, the reaction was allowed to stir at room temperature for 1 hour, iodomethane (721 mg, 5.08 mmol, Eq: 2) was added, the reaction mixture was allowed to stir at room temperature overnight. Concentrate the solution, the compound was isolated by column chromatography (CH$_2$Cl$_2$/MeOH=95/5) to give an off-white solid 120 mg (17%). MH+284.9

1-[4-(5-Amino-1H-[1,2,4]triazol-3-ylamino)-phenyl]-1H-pyridin-2-one (Compound 28)

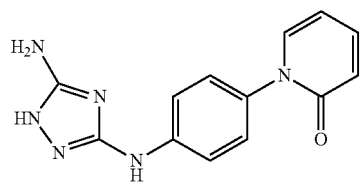 [SMILES: Nc1nc(Nc2ccc(-n3ccccc3=O)cc2)n[nH]1]

In a 100 mL round-bottomed flask, methylsulfanyl-[4-(2-oxo-2H-pyridin-1-yl)-phenylamino]-methyl-cyanamide (120 mg, 419 μmol, Eq: 1.00) in EtOH (30 mL), hydrazine (134 mg, 4.19 mmol, Eq: 10.00) was added. The reaction was heated to 65° C. for 3 hours. The reaction mixture was concentrated, added H₂O (20 mL) to the residue, filtered out the solid and washed the solid with H₂O (30 mL) and CH₂Cl₂ (10 mL), air-dried the solid overnight to give an off-white solid 36 mg (32%). MH+268.9

1-[4-(5-Amino-1H-[1,2,4]triazol-3-ylamino)-2-chloro-phenyl]-1H-pyridin-2-one (Compound 29)

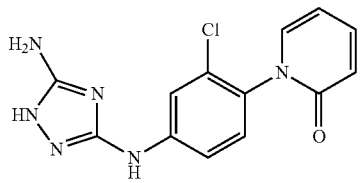

1-(2-Chloro-4-nitro-phenyl)-1H-pyridin-2-one

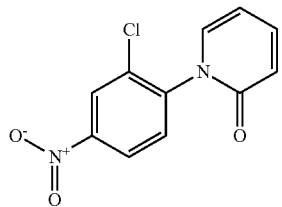 [SMILES: O=c1ccccn1-c1ccc([N+](=O)[O-])cc1Cl]

In a 50 mL round-bottomed flask, potassium tert-butoxide (7.08 g, 63.1 mmol, Eq: 1.50) and pyridin-2(1H)-one (4 g, 42.1 mmol, Eq: 1.00) were combined with DMF (50.0 mL) to give a light brown solution at 0° C. under nitrogen. N2. 2-chloro-1-fluoro-4-nitrobenzene (7.38 g, 42.1 mmol, Eq: 1.00) was added. The reaction was stirred overnight at room temperature. The reaction mixture was diluted with CH₂Cl₂ (50 mL), washed with H₂O (25 mL) and brine (25 mL). The organic layer was dried over anhydrous MgSO₄, filtered and volatiles were removed under reduced pressure to yield an oil from which the compound was isolated by column chromatography (Hexanes/EtOAc=70/30) to give an off-white solid 4.07 g (39%). MH+250.9

1-(4-Amino-2-chloro-phenyl)-1H-pyridin-2-one

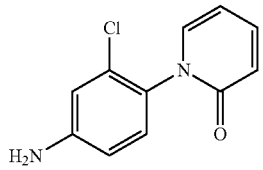 [SMILES: Nc1ccc(-n2ccccc2=O)c(Cl)c1]

In a 100 mL round bottle, 1-(2-chloro-4-nitrophenyl)pyridin-2(1H)-one (4.07 g, 16.2 mmol, Eq: 1.00) and zinc (5.31 g, 81.2 mmol, Eq: 5.00) were combined with a solution of saturated NH₄Cl aqueous solution/THF (1:1) (50 mL), the mixture was stirred at for overnight. Filter out the solid, extracted with CH₂Cl₂ (50 mL×2), the organic layer was dried over anhydrous Na₂SO₄; the solution was concentrated under vacuum to afford the crude product 3.3 g (92%). MH+221.0

1-(2-Chloro-4-isothiocyanato-phenyl)-1H-pyridin-2-one

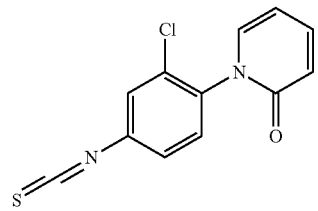

In a 100 mL round-bottomed flask, di(1H-imidazol-1-yl)methanethione (2.42 g, 13.6 mmol, Eq: 1.5) was combined with CH₂Cl₂ (30 mL) to give a colorless solution. 1-(4-amino-2-chlorophenyl)pyridin-2(1H)-one (2 g, 9.06 mmol, Eq: 1.00) in CH₂Cl₂ (20 mL) was added dropwise at 0° C. The reaction was allowed to warm to room temperature, and allowed to stir overnight. Concentrate the solution, the compound was isolated by column chromatography (Hexanes/EtOAc=50/50) to give the product 1.1 g (46%). MH+262.9

[3-Chloro-4-(2-oxo-2H-pyridin-1-yl)-phenylamino]-methylsulfanyl-methyl-cyanamide

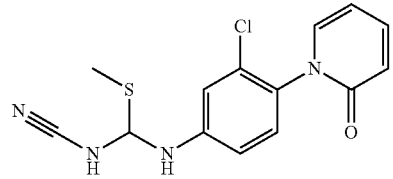 [SMILES: CSC(NC#N)Nc1ccc(-n2ccccc2=O)c(Cl)c1]

In a 100 mL round-bottomed flask, 1-(2-chloro-4-isothiocyanatophenyl)pyridin-2(1H)-one (1.1 g, 4.19 mmol, Eq: 1.00) in MeOH (20 mL), sodium hydrogencyanamide (303 mg, 4.73 mmol, Eq: 1.13) was added. The suspension turned to clear after a few minutes, the reaction was allowed to stir at room temperature for 1 hour, iodomethane (1.19 g, 8.37 mmol, Eq: 2) was added, the reaction mixture was allowed to stir at room temperature overnight. Concentrate the solution, the compound was isolated by column chromatography (CH₂Cl₂/MeOH=95/5) to give an off-white solid 590 mg (44%). MH+320.9

1-[4-(5-Amino-1H-[1,2,4]triazol-3-ylamino)-2-chloro-phenyl]-1H-pyridin-2-one (Compound 29)

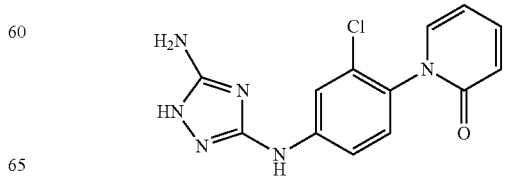

In a 100 mL round-bottomed flask, [3-chloro-4-(2-oxo-2H-pyridin-1-yl)-phenylamino]-methylsulfanyl-methyl-cyanamide (590 mg, 1.84 mmol, Eq: 1.00) in EtOH (30 mL), hydrazine (589 mg, 18.4 mmol, Eq: 10.00) was added. The reaction was heated to 65° C. for 3 hours. The reaction mixture was concentrated, added H₂O (20 mL) to the residue, filtered out the solid and washed the solid with H₂O (30 mL) and CH₂Cl₂ (10 mL), air-dried the solid overnight to give an off-white solid 494 mg (89%). MH+303.0

1-[4-(5-Amino-1H-[1,2,4]triazol-3-ylamino)-2,6-dichloro-phenyl]-1H-pyridin-2-one (Compound 30)

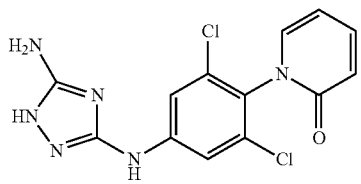

1-(2,6-Dichloro-4-nitro-phenyl)-1H-pyridin-2-one

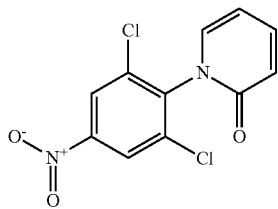 [SMILES: O=c1ccccn1-c1c(Cl)cc([N+](=O)[O-])cc1Cl]

In a 50 mL round-bottomed flask, potassium tert-butoxide (3.54 g, 31.5 mmol, Eq: 1.50) and pyridin-2(1H)-one (2 g, 21.0 mmol, Eq: 1.00) were combined with DMF (25.0 ml) to give a light brown suspension at 0° C. under nitrogen. 1,3-dichloro-2-fluoro-5-nitrobenzene (4.42 g, 21.0 mmol, Eq: 1.00) was added. The reaction was stirred overnight at room temperature. The reaction mixture was diluted with CH₂Cl₂ (50 mL), washed with H₂O (25 mL) and brine (25 mL). The organic layer was dried over anhydrous MgSO₄, filtered and volatiles were removed under reduced pressure to yield an oil from which the compound was isolated by column chromatography (Hexanes/EtOAc=70/30) to give an off-white solid 2.8 g (47%). MH+284.9

1-(4-Amino-2,6-dichloro-phenyl)-1H-pyridin-2-one

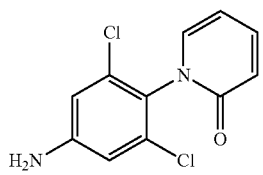 [SMILES: Nc1cc(Cl)c(-n2ccccc2=O)c(Cl)c1]

In a 100 mL round bottle, 1-(2,6-dichloro-4-nitrophenyl)pyridin-2(1H)-one (2.8 g, 9.82 mmol, Eq: 1.00) and zinc (3.21 g, 49.1 mmol, Eq: 5.00) were combined with a solution of saturated NH₄Cl aqueous solution/THF (1:1) (50 mL), the mixture was stirred at for overnight. Filter out the solid, extracted with CH₂Cl₂ (50 mL×2), the organic layer was dried over anhydrous Na₂SO₄; the solution was concentrated under vacuum to afford the crude product 1.3 g (50%). MH+255.9

1-(2,6-Dichloro-4-isothiocyanato-phenyl)-1H-pyridin-2-one

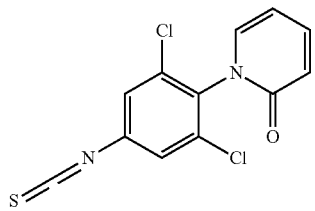

In a 100 mL round-bottomed flask, di(1H-imidazol-1-yl)methanethione (1.26 g, 7.06 mmol, Eq: 1.5) was combined with CH₂Cl₂ (30 mL) to give a colorless solution. 1-(4-amino-2,6-dichlorophenyl)-pyridin-2(1H)-one (1.2 g, 4.7 mmol, Eq: 1.00) in CH₂Cl₂ (20 mL) was added dropwise at 0° C. The reaction was allowed to warm to room temperature, and allowed to stir overnight. Concentrate the solution, the compound was isolated by column chromatography (Hexanes/EtOAc=50/50) to give the product 520 mg (37%). MH+296.8

[3,5-Dichloro-4-(2-oxo-2H-pyridin-1-yl)-phenylamino]-methylsulfanyl-methyl-cyanamide

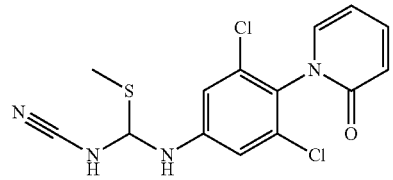 [SMILES: CSC(NC#N)Nc1cc(Cl)c(-n2ccccc2=O)c(Cl)c1]

In a 100 mL round-bottomed flask, 1-(2,6-dichloro-4-isothiocyanatophenyl)pyridin-2(1H)-one (520 mg, 1.75 mmol, Eq: 1.00) in MeOH (20 mL), sodium hydrogencyanamide (127 mg, 1.98 mmol, Eq: 1.13) was added. The suspension turned to clear after a few minutes, the reaction was allowed to stir at room temperature for 1 hour, iodomethane (497 mg, 3.5 mmol, Eq: 2) was added, the reaction mixture was allowed to stir at room temperature overnight. Concentrate the solution, the compound was isolated by column chromatography (CH₂Cl₂/MeOH=95/5) to give an off-white solid 200 mg (32%). MH+352.9

1-[4-(5-Amino-1H-[1,2,4]triazol-3-ylamino)-2,6-dichloro-phenyl]-1H-pyridin-2-one (Compound 30)

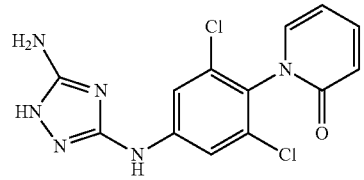

In a 100 mL round-bottomed flask, [3,5-dichloro-4-(2-oxo-2H-pyridin-1-yl)-phenylamino]-methylsulfanyl-methyl-cyanamide (200 mg, 563 μmol, Eq: 1.00) in EtOH (30 mL), hydrazine (180 mg, 5.63 mmol, Eq: 10.00) was added. The reaction was heated to 65° C. for 3 hours. The reaction mixture was concentrated, added H₂O (20 mL) to the residue, filtered out the solid and washed the solid with H₂O (30 mL) and CH₂Cl₂ (10 mL), air-dried the solid overnight to give an off-white solid 36 mg (19%). MH+336.9

N3-(3,5-dichloro-4-(1,4,5,6-tetrahydropyrimidin-2-yl)phenyl)-1H-1,2,4-triazole-3,5-diamine. trifluoroacetic salt (Compound 31)

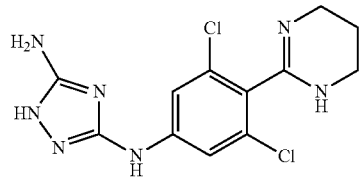 [SMILES: Nc1nc(Nc2cc(Cl)c(C3=NCCCN3)c(Cl)c2)n[nH]1]

2,6-dichloro-4-nitrobenzonitrile

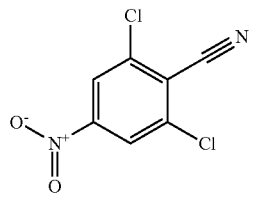 [SMILES: N#Cc1c(Cl)cc([N+](=O)[O-])cc1Cl]

A solution of copper(i) cyanide (2.6 g, 29.0 mmol, Eq: 2) in DMSO (5 mL) was heated at 60o for 1 hr. Tert-butyl nitrite (5.98 g, 6.9 ml, 58.0 mmol, Eq: 4.00) and a solution 2,6-dichloro-4-nitroaniline (3 g, 14.5 mmol, Eq: 1.00) in DMSO (5 mL) was added and the reaction was stirred for 3 hr. The reaction mixture was poured into ice water and extracted with ethyl acetate 3×. The organic extract was washed with brine and dried over sodium sulfate. Chromatography (200 g Analogix, 100% hex to 5% EtOAc/hex) gave 515 mg (16%) of desired product as a light brown solid.

4-amino-2,6-dichlorobenzonitrile

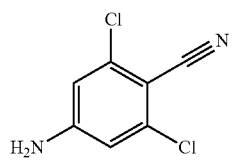

A solution of 2,6-dichloro-4-nitrobenzonitrile (2.46 g, 11.3 mmol, Eq: 1.00), iron (3.17 g, 56.7 mmol, Eq: 5) and ammonium chloride (6.06 g, 113 mmol, Eq: 10) in methanol (30 mL)/water (10 mL) was heated at reflux o/n. TLC shows incomplete reaction. Continued heating at 100 deg for 6 hr, then 60 deg overnight. The reaction mixture was filtered over Celite. The filtrate was suspended in ethyl acetate to give insoluble solid. The slurry was concentrated to dryness, suspended in water, filtered, and rinsed with water. The solid was transferred to a round bottom flask, suspended in benzene, and concentrated. An additional portion of benzene was added and concentrated once more to give 1.37 g (65%) of desired product as a light brown solid.

2,6-dichloro-4-isothiocyanatobenzonitrile

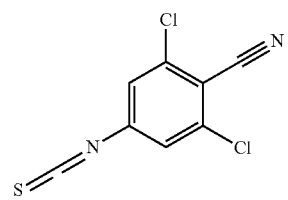

A suspension of 4-amino-2,6-dichlorobenzonitrile (500 mg, 2.67 mmol, Eq: 1.00), thiophosgene (1.35 g, 900 μl, 11.7 mmol, Eq: 4.39), triethylamine (875 mg, 1.2 ml, 8.64 mmol, Eq: 3.23) in benzene (30 ml) was heated at reflux overnight. The brown reaction mixture was concentrated and chromatographed (80 g Analogix, 0 to 5% ethyl acetate/hexane) to give 436 mg (71%) of desired product as a light brown solid.

(Z)-methyl N'-cyano-N-(3,5-dichloro-4-cyanophenyl)carbamimidothioate

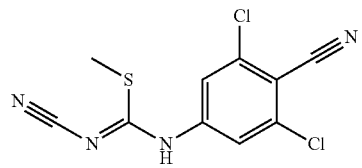 [SMILES: CS/C(=N\C#N)Nc1cc(Cl)c(C#N)c(Cl)c1]

Sodium methoxide (0.5M in methanol) (5.7 ml, 2.85 mmol, Eq: 1.22) was added to cyanamide (108 mg, 2.58 mmol, Eq: 1.1). After 15 minutes, the solution was added to a solution of 2,6-dichloro-4-isothiocyanatobenzonitrile (537 mg, 2.34 mmol, Eq: 1.00) in methanol (5 mL). After 1 hr, methyl iodide (704 mg, 310 μl, 4.96 mmol, Eq: 2.11) was added and the reaction was stirred overnight at room temperature. The resulting suspension was filtered and dried to give 43 mg of desired product as a gray solid. The filtrate was concentrated and chromatographed (40 g Analogix, 50% EtOAc/hex to 75% EtOAc/hex) to give 191 mg of desired product as a yellow solid. The solids were combined to give 234 mg (35%) of desired product.

4-(5-Amino-1H-[1,2,4]triazol-3-ylamino)-2,6-dichloro-benzonitrile

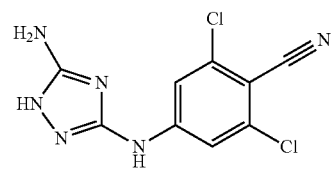

A solution of (Z)-methyl N'-cyano-N-(3,5-dichloro-4-cyanophenyl)carbamimidothioate (234 mg, 821 µmol, Eq: 1.00) and hydrazine (263 mg, 258 µl, 8.21 mmol, Eq: 10) in ethanol (10 mL) was heated at 65° C. o/n. The reaction mixture was concentrated and chromatographed (23 Supelco, 100% DCM to 5% to 10% MeOH/DCM to give 156 mg (71%) of desired product as an off-white solid.

$^1$H NMR (300 MHz, DMSO) δ: 11.55 (s, 1H), 9.99 (s, 1H), 7.74 (s, 2H), 6.14 (s, 2H) ppm N3-(3,5-dichloro-4-(1,4,5,6-tetrahydropyrimidin-2-yl)phenyl)-1H-1,2,4-triazole-3,5-diamine. trifluoroacetic salt (Compound 31)

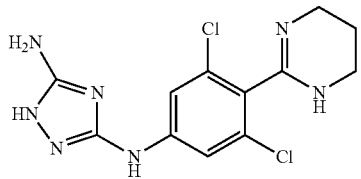 [SMILES: Nc1nc(Nc2cc(Cl)c(C3=NCCCN3)c(Cl)c2)n[nH]1]

A mixture of 4-(5-amino-1H-1,2,4-triazol-3-ylamino)-2,6-dichlorobenzonitrile (85 mg, 316 µmol, Eq: 1.00), propane-1,3-diamine (70.2 mg, 948 µmol, Eq: 3) and 4-methylbenzenesulfonic acid, monohydrate (60.1 mg, 316 µmol, Eq: 1.00) was stirred at 210° C. for 5 h.

The reaction mixture is cooled down and the resulting solid was dried in vacuo then purified by reverse phase HLPC to afford 46 mg (33%) of the desired product as a white solid. MS –m/z: 438.0 (M–H)$^-$ 5-(4-(5-amino-1H-1,2,4-triazol-3-ylamino)-2-chloro-6-(trifluoromethyl)phenyl)-N-methylpicolinamide (Compound 32)

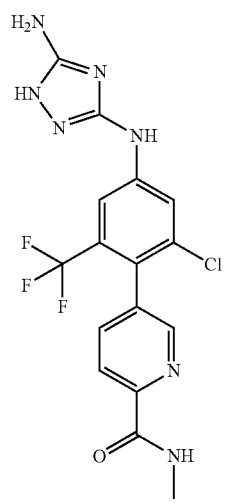 [SMILES: CNC(=O)c1ccc(-c2c(Cl)cc(Nc3n[nH]c(N)n3)cc2C(F)(F)F)cn1]

A mixture of N3-(4-bromo-3-chloro-5-(trifluoromethyl)phenyl)-1H-1,2,4-triazole-3,5-diamine Intermediate 1 (200 mg, 561 µmol, Eq: 1.00), N-methyl-5-(4,4,5,5-tetramethyl-1,3,2-dioxaborolan-2-yl)picolinamide [945863-21-8] (198 mg, 757 µmol, Eq: 1.35) and (triphenylphosphine)palladium(0) (64.8 mg, 56.1 µmol, Eq: 0.1) was degassed (vacuum/nitrogen cycles) then degassed dry dioxane (1.85 ml) (nitrogen bubbling with sonication) and a degassed (nitrogen bubbling with sonication) 2M solution of sodium carbonate in water (561 µl, 1.12 mmol, Eq: 2) were added. The reaction mixture was sealed and stirred at 105° C. for 18 h. The reaction mixture was adsorbed unto silica (1 g), concentrated and purified on silica gel (silica 24 g, dichloromethane/methanol 97:3 to 70:30). One fraction was isolated and dried in vacuo to afford 45 mg (20%) of the desired product as a yellow semi-solid solid.

MS+m/z: 411.9 (M+H)$^+$

N3-(3,5-dichloro-4-(pyridazin-4-yl)phenyl)-1H-1,2,4-triazole-3,5-diamine (Compound 33)

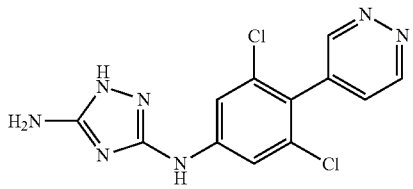 [SMILES: Nc1nc(Nc2cc(Cl)c(-c3ccnnc3)c(Cl)c2)n[nH]1]

To a degassed (cycle vacuum/nitrogen) mixture of N3-(4-bromo-3,5-dichlorophenyl)-1H-1,2,4-triazole-3,5-diamine Intermediate 2 (80 mg, 248 µmol, Eq: 1.00) and Pd(PPh$_3$)$_2$Cl$_2$ (17.4 mg, 24.8 µmol, Eq: 0.1) was added degassed (nitrogen bubbling with sonication) dry dimethylformamide (3 ml) followed by 4-(tributylstannyl)pyridazine (229 mg, 195 µl, 619 µmol, Eq: 2.5). The reaction mixture was further degassed (vacuum/nitrogen cycles).

The reaction mixture was stirred at 100° C. over 3 days then adsorbed unto silica (0.7 g) and purified on silicagel (column 12 g, dichloromethane/methanol 100:0 to 60:40). 37 mg of a brown solid was obtained. The compound was triturated in methanol (1 mL) then washed with methanol (2×1 mL). The solid was dried in vacuo to afford 30 mg (38%) of the desired product as a brown-red solid.

NMR (300 MHz, DMSO d$^6$): 11.38 (1H, s); 9.45 (1H, s); 9.34 (1H, dd, J=1, 6 Hz); 9.22 (1H, broad s); 7.78 (2H, s); 7.74 (1H, dd, J=3, 6 Hz); 6.06 (2H, s).

1-{3-[4-(5-Amino-1H-[1,2,4]triazol-3-ylamino)-2,6-dichloro-phenyl]-thiophen-2-yl}-ethanone (Compound 34)

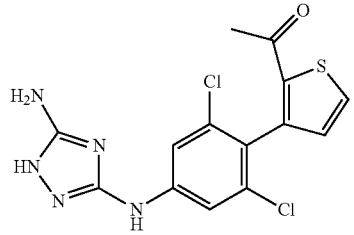 [SMILES: CC(=O)c1sccc1-c1c(Cl)cc(Nc2n[nH]c(N)n2)cc1Cl]

To a solution of N-3-(4-bromo-3,5-dichlorophenyl)-1H-1,2,4-triazole-3,5-diamine Intermediate 2 (80.7 mg, 0.25 mmol, Eq: 1.00) in dioxane (1.25 ml) was added tetrakis (triphenylphosphine)palladium(0) (23.1 mg, 20 µmol, Eq: 0.08), potassium carbonate (167 µl, 3M, Eq: 2), and 2-acetyl-3-thienylboronic acid (85 mg, 0.5 mmol Eq: 2). The mixture was degassed twice under Nitrogen, then was heated at 100° C. for 16 hours. After being cooled to room temperature, the solvent was removed in vacuo. To the crude product was added a few drops of acetic acid, followed by addition of mixture of MeOH/CH3CN/H2O(45%/45%/10%)(2 ml). The resulting suspension was centrifuged, and the solution was separated and purified by reverse phase HPLC (0.1% HOAc in acetonitrile and water). Product fractions were collected and lyophilized to afford 1-{3-[4-(5-amino-1H-[1,2,4]triazol-3-ylamino)-2,6-dichloro-phenyl]-thiophen-2-yl}-ethanone (28.5 mg, 31%) as a white solid. MS m/z: 369 (M+H)+. The following compounds 35-44 were all prepared in an analogous manner to example 34:

N-3-(3,5-Dichloro-4-(pyridin-4-yl)phenyl)-1H-1,2,4-triazole-3,5-diamine (Compound 35)

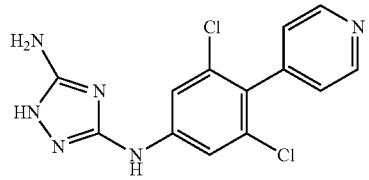 [SMILES: Nc1nc(Nc2cc(Cl)c(-c3ccncc3)c(Cl)c2)n[nH]1]

Starting from Pyridin-4-ylboronic acid, yield=13%, MS m/z 322 (M+H)

N-3-[3,5-Dichloro-4-(5-chloro-thiophen-2-yl)-phenyl]-1H-[1,2,4]triazole-3,5-diamine (Compound 36)

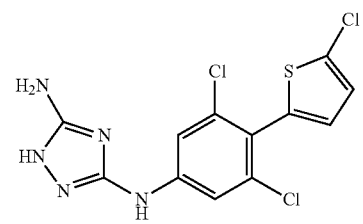 [SMILES: Nc1nc(Nc2cc(Cl)c(-c3ccc(Cl)s3)c(Cl)c2)n[nH]1]

Starting from 5-Chlorothiophene-2-boronic acid, yield=2%, MS m/z 362 (M+H)

N-3-(3,5-Dichloro-4-pyridin-3-yl-phenyl)-1H-[1,2,4]triazole-3,5-diamine (Compound 37)

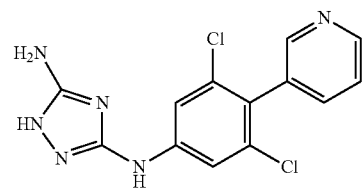 [SMILES: Nc1nc(Nc2cc(Cl)c(-c3cccnc3)c(Cl)c2)n[nH]1]

Starting from Pyridine-3-boronic acid, yield=15%, MS m/z 322 (M+H)

N-3-[3,5-Dichloro-4-(1H-pyrazol-3-yl)-phenyl]-1H-[1,2,4]triazole-3,5-diamine (Compound 38)

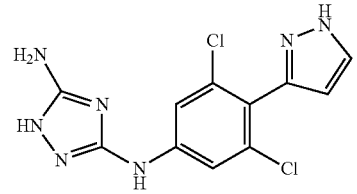 [SMILES: Nc1nc(Nc2cc(Cl)c(-c3cc[nH]n3)c(Cl)c2)n[nH]1]

Starting from Pyrazole-3-boronic acid, yield=1%, MS m/z 311 (M+H)

N-3-(3,5-Dichloro-4-pyrimidin-5-yl-phenyl)-1H-[1,2,4]triazole-3,5-diamine (Compound 39)

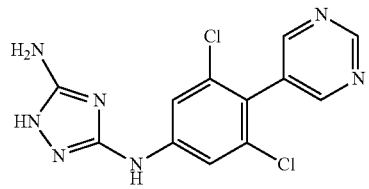 [SMILES: Nc1nc(Nc2cc(Cl)c(-c3cncnc3)c(Cl)c2)n[nH]1]

Starting from Pyrimidine-5-boronic acid, yield=4%, MS m/z 323 (M+H)

N-3-[3,5-Dichloro-4-(2-methoxy-pyrimidin-5-yl)-phenyl]-1H-[1,2,4]triazole-3,5-diamine (Compound 40)

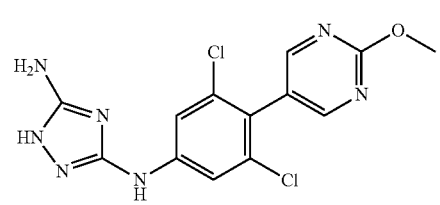 [SMILES: COc1ncc(-c2c(Cl)cc(Nc3n[nH]c(N)n3)cc2Cl)cn1]

Starting from 2-Methoxypyrimidine-5-boronic acid, yield=26%, MS m/z 353 (M+H)

N-3-[3,5-Dichloro-4-(6-trifluoromethyl-pyridin-3-yl)-phenyl]-1H-[1,2,4]triazole-3,5-diamine (Compound 41

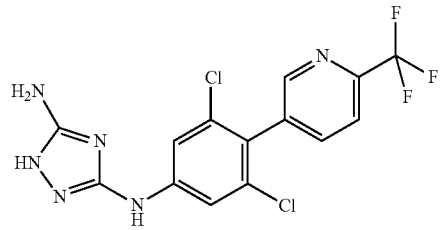 [SMILES: Nc1nc(Nc2cc(Cl)c(-c3ccc(C(F)(F)F)nc3)c(Cl)c2)n[nH]1]

Starting from 2-Trifluoromethyl-5-pyridineboric acid, yield=61%, MS m/z 390 (M+H)

N-3-[3,5-Dichloro-4-(1-methyl-3-trifluoromethyl-1H-pyrazol-4-yl)-phenyl]-1H-[1,2,4]triazole-3,5-diamine (Compound 42)

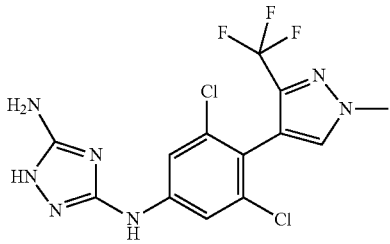 [SMILES: Cn1cc(-c2c(Cl)cc(Nc3n[nH]c(N)n3)cc2Cl)c(C(F)(F)F)n1]

Starting from 1-Methyl-3-trifluoromethylpyrazole-4-boronic acid, yield=3%, MS m/z 393 (M+H)

N-3-[3,5-Dichloro-4-(5-chloro-pyridin-3-yl)-phenyl]-1H-[1,2,4]triazole-3,5-diamine (Compound 43)

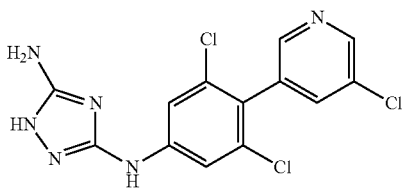 [SMILES: Nc1nc(Nc2cc(Cl)c(-c3cncc(Cl)c3)c(Cl)c2)n[nH]1]

Starting from 5-Chloropyridine-3-boronic acid, yield=31%, MS m/z 357 (M+H)

N-3-[3,5-Dichloro-4-(6-methoxy-pyridin-2-yl)-phenyl]-1H-[1,2,4]triazole-3,5-diamine (Compound 44)

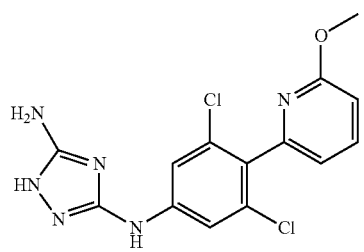 [SMILES: COc1cccc(-c2c(Cl)cc(Nc3n[nH]c(N)n3)cc2Cl)n1]

Starting from 6-Methoxypyridine-2-boronic acid, yield=1%, MS m/z 352 (M+H)

Biological Examples

Determination of compounds HCV GT1b and GT1a entry inhibitory activity using the pseudotyped HCV particle (HCVpp) reporter assay.

Mammalian expression plasmids for the generation of pseudotyped virus particles.

Plasmids expressing HCV E1 and E2 envelope proteins of GT1a H77 strain (Proc Natl Acad Sci USA 1997 94:8738-43) or GT1b Con1 strain (Science 1999 285:110-3) were constructed by cloning the nucleic acids encoding the last 60 amino acids of HCV core protein and all of the HCV E1 and E2 proteins into pcDNA3.1(+) vector. Plasmid pVSV-G expressing the glycoprotein G of the vesicular stomatitis virus (VSV G) is from Clontech (cat #631530). The HIV packaging construct expressing the firefly luciferase reporter gene was modified based on the envelope defective pNL.4.3.Luc-R$^-$.E$^-$ vector (Virology 1995 206:935-44) by further deleting part of the HIV envelope protein.

Generation of pseudotyped virus particles in transiently transfected HEK-293T cells.

Pseudotyped HCV GT1a and GT1b particles (HCVpp) and the pseudotyped VSV G particles (VSVpp) were generated from transiently transfected HEK-293T cells (ATCC cat# CRL-573). For generating HCVpp, the HEK-293T cells were transfected with equal amounts of plasmids expressing the HCV envelope proteins and the HIV packaging genome by using polyethylenimine (Polysciences cat#23966) as transfection reagent. For generating VSVpp, the HEK-293T cells were transfected with equal amounts of plasmids expressing VSV G and the HIV packaging genome by using polyethylenimine. 24 hours after the transfection, the cell culture medium containing the transfection mixture was replaced with fresh Dulbecco's Modified Eagle Medium (DMEM-Glutamax™-I; Invitrogen cat #10569-010) supplemented with 10% Fetal Bovine Serum (Invitrogen cat #10082-147) and 2 mM L-glutamine (Invitrogen cat #25030-081). The supernatant was collected 48 hours after the transfection and filtered through a sterile 0.45 μm filter. Aliquots of the supernatant was frozen and stored at −80° C. until use.

Huh7-high CD81 cells with high CD81 expression level were enriched by flow cytometry sorting using FITC-labeled CD81 antibody JS-81 (BD Biosciences cat#561956) to allow more efficient HCV entry. The Huh7-high CD81 cells were cultured in Dulbecco's Modified Eagle Medium (DMEM-Glutamax™-I; Invitrogen cat #10569-010). The medium was supplemented with 10% Fetal Bovine Serum (Invitrogen cat #10082-147) and 1% penicillin/streptomycin (Invitrogen cat #15070-063). Cells were maintained at 37° C. in a humidified 5% CO$_2$ atmosphere.

Determination of compound HCVpp entry inhibitory activity in Huh7-high CD81 cells.

Huh7-high CD81 cells were plated at a cell density of 8000 cells per well in 96 well plates (Perkin Elmer, cat #6005660). Cells were plated in 100 μl of Dulbecco's Modified Eagle Medium (DMEM-Glutamax™-I, Invitrogen Cat #10569-010) supplemented with 10% Fetal Bovine Serum (Invitrogen Cat #10082-147) and 1% penicillin/streptomycin (Invitrogen cat #15070-063). Cells were allowed to equilibrate for 24 hours at 37° C. and 5% CO2 at which time compounds and pseudotyped viruses were added. On the day of the assay, HCVpp aliquots were thawed in 37° C. water bath and kept at 4° C. until use. Compounds (or medium as a control) were diluted in 3 fold dilution series in DMEM-Glutamax™-I with 2% DMSO and 2% penicillin/streptomycin. The 100 μl plating medium in each culture well was removed followed by the addition of 50 μl compound dilutions and 50 μl thawed HCVpp. Firefly luciferase reporter signal was read 72 hours after the addition of compounds and HCVpp using the Steady-Glo luciferase Assay System (Promega, cat # E2520) following the manufacturer's instruction. EC50 values were defined as the compound concentration at which a 50% reduction in the levels of firefly luciferase reporter was observed as compared to control samples in the absence of compound and was determined by non-linear fitting of compound dose-response data.

Determination of compound selectivity in Huh7-high CD81 cells.

Huh7 hCD81 cell assay plates and compound dilutions were set up in the same format as in the HCVpp assay. 24 hours after cell plating, thawed VSVpp was diluted by 800 fold in DMEM-Glutamax™-I supplemented with 10% fetal bovine serum. After removal of the cell plating medium from the culture wells, 50 µl compound dilutions and 50 µl diluted VSVpp were added to the wells. Firefly luciferase reporter signal was read 72 hours after the addition of compounds and VSVpp using the Steady-Glo luciferase Assay System (Promega, cat # E2520). EC50 values were defined as the compound concentration at which a 50% reduction in the levels of firefly luciferase reporter was observed as compared to control samples in the absence of compound and was determined by non-linear fitting of compound dose-response data. The EC50 was approximated if maximum percentage inhibition was less than 90% and more than 70%.

Representative assay data can be found in Table II below:

TABLE II

| Compound # | HCVpp GT-1b (EC$_{50}$, µM) | VSVpp (EC$_{50}$, µM) |
|---|---|---|
| 1 | 0.767 | 3.7 |
| 2 | 0.386 | 10.0 |
| 3 | 0.364 | 10.0 |
| 4 | 0.173 | 1.4 |
| 5 | 0.1 | 0.4 |
| 6 | 0.33 | 10.0 |
| 7 | 0.809 | 10.0 |
| 8 | 0.386 | 10.0 |
| 9 | 0.998 | 31.1 |
| 10 | 1.238 | 34.2 |
| 11 | 0.271 | 2.2 |
| 12 | 0.216 | 10.0 |
| 13 | 10 | 10.0 |
| 14 | 6.52 | 15.0 |
| 15 | 6.724 | |
| 16 | 34.772 | |
| 17 | 4.144 | 34.6 |
| 18 | 0.088 | 10.0 |
| 19 | 0.505 | 10.0 |
| 20 | 0.073 | 13.6 |
| 21 | 0.568 | 10.0 |
| 22 | 2.038 | 10.0 |
| 23 | 0.179 | 7.5 |
| 24 | 0.008 | 4.1 |
| 25 | 0.005 | 10.0 |
| 26 | 0.005 | 3.4 |
| 27 | 0.301 | 10.0 |
| 28 | 100 | 100.0 |
| 29 | 13.718 | 8.1 |
| 30 | 5.747 | 5.6 |
| 31 | 5.454 | 4.7 |
| 32 | 0.169 | 21.8 |
| 33 | 0.78 | 10.6 |
| 34 | 0.144 | 1.8 |
| 35 | 0.338 | 2.5 |
| 36 | 0.558 | 11.9 |
| 37 | 0.413 | 8.1 |
| 38 | 3.387 | 35.8 |
| 39 | 0.536 | 5.1 |
| 40 | 0.52 | 3.3 |
| 41 | 0.703 | 32.6 |
| 42 | 0.0527 | 2.4 |
| 43 | 0.771 | 5.3 |
| 44 | 1.156 | 7.8 |

The foregoing invention has been described in some detail by way of illustration and example, for purposes of clarity and understanding. It will be obvious to one of skill in the art that changes and modifications may be practiced within the scope of the appended claims.

Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The invention claimed is:

1. A compound selected from the group consisting of:
   $N^3$-[3,5-Dichloro-4-(6-methoxy-pyridin-3-yl)-phenyl]-1H-[1,2,4]triazole-3,5-diamine;
   $N^3$-[3,5-Dichloro-4-(5-methanesulfonyl-pyridin-3-yl)-phenyl]-1H-[1,2,4]triazole-3,5-diamine;
   5-[4-(5-Amino-1H-[1,2,4]triazol-3-ylamino)-2,6-dichloro-phenyl]-1H-pyridin-2-one;
   $N^3$-[4-(6-Amino-pyridin-3-yl)-3,5-dichloro-phenyl]-1H-[1,2,4]triazole-3,5-diamine;
   $N^3$-[4-(2-Amino-pyrimidin-5-yl)-3,5-dichloro-phenyl]-1H-[1,2,4]triazole-3,5-diamine;
   N3-[3,5-Dichloro-4-(2-methoxy-pyridin-4-yl)-phenyl]-1H-[1,2,4]triazole-3,5-diamine;
   4-[4-(5-Amino-1H-[1,2,4]triazol-3-ylamino)-2,6-dichloro-phenyl]-1H-pyridin-2-one;
   N-{5-[4-(5-Amino-1H-[1,2,4]triazol-3-ylamino)-2,6-dichloro-phenyl]-pyridin-2-yl}-methanesulfonamide;
   $N^5$-[3-Fluoro-4-(6-fluoro-pyridin-3-yl)-5-trifluoromethyl-phenyl]-1H-[1,2,4]triazole-3,5-diamine;
   $N^5$-(3-Fluoro-4-pyridin-3-yl-5-trifluoromethyl-phenyl)-1H-[1,2,4]triazole-3,5-diamine;
   $N^3$-[3,5-Dichloro-4-(6-methanesulfonyl-pyridin-3-yl)-phenyl]-1H-[1,2,4]triazole-3,5-diamine;
   6-[4-(5-Amino-1H-[1,2,4]triazol-3-ylamino)-2,6-dichloro-phenyl]-2,6-diaza-spiro[3.3]heptane-2-carboxylic acid tert-butyl ester;
   $N^3$-(3-Chloro-4-pyridazin-3-yl-phenyl)-1H-[1,2,4]triazole-3,5-diamine;
   $N^3$-[3-Chloro-4-(1-methyl-1H-tetrazol-5-yl)-phenyl]-1H-[1,2,4]triazole-3,5-diamine;
   $N^3$-[3-Chloro-4-(2-methyl-2H-[1,2,4]triazol-3-yl)-phenyl]-1H-[1,2,4]triazole-3,5-diamine;
   $N^3$-(3,5-Dichloro-4-pyrazol-1-yl-phenyl)-1H-[1,2,4]triazole-3,5-diamine;
   4-[4-(5-Amino-1H-[1,2,4]triazol-3-ylamino)-2,6-dichloro-phenyl]-3,6-dihydro-2H-pyridine-1-carboxylic acid tert-butyl ester;
   $N^3$-[3,5-Dichloro-4-(1,2,3,6-tetrahydro-pyridin-4-yl)-phenyl]-1H-[1,2,4]triazole-3,5-diamine;
   4-[4-(5-Amino-1H-[1,2,4]triazol-3-ylamino)-2-chloro-6-trifluoromethyl-phenyl]-3,6-dihydro-2H-pyridine-1-carboxylic acid tert-butyl ester;
   $N^3$-[3-Chloro-4-(1,2,3,6-tetrahydro-pyridin-4-yl)-5-trifluoromethyl-phenyl]-1H-[1,2,4]triazole-3,5-diamine;
   $N^5$-(3,5-Dichloro-4-[1,2,4]triazolo[4,3-a]pyridin-3-yl-phenyl)-1H-[1,2,4]triazole-3,5-diamine;
   N-{3-Chloro-4-[6-(propane-2-sulfonyl)-pyridin-3-yl]-5-trifluoromethyl-phenyl}-4H-[1,2,4]triazole-3,5-diamine;

5-[4-(5-Amino-1H-[1,2,4]triazol-3-ylamino)-2-chloro-6-trifluoromethyl-phenyl]-pyridine-2-sulfonic acid tert-butylamide;

5-[4-(5-Amino-1H-[1,2,4]triazol-3-ylamino)-2-chloro-6-trifluoromethyl-phenyl]-pyridine-2-sulfonic acid (2,2,2-trifluoro-1,1-dimethyl-ethyl)-amide;

5-[4-(5-Amino-1H-[1,2,4]triazol-3-ylamino)-2-chloro-6-trifluoromethyl-phenyl]-pyridine-2-sulfonic acid adamantan-1-ylamide;

$N^3$-[2-Chloro-4'-(4-methyl-piperazin-1-yl)-6-trifluoromethyl-biphenyl-4-yl]-1H-[1,2,4]triazole-3,5-diamine;

$N^3$-(3-Chloro-4-pyridazin-3-yl-phenyl)-1H-[1,2,4]triazole-3,5-diamine;

1-[4-(5-Amino-1H-[1,2,4]triazol-3-ylamino)-phenyl]-1H-pyridin-2-one;

1-[4-(5-Amino-1H-[1,2,4]triazol-3-ylamino)-2-chloro-phenyl]-1H-pyridin-2-one;

1-[4-(5-Amino-1H-[1,2,4]triazol-3-ylamino)-2,6-dichloro-phenyl]-1H-pyridin-2-one;

5-[4-(5-Amino-1H-[1,2,4]triazol-3-ylamino)-2-chloro-6-trifluoromethyl-phenyl]-pyridine-2-carboxylic acid methylamide;

$N^3$-(3,5-Dichloro-4-pyridazin-4-yl-phenyl)-1H-[1,2,4]triazole-3,5-diamine;

1-{3-[4-(5-Amino-1H-[1,2,4]triazol-3-yl amino)-2,6-dichloro-phenyl]-thiophen-2-yl}-ethanone;

N3-(3,5-Dichloro-4-pyridin-4-yl-phenyl)-1H-[1,2,4]triazole-3,5-diamine;

N3-[3,5-Dichloro-4-(5-chloro-thiophen-2-yl)-phenyl]-1H-[1,2,4]triazole-3,5-diamine;

N3-(3,5-Dichloro-4-pyridin-3-yl-phenyl)-1H-[1,2,4]triazole-3,5-diamine;

N3-[3,5-Dichloro-4-(1H-pyrazol-3-yl)-phenyl]-1H-[1,2,4]triazole-3,5-diamine;

N3-(3,5-Dichloro-4-pyrimidin-5-yl-phenyl)-1H-[1,2,4]triazole-3,5-diamine;

N3-[3,5-Dichloro-4-(2-methoxy-pyrimidin-5-yl)-phenyl]-1H-[1,2,4]triazole-3,5-diamine;

N3-[3,5-Dichloro-4-(6-trifluoromethyl-pyridin-3-yl)-phenyl]-1H-[1,2,4]triazole-3,5-diamine;

N3-[3,5-Dichloro-4-(1-methyl-3-trifluoromethyl-1H-pyrazol-4-yl)-phenyl]-1H-[1,2,4]triazole-3,5-diamine;

N3-[3,5-Dichloro-4-(5-chloro-pyridin-3-yl)-phenyl]-1H-[1,2,4]triazole-3,5-diamine; and N3-[3,5-Dichloro-4-(6-methoxy-pyridin-2-yl)-phenyl]-1H-[1,2,4]triazole-3,5-diamine, or a pharmaceutically acceptable salt thereof.

2. A pharmaceutical composition, comprising a therapeutically effective amount of a compound of claim 1 and a pharmaceutically acceptable excipient.

\* \* \* \* \*